(12) United States Patent
Turnbull et al.

(10) Patent No.: US 11,186,603 B2
(45) Date of Patent: Nov. 30, 2021

(54) HEPARAN SULFATE GLYCOMIMETIC COMPOUNDS AND THEIR PHARMACEUTICAL AND COSMECEUTICAL USES

(71) Applicants: VICTORIA LINK LIMITED, Wellington (NZ); Jeremy E. Turnbull, Nr Cleobury Mortimer Shropshire (GB)

(72) Inventors: Jeremy E. Turnbull, Nr Cleobury Mortimer Shropshite (GB); Andrew Munkacsi, Wellington (NZ); Peter Charles Tyler, Wellington (NZ); Olga Vladimirovna Zubkova, Waikanae Beach (NZ)

(73) Assignees: VICTORIA LINK LIMITED, Wellington (NZ); Jeremy E. Turnbull, Nr. Cleobury Mortimer (GB)

( * ) Notice: Subject to any disclaimer, the term of this patent is extended or adjusted under 35 U.S.C. 154(b) by 0 days.

(21) Appl. No.: 16/495,967

(22) PCT Filed: Mar. 23, 2017

(86) PCT No.: PCT/NZ2017/050030
§ 371 (c)(1),
(2) Date: Sep. 20, 2019

(87) PCT Pub. No.: WO2018/174725
PCT Pub. Date: Sep. 27, 2018

(65) Prior Publication Data
US 2020/0131217 A1    Apr. 30, 2020

(51) Int. Cl.
| | | |
|---|---|---|
| *C07H 15/08* | (2006.01) | |
| *A61P 25/28* | (2006.01) | |
| *A61P 35/00* | (2006.01) | |
| *A61K 8/60* | (2006.01) | |
| *A61Q 19/08* | (2006.01) | |

(52) U.S. Cl.
CPC ............ *C07H 15/08* (2013.01); *A61K 8/602* (2013.01); *A61K 8/608* (2013.01); *A61P 25/28* (2018.01); *A61P 35/00* (2018.01); *A61Q 19/08* (2013.01)

(58) Field of Classification Search
CPC ........ C07H 15/08; A61K 8/602; A61K 8/608; A61K 47/56–62
See application file for complete search history.

(56) References Cited

FOREIGN PATENT DOCUMENTS

| | | | |
|---|---|---|---|
| WO | WO-1995/025736 A1 | 9/1995 | |
| WO | WO-03089010 A1 * | 10/2003 | ............. A61P 29/00 |
| WO | WO-2010/088294 A1 | 8/2010 | |
| WO | WO-2014/084744 A1 | 6/2014 | |

OTHER PUBLICATIONS

Foxhall, C. et al "Sulfated malto-oligosaccharides bind to basic FGF . . . " J. Cell. Physiol., vol. 168, pp. 657-667. (Year: 1996).*
Zioncheck, T. et al "Sulfated oligosaccharides promote hepatocyte growth factor . . . " J. Biol. Chem., vol. 270, No. 28, pp. 16871-16878. (Year: 1995).*
International Search Report and Written Opinion dated Aug. 7, 2017 for corresponding PCT Application No. PCT/NZ2017/050030.
International Preliminary Report on Patentability dated Sep. 24, 2019 for corresponding PCT Application No. PCT/NZ2017/050030.
Costantino, L. et al., "Nanoparticulate drug carriers based on hybrid poly(D,L-lactide-co-glycolide)-dendron structures", Biomaterials, 2006, vol. 27 (26), pp. 4635-4645, p. 4641, Scheme 3, compounds 5a-c.
CAS Registry No. 1612286-21-1, STN Entry Date Jun. 25, 2014, 4,7,10,17,21,28,31,34-Octaoxa-13,25-diazaheptatriacontanediamide, 19,19-bis[25-[[2-deoxy-6-O-sulfo-2-(sulfoamino)-α-D-glucopyranosyl]oxy]-5,18-dioxo-2,9,12,15-tetraoxa-6,19-diazapentacos-1-yl]-N1,N37-bis[6-[[2-deoxy-6-O-sulfo-2-(sulfoamino)-α-D-glucopyranosyl]oxy]hexyl]-14,24-dioxo-structure.
CAS Registry No. 1612286-20-0; STN Entry DateJun. 25, 2014; 4,7,10,17,21,28,31,34-Octaoxa-13,25-diazaheptatriacontanediamide,19,19-bis[25-[[2-(acetylamino)-2-deoxy-6-O-sulfo-α-D-glucopyranosyl]oxy]-5,18-dioxo-2,9,12,15-tetraoxa-6,19-diazapentacos-1-yl]-N1,N37-bis[6-[[2-(acetylamino)-2-deoxy-6-O-sulfo-α-D-glucopyranosyl]oxy]hexyl]-14,24-dioxo-structure.
CAS Registry No. 1612286-10-8; STN Entry Date Jun. 25, 2014; 13,17-Dioxa-9,21-diazanonacosanediamide, N1,N29-bis[6-[[2-(acetylamino)-2-deoxy-6-O-sulfo-α-D-glucopyranosyl]oxy]hexyl]-15,15-bis[[3-[[8-[[6-[[2-(acetylamino)-2-deoxy-6-O-sulfo-α-D-glucopyranosyl]oxy]hexyl]amino]-8-oxooctyl]amino]-3-oxopropoxy]methyl]-10,20-dioxo-structure.
CAS Registry No. 1612286-09-5; STN Entry Date Jun. 25, 2014; Propanamide, 3,3'-[[2,2-bis[[3-[[6-[[2-(acetylamino)-2-deoxy-6-O-sulfo-α-D-glucopyranosyl]oxy]hexyl]amino]-3-oxopropoxy]methyl]-1,3-propanediyl]bis(oxy)]bis[N-[6-[[2-(acetylamino)-2-deoxy-6-O-sulfo-α-D-glucopyranosyl]oxy]hexyl]-structure.
Choudhury, Ambar K., et al., "Synthesis of a Cellobiosylated Dimer and Trimer and of Cellobiose-Coated Polyamidoamine (PAMAM) Dendrimers to Study Accessibility of an Enzyme, Cellodextrin Phosphorylase," European Journal of Organic Chemistry, vol. 2003, No. 13, 2003, pp. 2462-2470 XP055746719.
Jendresen, Charlotte B., et al., "Overexpression of Heparanase Lowers the Amyloid Burden in Amyloid-[beta] Precursor Protein Transgenic Mice," Journal of Biological Chemistry, vol. 290, No. 8, Feb. 20, 2015 (Feb. 20, 2015), pp. 5053-5064; us ISSN: 0021-9258, DOI: 10.1074/jbc.M114.600569 XP055749517.
Patey S J, et al., "Heparin derivatives as inhibitors of BACE-1, the Alzheimer's [beta]-secretase, with reduced activity against factor Xa and other proteases," Journal of Medicinal Chemistry, 2006, vol. 49, No. 20, pp. 6129-6132, ISSN: 0022-2623, DOI: 10.1021/JM0512210 XP002446614.

* cited by examiner

*Primary Examiner* — Leigh C Maier
(74) *Attorney, Agent, or Firm* — Polsinelli PC

(57) ABSTRACT

The invention relates to dendritic compounds, the use of these compounds as pharmaceuticals, pharmaceutical and cosmeceutical compositions containing the compounds, and methods of treating cancer, inflammation, diabetic nephropathy, neurodegenerative disorders, Niemann-Pick Type C disease, or dermatological conditions.

19 Claims, 3 Drawing Sheets

HEPARAN SULFATE GLYCOMIMETIC COMPOUNDS AND THEIR PHARMACEUTICAL AND COSMECEUTICAL USES

CROSS-REFERENCE TO RELATED APPLICATIONS

This application is a national stage application (under 35 U.S.C. § 371) of PCT/NZ2018/050030, filed Mar. 23, 2017, which is incorporated herein by reference in its entirety.

TECHNICAL FIELD

This invention relates generally to sulfated dendritic compounds that are mimetics of heparan sulphate, the use of these compounds as pharmaceuticals and cosmeceuticals, pharmaceutical or cosmeceutical compositions containing the compounds, processes for preparing the compounds, and methods of treating various diseases or conditions. The invention has particular relevance for the treatment or prevention of cancer, inflammation, diabetic nephropathy, neurodegenerative disorders, Niemann-Pick Type C disease, and for certain cosmeceutical and dermatological uses.

BACKGROUND

Heparanase is an endo-β-D-glucuronidase that degrades the heparan sulfate glycosaminoglycan side chains of proteoglycans in extracellular matrix and basement membrane. Heparanase appears to regulate syndecan clustering, shedding and mitogen binding. Heparanase enzymatic activity is known to be important in the promotion of tumor angiogenesis, primary tumor growth, invasion and metastasis. Heparanase cleaves heparan sulfate side chains at sites of low sulfation, thus facilitating structural alterations of the extracellular matrix and basement membrane underlying epithelial and endothelial cells. Importantly, heparanase activity correlates with the metastatic potential of cancer cells. The interaction between heparanase and its substrate, heparan sulfate has been well characterised. Heparanase has been identified as the single predominant heparan sulfate-degrading enzyme in human cancer, sparking considerable interest in the development of heparanase inhibitors for potential therapeutic applications including cancer, inflammation and diabetic nephropathy. The function of heparanase and its therapeutic potential is reviewed in Fux, L., et al., Trends Biochem. Sci., 2009 October, 34(10):511-519.

As populations age neurodegenerative disorders, such as Alzheimer's disease, become more prevalent. Alzheimer's disease is a common form of dementia, and is progressive and irreversible. The pathogenesis of the disease is thought to involve cerebral deposits of aggregated amyloid β-peptide. The first, and rate-limiting, step in the generation of amyloid β-peptide is cleavage of amyloid precursor protein by β-secretase (β-site amyloid precursor protein cleaving enzyme-1, β-secretase-1, hereinafter "BACE-1"). This makes BACE-1 an attractive target for new Alzheimer's therapies.

Heparan sulfate and its highly sulfated analogue heparin have been shown to inhibit BACE-1 activity. Heparan sulfate and heparin are both glycosaminoglycans comprising 1,4-linked disaccharide units of β-D-glucuronic acid or α-L-iduronic acid with N-acetyl-α-D-glucosamine (dominant in the case of heparan sulfate) or N-sulfo-α-D-glucosamine (dominant in the case of heparin) and additional O-sulfate ester substituents. Heparin is a well-known pharmaceutical with anti-coagulant activity. However, the anti-coagulant properties of heparin need to be attenuated if it is to be used for other pharmaceutical applications. Otherwise possible side effects, such as internal bleeding and impaired blood clotting, can be problematic.

Niemann-Pick Type C (NPC) patients are not able to metabolise cholesterol and other lipids properly within the cell. Consequently, excessive amounts of cholesterol accumulate within the liver and spleen and excessive amounts of other lipids accumulate in the brain.

There is considerable variation in when Type C symptoms first appear and in the progression of the disease. Symptoms may appear as early as a few months of age or as late as adulthood.

Vertical gaze palsy (the inability to move the eyes up and down), enlarged liver, enlarged spleen, or jaundice in young children are strong indications that NPC should be considered. It is common for only one or two symptoms to appear in the early stages of the disease. In most cases, neurological symptoms begin appearing between the ages of 4 and 10. Generally, the later neurological symptoms begin, the slower the progression of the disease.

NPC has an estimated 500 cases diagnosed worldwide. It is believed, however, that the number of people affected by NPC is higher, but diagnostic difficulties do not allow an accurate assessment of the occurrence rate. NPC has been initially diagnosed as a learning disability, mild retardation, "clumsiness," and delayed development of fine motor skills. It is not uncommon for a family to spend several years seeking a diagnosis before NPC is identified.

NPC is always fatal. The majority of children with NPC die before the age of 20 (many die before the age of 10). Late onset of symptoms can lead to longer life spans but it is extremely rare for any person with NPC to reach the age of 40.

The mechanisms by which endocytosed lipids such as cholesterol and sphingolipids leave the lysosomal compartment of a eukaryotic cell are obscure, despite the severe consequences of impaired transport in the pathology of neurodegenerative diseases. Two strikingly conserved genes encode proteins that when defective result in NPC disease, a fatal pediatric neurodegenerative disease caused by a lysosomal accumulation of cholesterol and sphingolipids. The clinical hallmark of NPC disease, for individuals that survive past the neonatal stage, is progressive dementia with markedly reduced executive function and global cognitive impairment, typically culminating in loss of life before adolescence. NPC disease is conferred by mutations in either the NPC1 gene (95% of cases) or NPC2 gene (5% of cases). NPC1 encodes an ~13-pass lysosomal transmembrane domain protein, and NPC2 encodes a soluble low molecular weight lumenal protein in the lysosome. Both proteins possess lipid-binding domains and have enigmatic functions as putative lipid transporters or chaperones. NPC2 likely "hands off" cholesterol to NPC1, but the interactions of this pathway before and after this event are unknown. As a result, treatments are currently experimental and limited to the suspected targets, i.e. modulating the metabolism of cholesterol or sphingolipids. Approved therapies for NPC disease, particularly in the United States, are thus limited to palliative treatment of the symptoms, and there is a striking clinical need for a novel intervention in what is an invariably fatal disease. There is a need for further oligosaccharides which can lower cholesterol levels in NPC.

Heparan sulfate is used in a number of cosmeceutical and dermatological formulations. Heparan sulfate oligosaccharides are highly sulfated glycosaminoglycans that play a crucial role in a range of essential physiological processes. Heparan sulfate binds collagen (the main protein of connective tissue), regulates its synthesis and has the ability to organise water molecules and fill the spaces between water molecules. Collagen is responsible for strength, texture and elasticity of tissue, but its amount in the skin decreases over time by ~1% per year. Various glycosaminoglycan compounds, such as hyaluronic acid and low molecular weight heparin, have already found use in multiple cosmeceutical formulations delivering drug-like benefits and a rejuvenating effect to the skin. However, the exploitation of heparan sulfate oligosaccharides has been hindered by the complexity of their synthesis. The applicants recently developed robust and scalable method for preparing novel polyvalent displays of small specific heparan sulfate fragments on chemical structures known as dendritic cores. This methodology greatly simplified the synthesis requirements while retaining the desired bioactivity of the heparan sulfate structures. Biologically active heparan sulfate glycomimetic compounds have the potential to dramatically slow, and possibly reverse, the signs and symptoms of skin aging.

In the search for improved therapies and treatments for the abovementioned diseases and disorders, the applicants have investigated glycomimetics of heparan sulfate. Certain compounds based on heparan sulfate have been prepared by the applicants and are disclosed in WO 2014/084744 as being potentially effective for treating disorders in which BACE-1 is implicated. These compounds are mimetics of heparan sulfate with di- and tetra-saccharide fragments of heparan sulfate attached to dendritic cores. These fragments were prepared from glucose and glucosamine monosaccharides by multistep syntheses involving glycosylations and selective protection-deprotection reactions employing an orthogonal protecting group strategy. Suitably protected heparan sulfate fragments were attached to the core and selective deprotection allowed selective sulfation leading to the target compounds. Although this approach reduced the number of reaction steps compared to other approaches to the synthesis of heparan sulfate oligosaccharides, the synthesis process remained lengthy. The applicants have now developed a new method for synthesising heparan sulfate glycomimetic compounds using readily available and affordable starting materials and a significantly shortened synthesis process which no longer requires an orthogonal protecting group strategy.

It is therefore an object of the invention to provide effective heparanase inhibitors, effective BACE-1 inhibitors, effective cholesterol lowering agents in NPC patients, or effective ingredients for cosmeceutical and dermatological formulations, or to at least provide useful alternatives to existing compounds for these uses.

SUMMARY OF INVENTION

In a first aspect, the present invention provides a compound of formula (i):

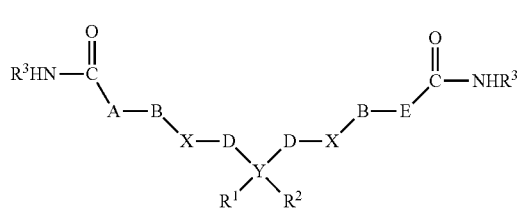

(i)

wherein:
$R^3$ is a radical of formula (ii), (iii) or (iv):

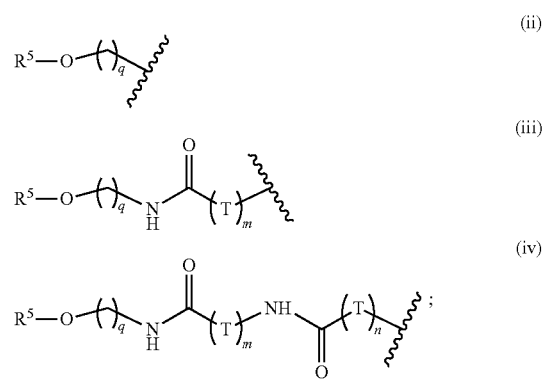

$R^5$ is a radical of formula (v), (vi) or (vii):

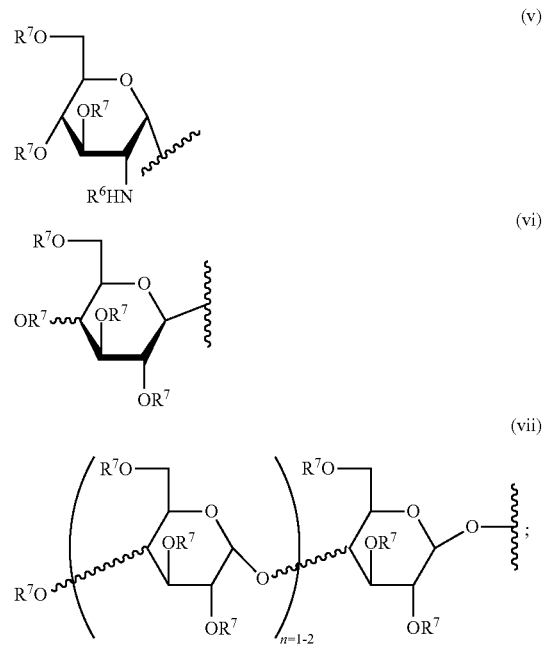

$R^6$ is H, $SO_3H$, an acyl group which is optionally radio-labelled, or $R^6$ is $C(=O)R^8$ where
$R^8$ is aryl or aralkyl;
$R^7$ is H or $SO_3H$;
and:
Y is O; B is O; $R^1$ and $R^2$ are absent; and either A, E, D and X are all $CH_2$; or A, D and X are all $CH_2$ and E is $(CH_2CH_2O)_t{}^\#CH_2$ wherein $^\#$ indicates a point of attachment of E to its adjacent carbonyl group; t is an integer from 1 to 10;
or:
Y is C; $R^1$ and $R^2$ are both H; and A, E, B and D are $CH_2$ and X is O;
or:
Y is C; A is $(CH_2)_u$; $R^1$ and $R^2$ are both H; B, X, D and E are all absent; and u is an integer from 1 to 10;
or:
Y is C; X is O; B is $(CH_2)_p$; A, E and D are all $CH_2$; and $R^1$ is H, NHZ or $C_{1-6}$alkyl and $R^2$ is a radical of formula (viii), (ix) or (x):

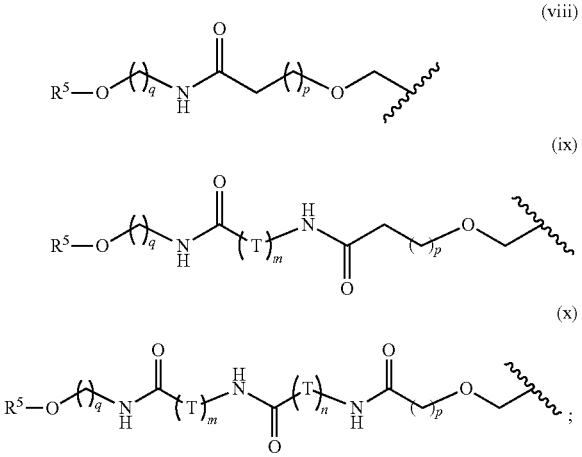

Z is H, acyl, $C(O)(CH_2)_wN(H)G$, or an imaging agent;
w is an integer from 1 to 11;
G is H, acyl, Boc (t-butoxycarbonyl), Troc (2,2,2-trichloroethyloxycarbonyl), Fmoc (9-fluorenylmethoxycarbonyl), Cbz (benzyloxycarbonyl), or an imaging agent;
or:
Y is C; X is O; B is $(CH_2)_p$; A, E and D are all $CH_2$; and $R^1$ and $R^2$, both the same, are a radical of formula (viii), (ix) or (x):

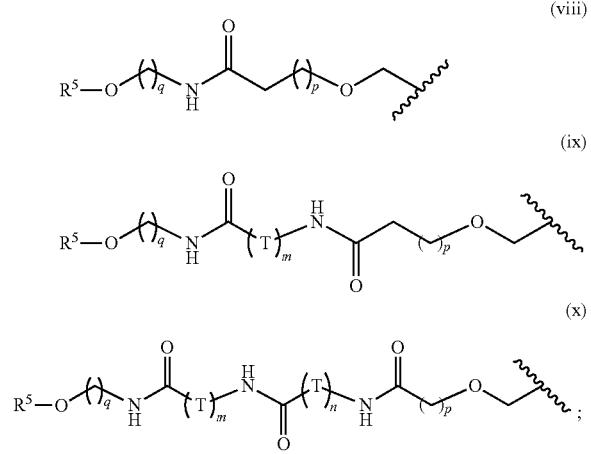

each T is independently selected from the group consisting of $(CH_2CH_2O)_xCH_2CH_2$ and $CH_2$;
each x is independently an integer from 1 to 12;
n is an integer from 1 to 11, provided that when T is $(CH_2CH_2O)_xCH_2CH_2$ then n is 1;
q is an integer from 1 to 11;
m is an integer from 1 to 11, provided that when T is $(CH_2CH_2O)_xCH_2CH_2$ then m is 1;
p is an integer from 1 to 5;
or a pharmaceutically acceptable salt thereof, or a prodrug thereof.

In another aspect the invention provides a composition comprising an effective amount of a compound of formula (i) and a suitable carrier, diluent or excipient. The composition may be a pharmaceutical or cosmeceutical composition.

In another aspect the invention provides a method of treating or preventing any one or more of cancer, inflammation, diabetic nephropathy, a neurodegenerative disorder, Niemann-Pick Type C disease, and a dermatological condition comprising administering a pharmaceutically effective amount of a compound of formula (i) to a patient requiring treatment.

In another aspect the invention provides a method of rejuvenating skin or preventing skin-aging comprising administering an effective amount of a compound of formula (i) to human skin.

In another aspect the invention provides the use of a compound of formula (i) for treating or preventing any one or more of cancer, inflammation, diabetic nephropathy, a neurodegenerative disorder, Niemann-Pick Type C disease, and a dermatological condition.

In another aspect the invention provides the use of a compound of formula (i) for rejuvenating skin or preventing skin-aging.

In another aspect the invention provides the use of a compound of formula (i) in the manufacture of a medicament for treating or preventing any one or more of cancer, inflammation, diabetic nephropathy, a neurodegenerative disorder, Niemann-Pick Type C disease, and a dermatological condition.

In another aspect the invention provides the use of a compound of formula (i) in the manufacture of a medicament for treating or preventing skin-aging.

In another aspect the invention provides a pharmaceutical composition for treating or preventing any one or more of cancer, inflammation, diabetic nephropathy, a neurodegenerative disorder, Niemann-Pick Type C disease, and a dermatological condition, comprising a compound of formula (i).

The neurodegenerative disorders include, but are not limited to, senile dementia, pre-senile dementia, multi-infarct dementia and Alzheimer's disease.

In another aspect the invention provides a compound of formula (i) in combination with at least one other compound, e.g. a second drug compound. The other compound may be, for example, an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation, or memantine.

In another aspect the invention provides the use of a compound of formula (i) in combination with at least one other compound, e.g. a second drug compound, e.g. an oligosaccharide compound, a cyclitol such as scyllo-inositol or D-chiro-inositol, an acetylcholinesterase inhibitor, a nicotinic agonist, an antibody targeting β-amyloid, an inhibitor of tau aggregation, or memantine, for treating or preventing any one or more of cancer, inflammation, diabetic nephropathy, a neurodegenerative disorder, Niemann-Pick Type C disease, and a dermatological condition.

In another aspect the invention provides a method of treating or preventing any one or more of cancer, inflammation, diabetic nephropathy, a neurodegenerative disorder, Niemann-Pick Type C disease, and a dermatological condition comprising administering a pharmaceutically effective amount of a compound of formula (i) in combination with at least one other compound, e.g. a second drug compound, e.g. an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation or memantine. The compound of formula (i) and the other compound may be administered separately, simultaneously or sequentially.

DETAILED DESCRIPTION

Definitions

Figure 1:
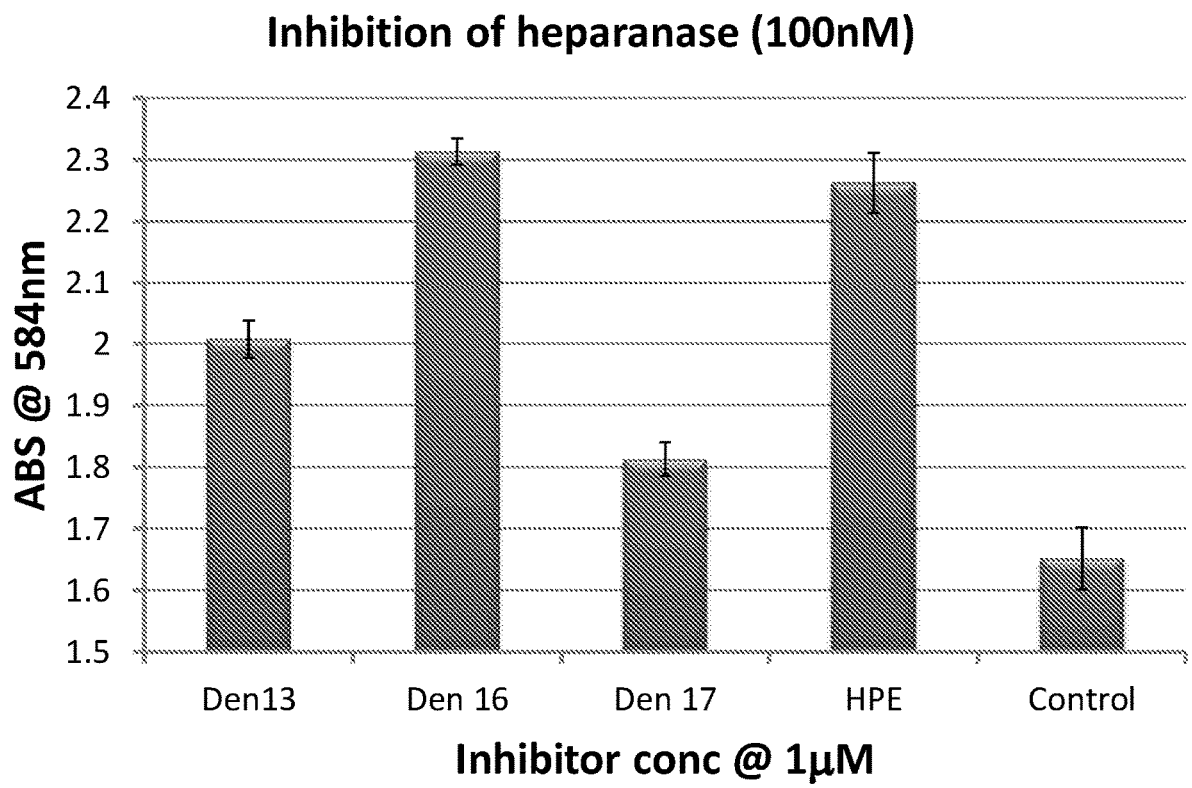
FIG. 1 shows the inhibition of heparanase by compounds of the invention at an inhibitor concentration of 1 μM.

The term "$C_1$-$C_6$alkyl" means any saturated hydrocarbon radical having up to 6 carbon atoms and is intended to include both straight- and branched-chain alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethyl propyl group, 1-ethylpropyl group, 2-ethylpropyl group, n-hexyl group and 1-methyl-2-ethylpropyl group.

The term "alkylene" means a diradical corresponding to a $C_1$-$C_{12}$alkyl group, where $C_1$-$C_{12}$alkyl means any saturated hydrocarbon radical having up to 12 carbon atoms, and is intended to include straight chain alkyl groups. Examples of alkylene groups include methylene group and ethylene group.

The term "acyl" means C(=O)R' group, where R' is a $C_1$-$C_{30}$alkyl group, where $C_1$-$C_{30}$alkyl means any saturated hydrocarbon radical having up to 30 carbon atoms, and is intended to include straight chain alkyl groups. Examples include acetyl group.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an aryl group which is attached to an alkylene moiety, where aryl and alkylene are as defined above. Examples include benzyl group.

The term "imaging agent" means any substance administered to a patient for the purpose of obtaining information about internal organs, cellular processes, healthy tissue, and unhealthy tissue such as tumours, such information typically being used to diagnose disease or monitor treatment effects, including radiolabelled chemicals and fluorescent chemicals. Examples include *CH$_3$*C(O)— where *C denotes $^{13}$C or $^{14}$C, 5-TAMRA (5-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza s-indacene), and Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate).

The term "prodrug" as used herein means a pharmacologically acceptable derivative of the compounds of formula (I) such that an in vivo biotransformation of the derivative gives the compound as defined in formula (I). Prodrugs of compounds of formulae (I) may be prepared by modifying functional groups present in the compounds in such a way that the modifications are cleaved in vivo to give the parent compound. Typically, prodrugs of the compounds of formula (I) will be ester prodrug forms.

The term "cosmeceutical" as used herein means the combination of a pharmaceutical and a cosmetic, and refers generally to a cosmetic product containing one or more biologically active ingredient that has, or is purported to have, a pharmaceutical effect.

The term "pharmaceutically acceptable salts" is intended to apply to non-toxic salts such as ammonium salts, metal salts, e.g. sodium salts, or salts of organic cations, or a mixture thereof.

The term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in *Protective Groups in Organic Synthesis* (3$^{rd}$ Ed.), T. W. Greene and P. G. M. Wuts, John Wiley & Sons Inc (1999). Examples of protecting groups include, but are not limited to: O-benzyl, O-benzhydryl, O-trityl, O-tert-butyldimethylsilyl, O-tert-butyldiphenylsilyl, O-4-methylbenzyl, O-acetyl, O-chloroacetyl, O-methoxyacetyl, O-benzoyl, O-4-bromobenzoyl, O-4-methylbenzoyl, O-fluorenylmethoxycarbonyl and O-levulinoyl.

The term "patient" includes human and non-human animals.

The terms "treatment", "treating" and the like include the alleviation of one or more symptoms, or improvement of a state associated with the disease or disorder, for example, improvement in cognition, improvement in memory function.

The terms "preventing", "prevention" and the like include the prevention of one or more symptoms associated with the disease or disorder.

The compounds of the invention are useful in both free base form and in the form of salts and/or solvates.

Those skilled in the art will appreciate that the compounds of the invention may exist as stereoisomers. For example, structures shown herein which include bonds " 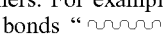 " linking the sugar ring with the carboxyl group (such as shown below) are intended to include gluco- and galacto-forms of the sugar. Those skilled in the art will also appreciate that it is possible for the compounds of the invention to incorporate only gluco-forms, only galacto-forms, or mixtures of gluco- and galacto-forms.

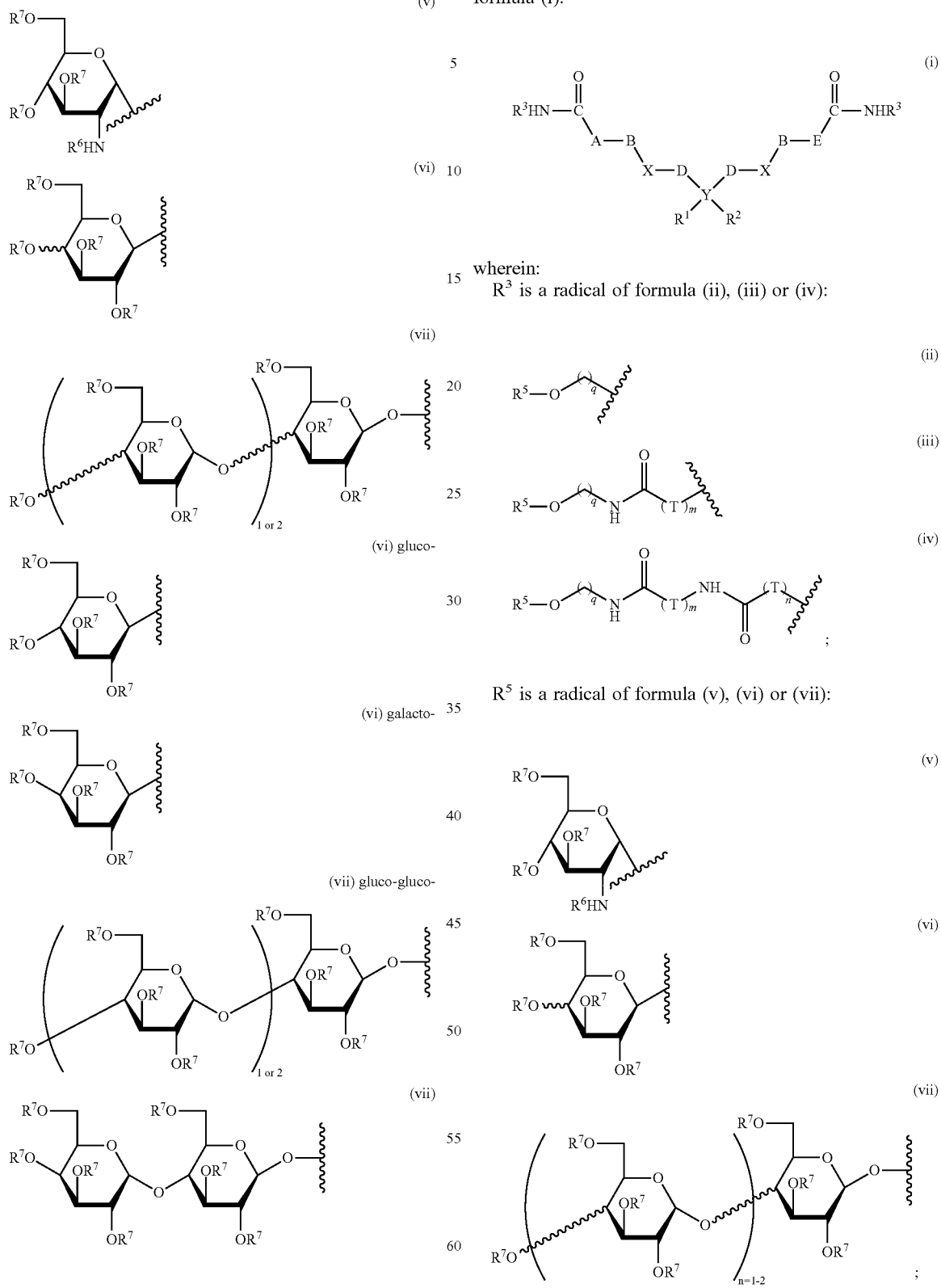

The Compounds of the Invention

Compounds of formula (i) are herein described as "compounds of the invention". A compound of the invention includes a compound in any form, e.g. in free form or in the form of a salt or a solvate.

The compounds of the invention are defined according to formula (i):

wherein:
R³ is a radical of formula (ii), (iii) or (iv):

R⁵ is a radical of formula (v), (vi) or (vii):

R⁶ is H, SO₃H, an acyl group which is optionally radio-labelled, or R⁶ is C(=O)R⁸ where
R⁸ is aryl or aralkyl;
R⁷ is H or SO₃H;

and:

Y is O; B is O; $R^1$ and $R^2$ are absent; and either A, E, D and X are all $CH_2$; or A, D and X are all $CH_2$ and E is $(CH_2CH_2O)_t^{\#}CH_2$ wherein $^{\#}$ indicates a point of attachment of E to its adjacent carbonyl group; t is an integer from 1 to 10;

or:

Y is C; $R^1$ and $R^2$ are both H; and A, E, B and D are $CH_2$ and X is O;

or:

Y is C; A is $(CH_2)_u$; $R^1$ and $R^2$ are both H; B, X, D and E are all absent; and u is an integer from 1 to 10;

or:

Y is C; X is O; B is $(CH_2)_p$; A, E and D are all $CH_2$; and $R^1$ is H, NHZ or $C_{1-6}$alkyl and $R^2$ is a radical of formula (viii), (ix) or (x):

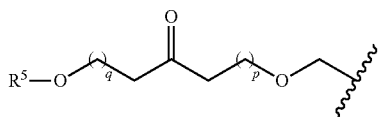

(viii)

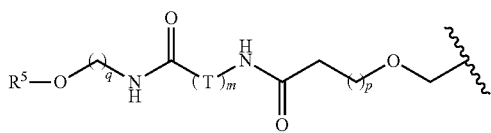

(ix)

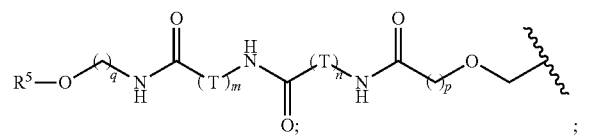

(x)

Z is H, acyl, $C(O)(CH_2)_wN(H)G$, or an imaging agent;
w is an integer from 1 to 11;
G is H, acyl, Boc (t-butoxycarbonyl), Troc (2,2,2-trichloroethyloxycarbonyl), Fmoc (9-fluorenylmethoxycarbonyl), Cbz (benzyloxycarbonyl), or an imaging agent;

or:

Y is C; X is O; B is $(CH_2)_p$; A, E and D are all $CH_2$; and $R^1$ and $R^2$, both the same, are a radical of formula (viii), (ix) or (x):

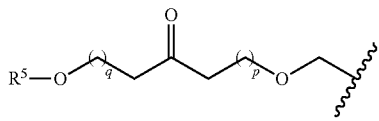

(viii)

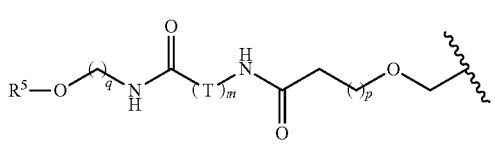

(ix)

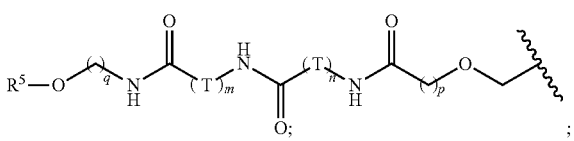

(x)

each T is independently selected from the group consisting of $(CH_2CH_2O)_xCH_2CH_2$ and $CH_2$;
each x is independently an integer from 1 to 12;
n is an integer from 1 to 11, provided that when T is $(CH_2CH_2O)_xCH_2CH_2$ then n is 1;
q is an integer from 1 to 11;
m is an integer from 1 to 11, provided that when T is $(CH_2CH_2O)_xCH_2CH_2$ then m is 1;
p is an integer from 1 to 5;

or a pharmaceutically acceptable salt thereof, or a prodrug thereof.

In some embodiments of the invention each T is $CH_2$. In preferred embodiments at least one T is $CH_2$ or at least one T is $(CH_2CH_2O)_xCH_2CH_2$.

In some embodiments of the invention the pharmaceutically acceptable salt is an ammonium salt, a metal salt, or a salt of an organic cation, or a mixture thereof. In certain specific embodiments the salt is a sodium salt.

In some embodiments of the invention the radical (vi) or (vii) is all gluco-form. In other embodiments the radical (vi) or (vii) may be all galacto-form.

In some embodiments radical (v) is:

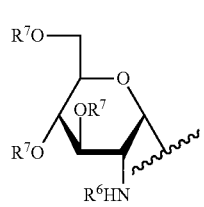

(v)

In some embodiments radical (vi) is:

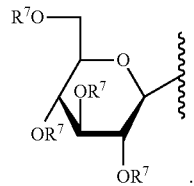

In some embodiments radical (vi) is:

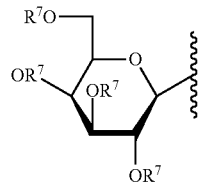

In some embodiments radical (vii) is:

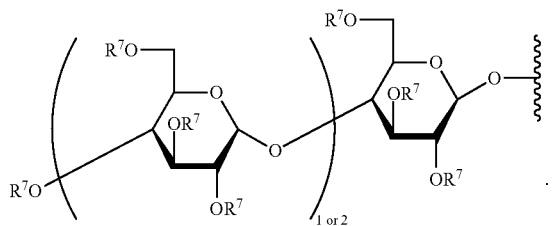

In some embodiments radical (vii) is:

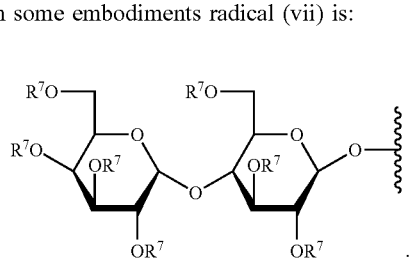

$R^6$ may be an acetyl group which is optionally radiolabelled.

Z may be acetyl.

G may be acetyl.

In some embodiments $R^1$ and $R^2$ are both a radical of formula (viii):

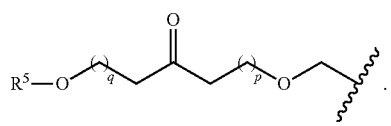 (viii)

In some embodiments $R^1$ and $R^2$ are both a radical of formula (ix):

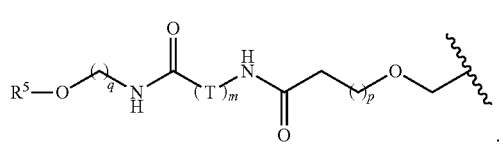 (ix)

In some embodiments $R^1$ and $R^2$ are both a radical of formula (x):

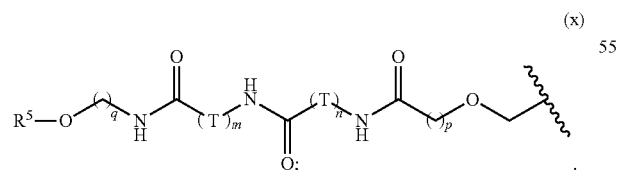 (x)

In some embodiments, in $R^1$, one T is $(CH_2CH_2O)_xCH_2CH_2$ and one T is $CH_2$ and in $R^2$ one T is $(CH_2CH_2O)_xCH_2CH_2$ and one T is $CH_2$. In some embodiments, in both of $R^1$ and $R^2$, $(T)_m$ is $(CH_2CH_2O)_xH_2CH_2$ and $(T)_n$ is $(CH_2)_n$. In alternative embodiments, in both of $R^1$ and $R^2$, $(T)_m$ is $(CH_2)_m$ and $(T)_n$ is $(CH_2CH_2O)_xCH_2CH_2$.

$R^1$ and $R^2$ may both be a radical of formula (ii)(a) wherein each T is $(CH_2CH_2O)_xCH_2CH_2$, wherein each x in each radical of formula (ii)(a) is independently selected.

In some embodiments $R^3$ is a radical of formula (ii):

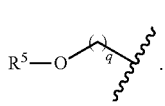 (ii)

In some embodiments $R^3$ is a radical of formula (iii):

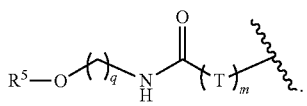 (iii)

In some embodiments $R^3$ is a radical of formula (iv)

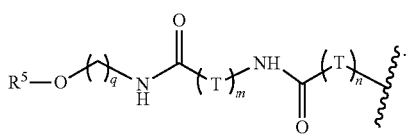 (iv)

In some embodiments, in $R^3$, one T is $(CH_2CH_2O)_xCH_2CH_2$ and one T is $CH_2$. In some embodiments, in $R^3$, $(T)_m$ is $(CH_2CH_2O)_xCH_2CH_2$ and $(T)_n$ is $(CH_2)_n$. In alternative embodiments, in $R^3$, $(T)_n$ is $(CH_2CH_2O)_xCH_2CH_2$ and $(T)_m$ is $(CH_2)_m$.

In some embodiments $R^3$ is a radical of formula (iv)(a) wherein each T is $(CH_2CH_2O)_xCH_2CH_2$, wherein each x in each radical of formula (iv)(a) is independently selected.

In some embodiments $R^1$ may preferably be H or $C_{1-6}$alkyl, e.g. $CH_3$ or $CH_2CH_3$. $R^1$ may alternatively be $NH_2$. In other embodiments $R^1$ may be NHZ, and Z is preferably $C(O)(CH_2)_wN(H)G$, e.g. where G is Troc (2,2,2-trichloroethyloxycarbonyl), Fmoc (fluorenylmethyloxycarbonyl) or Cbz (benzyloxycarbonyl). Preferably w is 7.

In some embodiments Y is O; B is O; $R^1$ and $R^2$ are absent; and either A, E, D and X are all $CH_2$ or A, D and X are all $CH_2$ and E is $(CH_2CH_2O)_tCH_2$; and t is an integer from 1 to 10, preferably an integer from 1 to 2.

In some embodiments Y is C; $R^1$ and $R^2$ are both H; A, E, B and D are $CH_2$ and X is O.

In some embodiments Y is C; A is $(CH_2)_u$; $R^1$ and $R^2$ are both H; B, X, D and E are all absent; and u is an integer from 1 to 10.

In some embodiments:

Y is C; X is O; A, E and D are all $CH_2$; B is $(CH_2)_p$;
$R^1$ is H, NHZ or $C_{1-6}$alkyl;
$R^2$ is a radical of formula (viii), a radical of formula (ix) or a radical of formula (x):

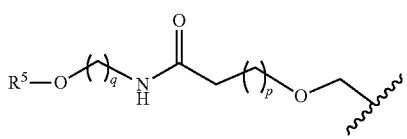 (viii)

(ix)

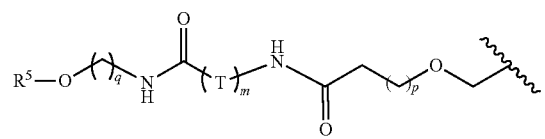

(x)

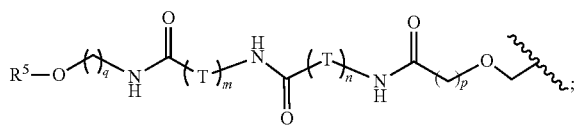

Z is H, acyl, C(O)(CH$_2$)$_w$N(H)G, or an imaging agent;

w is an integer from 1 to 11; and

G is H, acyl, Boc (t-butoxycarbonyl), Troc (2,2,2-trichloroethyloxycarbonyl), Fmoc (9-fluorenylmethoxycarbonyl), Cbz (carboxybenzyl), or an imaging agent.

In some embodiments R$^1$ is H, NHZ or C$_{1-6}$alkyl and R$^2$ is a radical of formula (viii):

(viii)

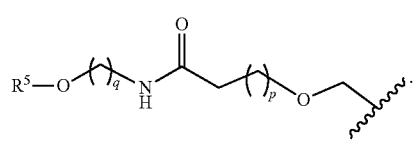

In some embodiments R$^1$ is H, NHZ or C$_{1-6}$alkyl and R$^2$ is a radical of formula (ix):

(ix)

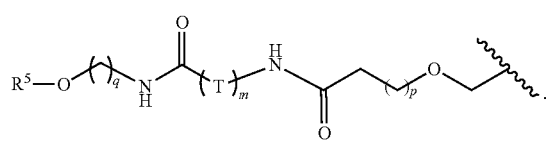

In some embodiments R$^1$ is H, NHZ or C$_{1-6}$alkyl and R$^2$ is a radical of formula (x):

(x)

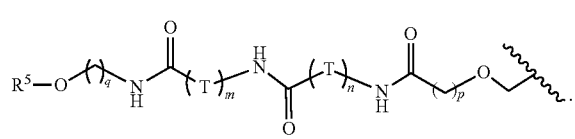

In some embodiments, in R$^2$, (T)$_m$ is (CH$_2$CH$_2$O)$_x$CH$_2$CH$_2$ and (T)$_n$ is (CH$_2$)$_n$. In some embodiments, in R$^2$, (T)$_m$ is (CH$_2$)$_m$ and (T)$_n$ is (CH$_2$CH$_2$O)$_x$CH$_2$CH$_2$. In some embodiments R$^2$ is a radical of formula (ii)(a) wherein each T is (CH$_2$CH$_2$O)$_x$CH$_2$CH$_2$, wherein each x in each radical of formula (ii)(a) is independently selected.

In some embodiments Y is C; X is O; A, E and D are all CH$_2$; B is (CH$_2$)$_p$; and R$^1$ and R$^2$, both the same, are a radical of formula (viii), a radical of formula (ix) or a radical of formula (x):

(viii)

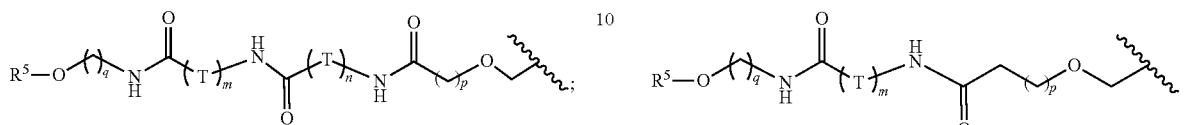

(ix)

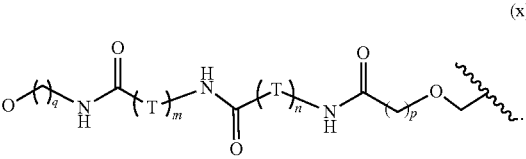

(x)

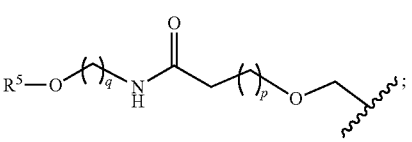

In some embodiments Y is C; X is O; A, E and D are all CH$_2$; B is (CH$_2$)$_p$; R$^1$ and R$^2$, both the same, are a radical of formula (viii):

(viii)

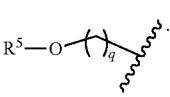

and R$^3$ is a radical of formula (ii):

(ii)

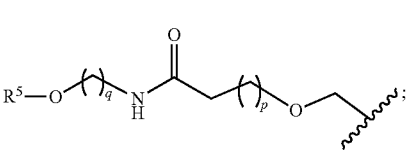

In some embodiments Y is C; X is O; A, E and D are all CH$_2$; B is (CH$_2$)$_p$; R$^1$ and R$^2$, both the same, are a radical of formula (viii):

(viii)

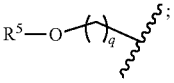

R$^3$ is a radical of formula (ii):

(ii)

and $R^5$ is a radical of formula (vii):

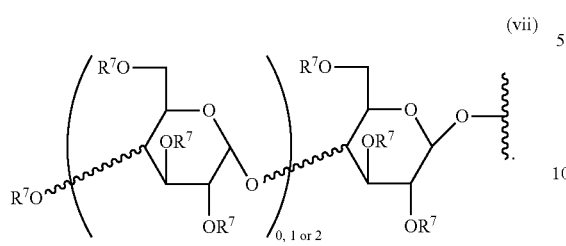

In some embodiments Y is C; X is O; A, B, E and D are all $CH_2$; $R^1$ and $R^2$, both the same, are a radical of formula (ix):

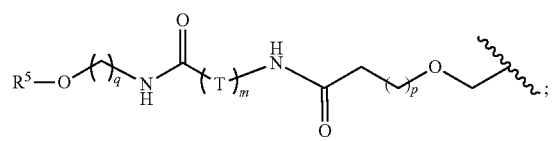

and $R^3$ is a radical of formula (iii):

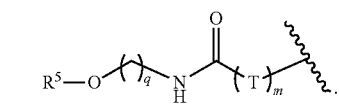

In some embodiments Y is C; X is O; A, B, E and D are all $CH_2$; $R^1$ and $R^2$, both the same, are a radical of formula (x):

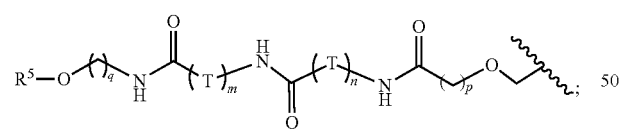

and $R^3$ is a radical of formula (iv):

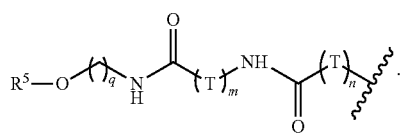

In some embodiments Y is C; X is O; A, B, E and D are all $CH_2$; $R^1$ and $R^2$, both the same, are a radical of formula (ix):

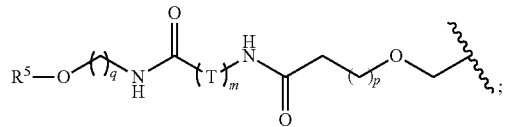

$R^3$ is a radical of formula (iii):

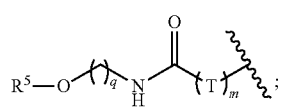

and $R^5$ is a radical of formula (vii):

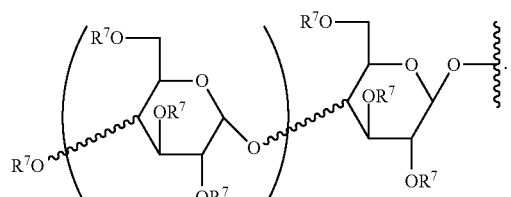

In some embodiments Y is C; $R^1$ and $R^2$ are both H; A, E, B and D are $CH_2$; X is O; and $R^3$ is a radical of formula (ii):

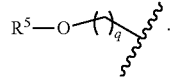

In some embodiments Y is C; $R^1$ and $R^2$ are both H; A, E, B and D are $CH_2$; X is O; and $R^3$ is a radical of formula (iii):

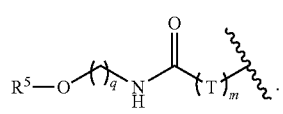

Preferably Y is C; X is O; A, B, E and D are all $CH_2$; $R^1$ is H; $R^2$ is a radical of formula (viii):

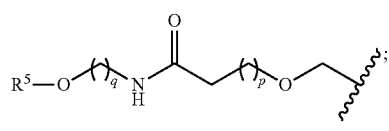

and $R^3$ is a radical of formula (ii):

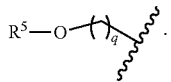
(ii)

In some embodiments Y is C; X is O; A, B, E and D are all $CH_2$; $R^1$ is H; $R^2$ is a radical of formula (ix):

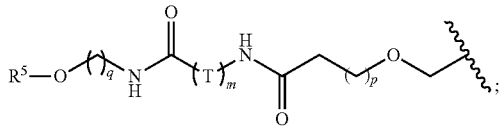
(ix)

and $R^3$ is a radical of formula (iii):

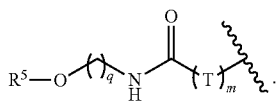
(iii)

In some embodiments Y is C; X is O; A, B, E and D are all $CH_2$; $R^1$ is H; $R^2$ is a radical of formula (ix):

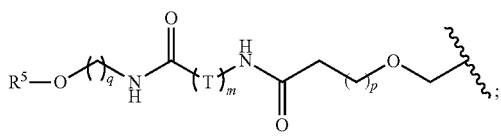
(ix)

and $R^3$ is a radical of formula (ii):

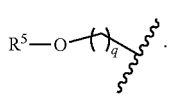
(ii)

In some embodiments Y is C; X is O; A, B, E and D are all $CH_2$; $R^1$ is H; $R^2$ is a radical of formula (viii):

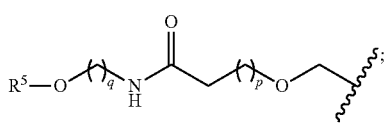
(viii)

and $R^3$ is a radical of formula (iii):

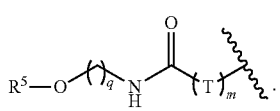
(iii)

In some embodiments Y is C; A is $(CH_2)_u$; $R^1$ and $R^2$ are both H; B, X, D and E are all absent; u is an integer from 1 to 10; and $R^3$ is a radical of formula (ii):

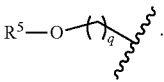
(ii)

In some embodiments Y is C; A is $(CH_2)_u$; $R^1$ and $R^2$ are both H; B, X, D and E are all absent; u is an integer from 1 to 10; and $R^3$ is a radical of formula (iii):

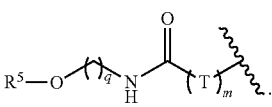
(iii)

In some embodiments Y is O; B is O; $R^1$ and $R^2$ are absent; and either A, E, D and X are all $CH_2$ or A, D and X are all $CH_2$ and E is $(CH_2CH_2O)_tCH_2$; t is an integer from 1 to 10, preferably an integer from 1 to 2; and $R^3$ is a radical of formula (ii):

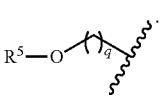
(ii)

In some embodiments Y is O; B is O; $R^1$ and $R^2$ are absent; and either A, E, D and X are all $CH_2$ or A, D and X are all $CH_2$ and E is $(CH_2CH_2O)_tCH_2$; t is an integer from 1 to 2; and $R^3$ is a radical of formula (iii):

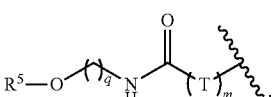
(iii)

In some embodiments p is 1.
In some embodiments q is an integer from 3 to 10, e.g. an integer from 4 to 9, e.g. an integer from 5 to 8, e.g. an integer from 6 to 7. In some preferred embodiments q is 6.
In some embodiments n is an integer from 3 to 10, e.g. an integer from 4 to 9, e.g. an integer from 5 to 8, e.g. an integer from 6 to 7. In some preferred embodiments n is 7.
In some embodiments m is an integer from 3 to 10, e.g. an integer from 4 to 9, e.g. an integer from 5 to 8, e.g. an integer from 6 to 7. In some preferred embodiments n is 7.
In some embodiments each T is $CH_2$ and q is an integer from 3 to 10, e.g. an integer from 4 to 9, e.g. an integer from 5 to 8, e.g. an integer from 6 to 7. In some preferred embodiments q is 6.
In some embodiments each T is $CH_2$ and n is an integer from 3 to 10, e.g. an integer from 4 to 9, e.g. an integer from 5 to 8, e.g. an integer from 6 to 7. In some preferred embodiments n is 7.
In some embodiments each T is $CH_2$ and q and n are each independently an integer from 3 to 10, e.g. an integer from 4 to 9, e.g. an integer from 5 to 8, e.g. an integer from 6 to 7.

In some embodiments at least one T is $CH_2$ and q is an integer from 3 to 10, e.g. an integer from 4 to 9, e.g. an integer from 5 to 8, e.g. an integer from 6 to 7. In some preferred embodiments q is 6.

In some embodiments at least one T is $CH_2$ and n is an integer from 3 to 10, e.g. an integer from 4 to 9, e.g. an integer from 5 to 8, e.g. an integer from 6 to 7. In some preferred embodiments n is 7.

In some embodiments at least one T is $(CH_2CH_2O)_x CH_2CH_2$ and x is an integer from 2 to 10, e.g. an integer from 2 to 9, e.g. an integer from 2 to 8, e.g. an integer from 2 to 7, e.g. an integer from 2 to 6, e.g. an integer from 2 to 5, e.g. an integer from 2 to 4. In some preferred embodiments x is 3.

In some embodiments at least one T is $CH_2$ and q is 6 and n is 7.

In some embodiments at least one T is $CH_2$ and p is 1 and q is 6. In some preferred embodiments at least one T is $CH_2$ and p is 1, m is 7 and q is 6.

In some embodiments the compound of formula (i) is selected from the group consisting of:

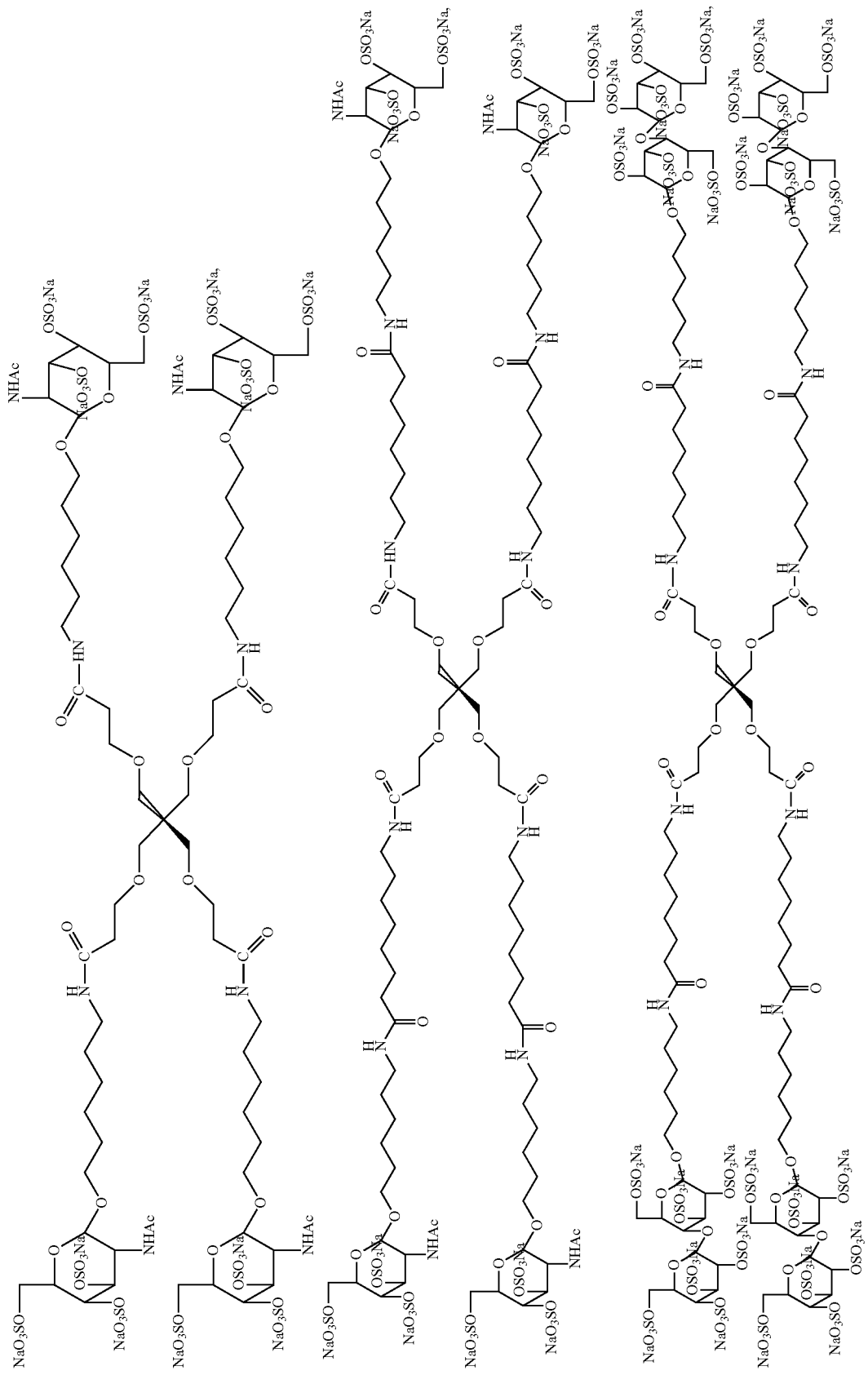

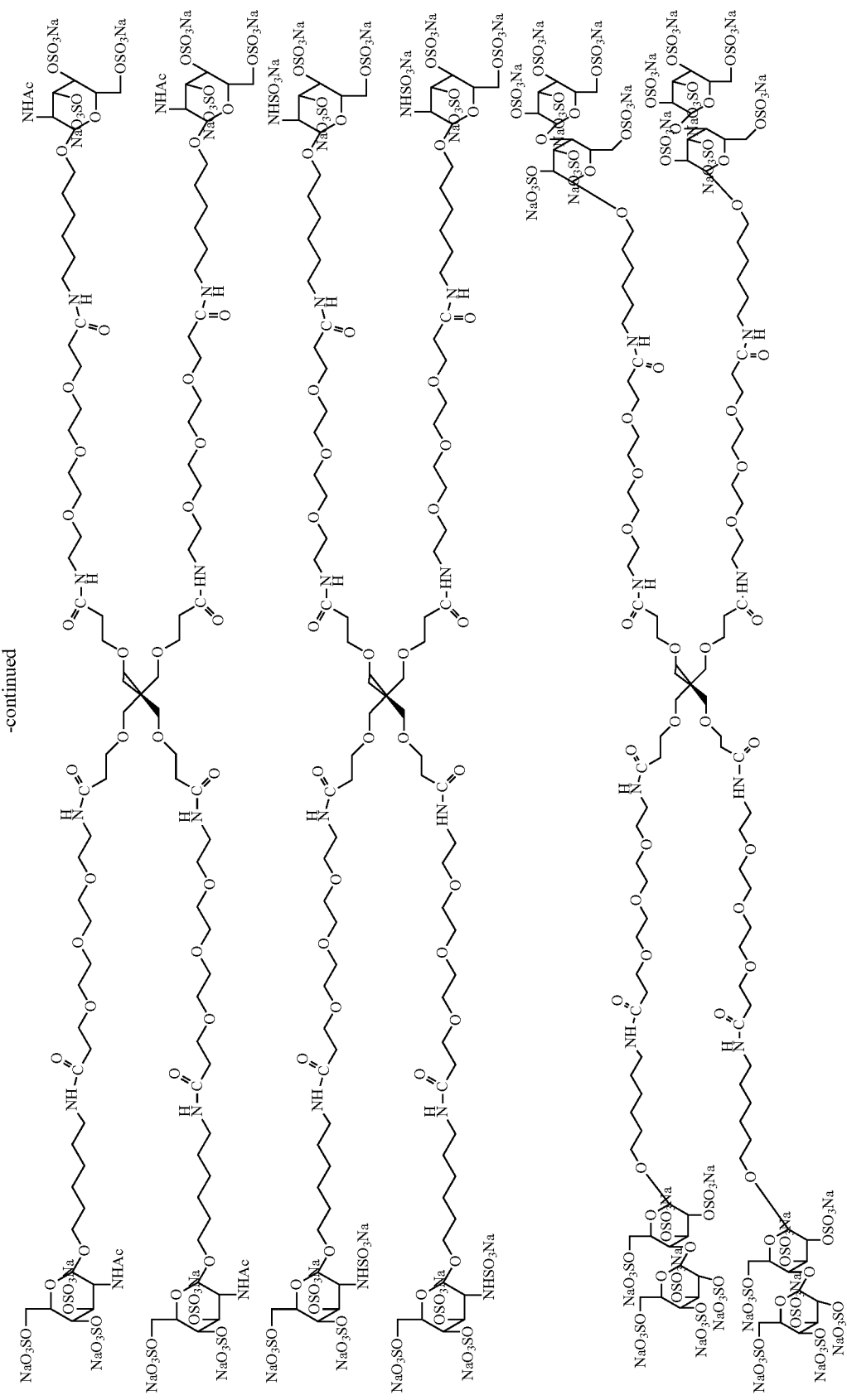

-continued
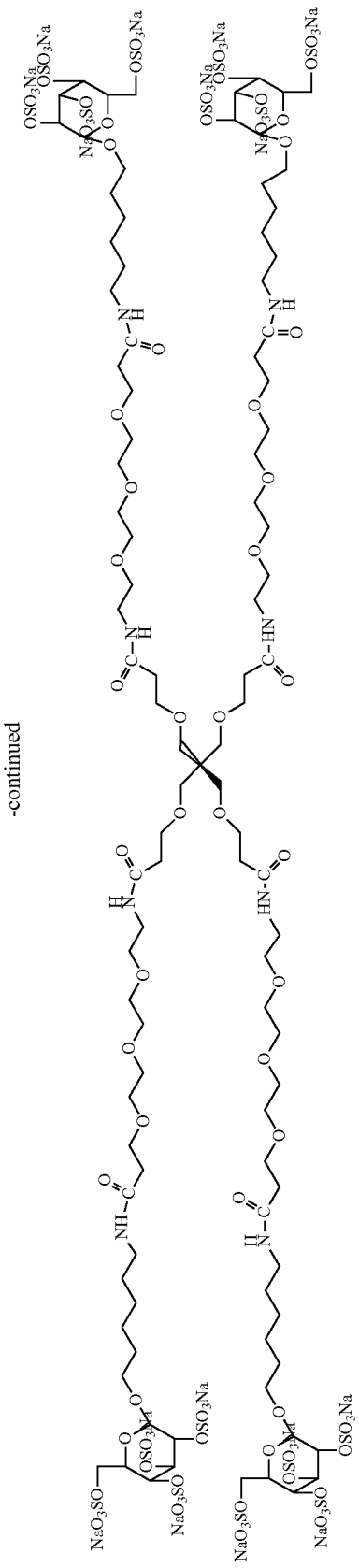
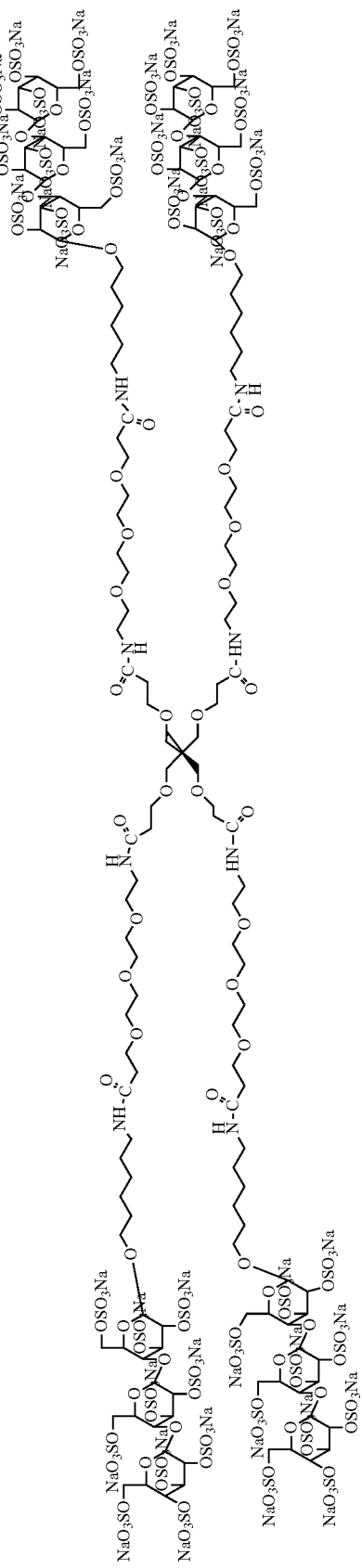

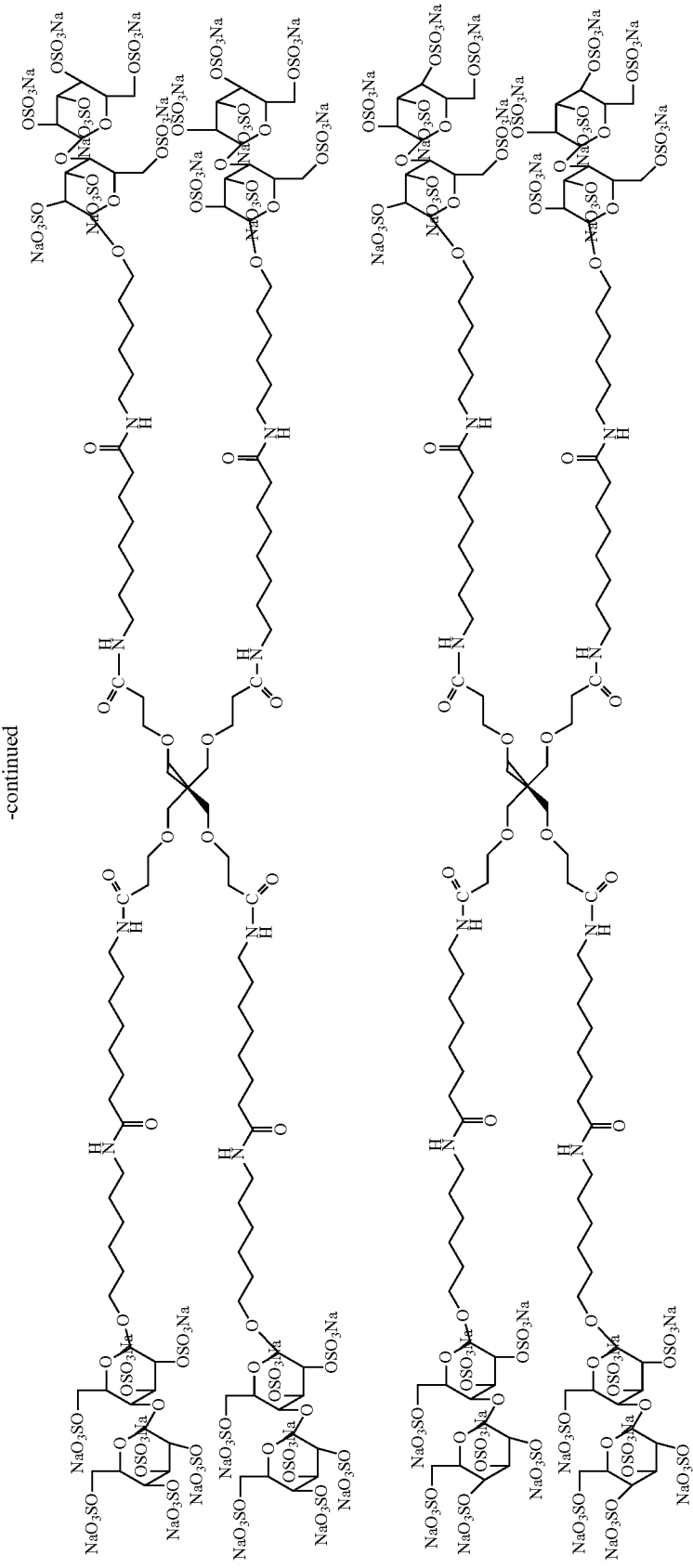

-continued
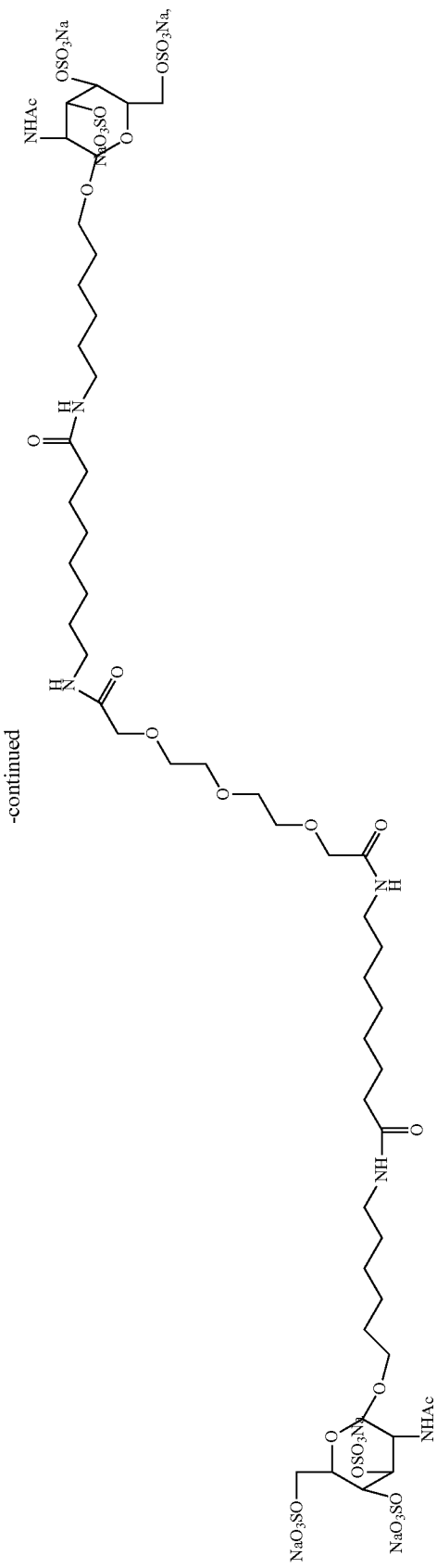
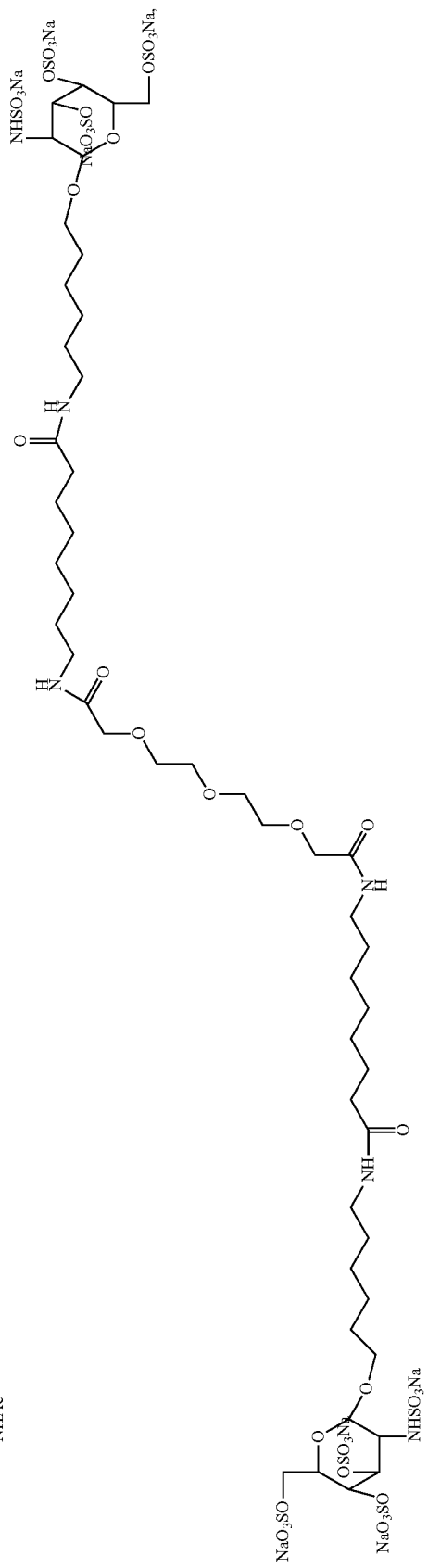

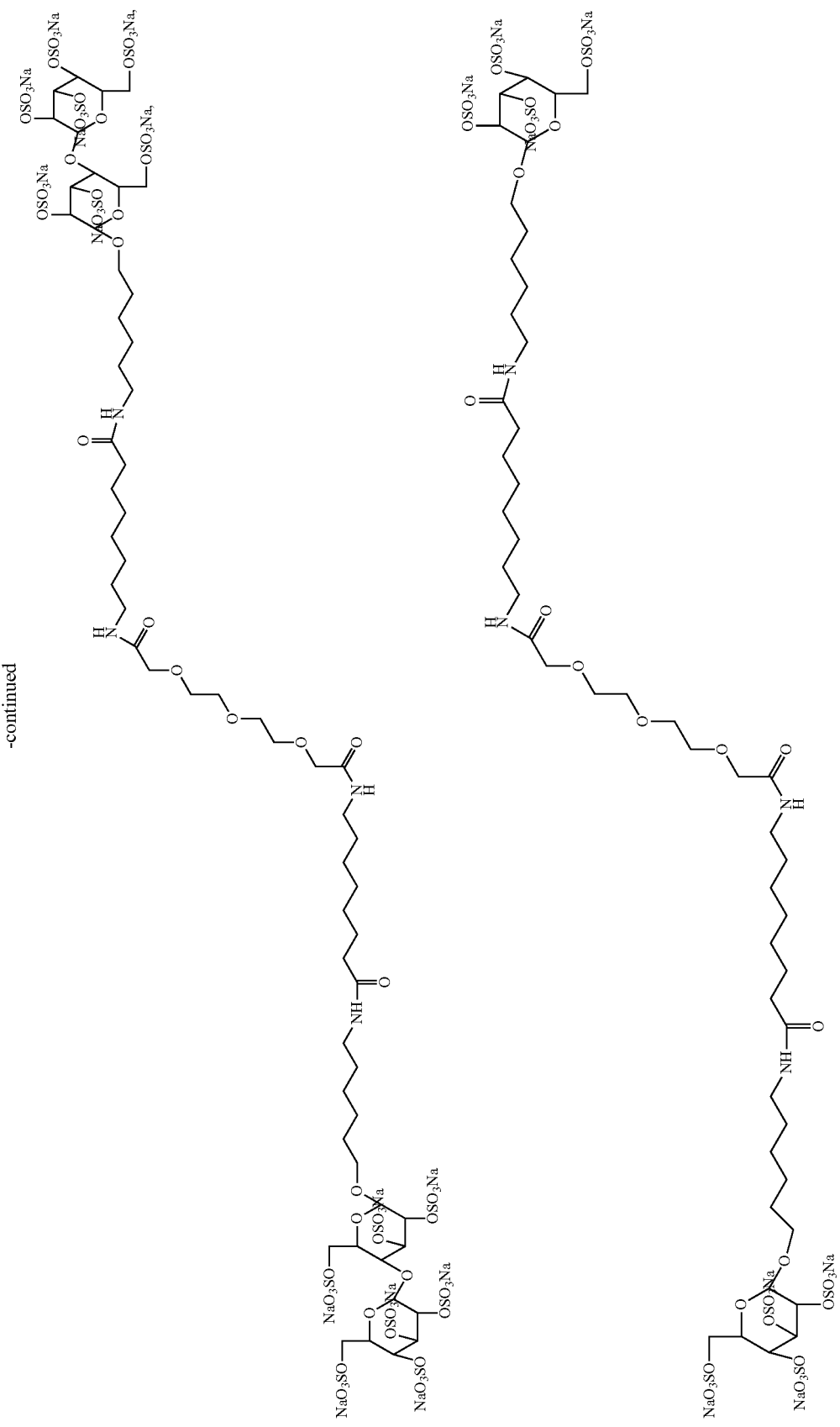

-continued
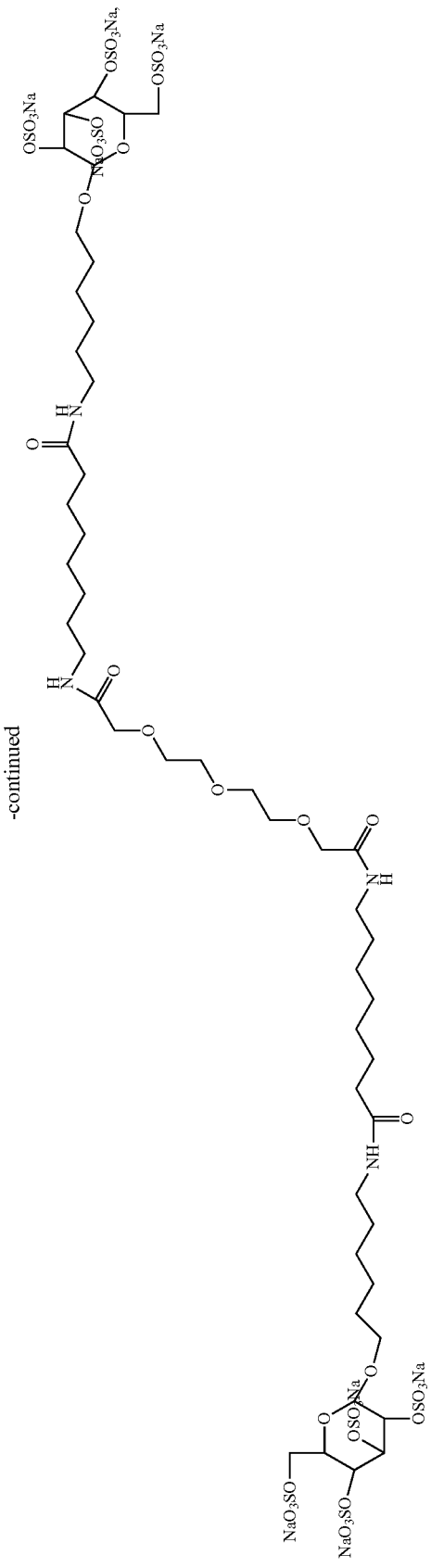
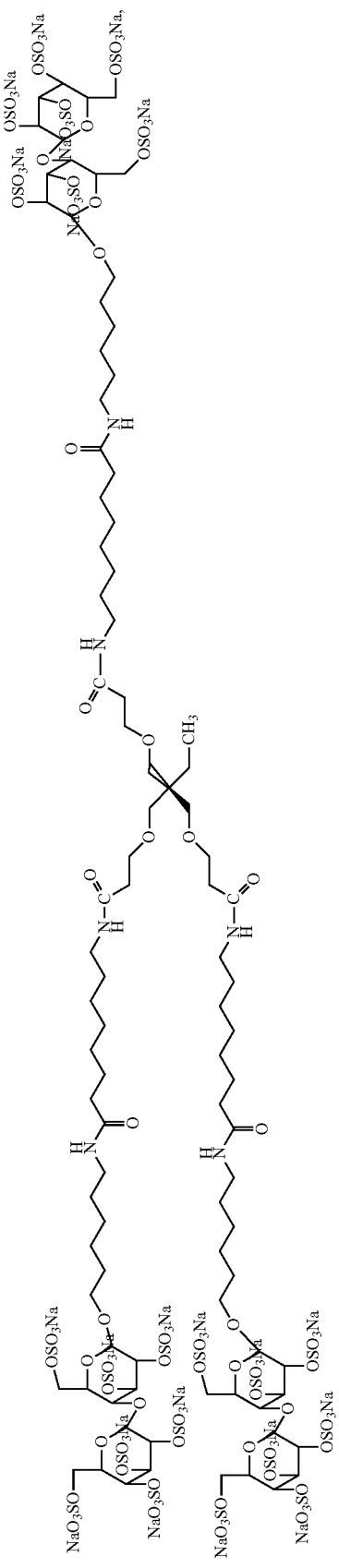

-continued
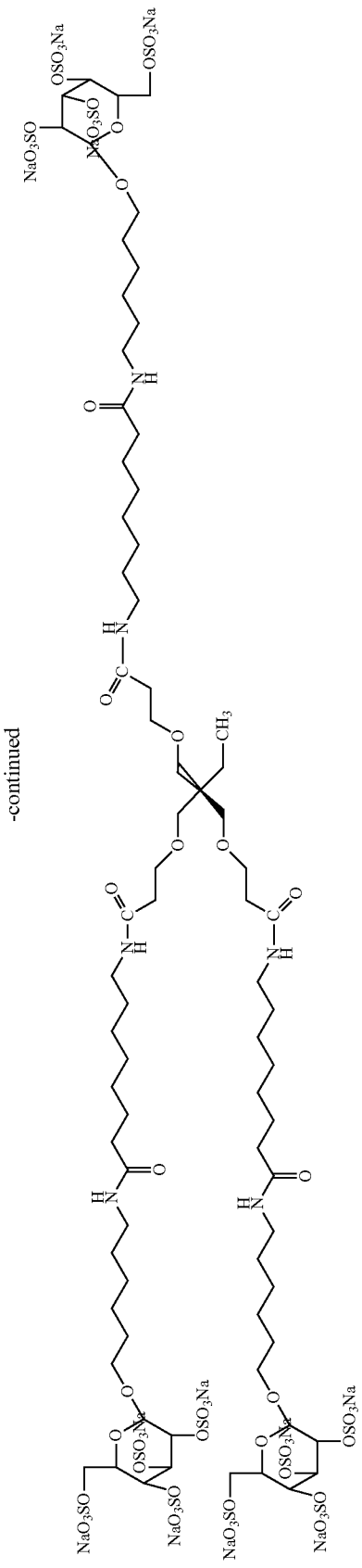

or a pharmaceutically acceptable salt thereof.

Therapeutic Uses

The compounds of the invention, particularly those exemplified, are inhibitors of heparanase and therefore have potential for the treatment or prevention of cancer, inflammation and diabetic nephropathy. Example 4 shows a range of compounds of the invention having inhibition activity against heparanase.

The compounds are also anticipated to be inhibitors of BACE-1 and may therefore be useful for the treatment or prevention of diseases or conditions in which it is desirable to lower cholesterol levels, e.g. Niemann-Pick Disease Type C (NPC), neurodegenerative disorders, senile dementia, pre-senile dementia, multi-infarct dementia or Alzheimer's disease.

In particular, Example 5 shows that compounds 17c and 25a have a positive effect on filipin (cholesterol) fluorescence in fibroblast cells derived from NPC and Alzheimer's disease patients. These compared favourably to a clinically approved histone deacetylase (HDAC) inhibitor SAHA. HDAC inhibition is identified as a potential novel and promising therapy for NPC disease.

Example 6 shows that at least one compound of the invention, compound 17c, is effective for the treatment of myeloma in mice indicating that this compound, and structurally related compounds, may have human therapeutic potential against myeloma and potentially other cancers.

Without wishing to be bound by theory, the applicants hypothesise that the compounds of the invention can achieve a "clustering effect" through the use of multiple copies of sulfated sugar fragments in each dendritic structure. Such a clustering effect is advantageous as repetition of individual subunit structures can enhance the usually weak interaction of individual subunit structures in sulfated saccharides.

Cosmeceutical Uses

In addition to the therapeutic uses referred to above, the compounds of the invention have also been identified as having potential cosmeceutical uses.

The reduction of fibrillar type I collagen is a characteristic feature of chronologically aged or "unhealthy" skin, although the destruction of existing collagen is, undoubtedly, central to the deleterious changes observed in aged skin. The failure to replace damaged collagen with newly synthesised material is also critical to the overall pathophysiology. These observations have provided the skin care industry with a strong rationale to develop topical formulations that stimulate skin to produce more collagen which in turn can slow or reverse the pathophysiology of skin aging. Example 7 shows the positive effect of several compounds of the invention on the production of collagen.

The diminution of extracellular matrix is a common event during the aging of connective tissues. Human skin fibroblasts from older donors have increased levels of collagenase mRNA and protein, relative to younger donors, whereas expression of the collagen type I and III genes decrease in an age dependent way. Replicative senescence of human skin fibroblasts appears to correlate with a loss of regulation and overexpression of collagenase activity. As a consequence of the age-related increase in dermal collagenase, skin care companies are constantly trying to develop compounds that can inhibit collagenase with the objective of boosting the content of dermal collagen which in turn provides the aesthetic appearance of "younger skin". Example 8 shows the heparanase inhibitory effect of compound 17b on the activity of bacterial collagenase type II from *Clostridium histolyticum*.

Skin aging is also associated with the loss of skin moisture. The key molecule involved in skin moisture is hyaluronan or hyaluronic acid (HA), a glycosaminoglycan (GAG) with a unique capacity to bind and retain water molecules. The synthesis of epidermal HA is influenced by the underlying dermis and is under separate controls from the synthesis of dermal HA. Progressive reduction in the size of the HA polymers in skin is a result of aging. Thus, the epidermis loses the principle molecule responsible for binding and retaining water molecules, resulting in the loss of skin moisture. In the dermis, the major age-related change is the increasing avidity of HA with tissue structures with the concomitant loss of HA extractability. This parallels the progressive cross-linking of collagen and the steady loss of collagen extractability with age. All of these age-related phenomena contribute to the apparent dehydration, atrophy and loss of elasticity that characterizes aged skin. Example 9 shows the positive effect of some compounds of the invention on the production of hyaluronan by human dermal fibroblasts.

Abnormal hyperpigmentations such as melasma, freckles and senile lentigines and other forms of melanin hyperpigmentation show satisfactory subjective improvement when treated with depigmenting agents, such as hydroquinone, ascorbic acid derivatives, kojic acid, azelaic acid, electron rich phenols, corticosteroids, retinoids and others. Among these agents, hydroquinone drugs are effective in up to 80% of users. They are often formulated with steroids because they may cause irritation and dermatitis. There is therefore a constant search for safe compounds that can reduce skin pigmentation. The rate-limiting steps of mammalian melanin synthesis are regulated by tyrosinase, which catalyses the conversions of L-tyrosine to L-dopa and L-dopa to L-dopa-quinone. Therefore, determining the effect of a compound on tyrosinase activity could provide a strong indicator of its ability to act as a "skin whitening" component. Example 10 shows a significant inhibitory effect on tyrosinase activity at least for compounds 17c and 17d.

Example 11 shows that several compounds 17c and 17d are also effective inhibitors of testicular hyaluronidase.

Formulations and Administration

The compounds of the invention may be administered to a patient by a variety of routes, including orally, parenterally, by inhalation spray, topically, rectally, nasally, buccally or via an implanted reservoir. The compounds may also be administered by intracerebral, intracerebroventricular or intrathecal delivery. For parenteral administration, injections may be given intravenously, intra-arterially, intramuscularly or subcutaneously.

The amount of a compound of the invention to be administered to a patient will vary widely according to the nature of the patient and the nature and extent of the disorder to be treated. Typically the dosage for an adult human will be in the range of about 0.01 µg/kg to about 1 g/kg, preferably about 0.01 mg/kg to about 100 mg/kg. The specific dosage required for any particular patient will depend upon a variety of factors, such as the patient's age, body weight, general health, gender and diet. Optimal doses will depend on other factors such as mode of administration and level of progression of the disease or disorder. Doses may be given once daily, or two or more doses may be required per day. For example, a dosage regime for an Alzheimer's patient might require one dose in the morning and one in the evening. Alternatively, a dosage regime for such a patient might require four hourly doses.

For oral administration the compounds can be formulated into solid or liquid preparations, for example tablets, capsules, granules, powders, solutions, suspensions, syrups, elixirs and dispersions. Such preparations are well known in the art as are other oral dosage regimes not listed here.

For parenteral administration, compounds of the invention can be formulated into sterile solutions, emulsions and suspension.

Compounds of the invention may be mixed with suitable vehicle and then compressed into the desired shape and size. The compounds may be tableted with conventional tablet bases such as lactose, sucrose and cornstarch, together with a binder, a disintegration agent and a lubricant. The binder may be, for example, cornstarch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added. Tablets, capsules or powders for oral administration may contain up to about 99% of a compound of the invention.

When liquid preparations are required for oral use, a compound of the invention may be combined with a pharmaceutically acceptable carriers such as water, an organic solvent such as ethanol, or a mixture of both, and optionally other additives such as emulsifying agents, suspending agents, buffers, preservatives, and/or surfactants may be used. Colourings, sweeteners or flavourings may also be added.

The compounds may also be administered by injection in a pharmaceutically acceptable diluent such as water or saline. The diluent may comprise one or more other ingredients such as ethanol, propylene glycol, an oil or a pharmaceutically acceptable surfactant.

The compounds of the invention may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds of the invention may further be administered by means of sustained release systems. For example, they may be incorporated into a slowly dissolving tablet or capsule.

Synthesis of the Compounds of the Invention

The compounds of the invention may be prepared by a variety of different methods. The following are representative non-limiting general methods for synthesising compounds of the invention.

1. Synthesis of the Dendritic "Core" Starting Materials

The "cores" that are used as starting materials for the dendritic compounds of the invention can be synthesised according to the methods described in WO 2014/084744. See, for example, Scheme 1.

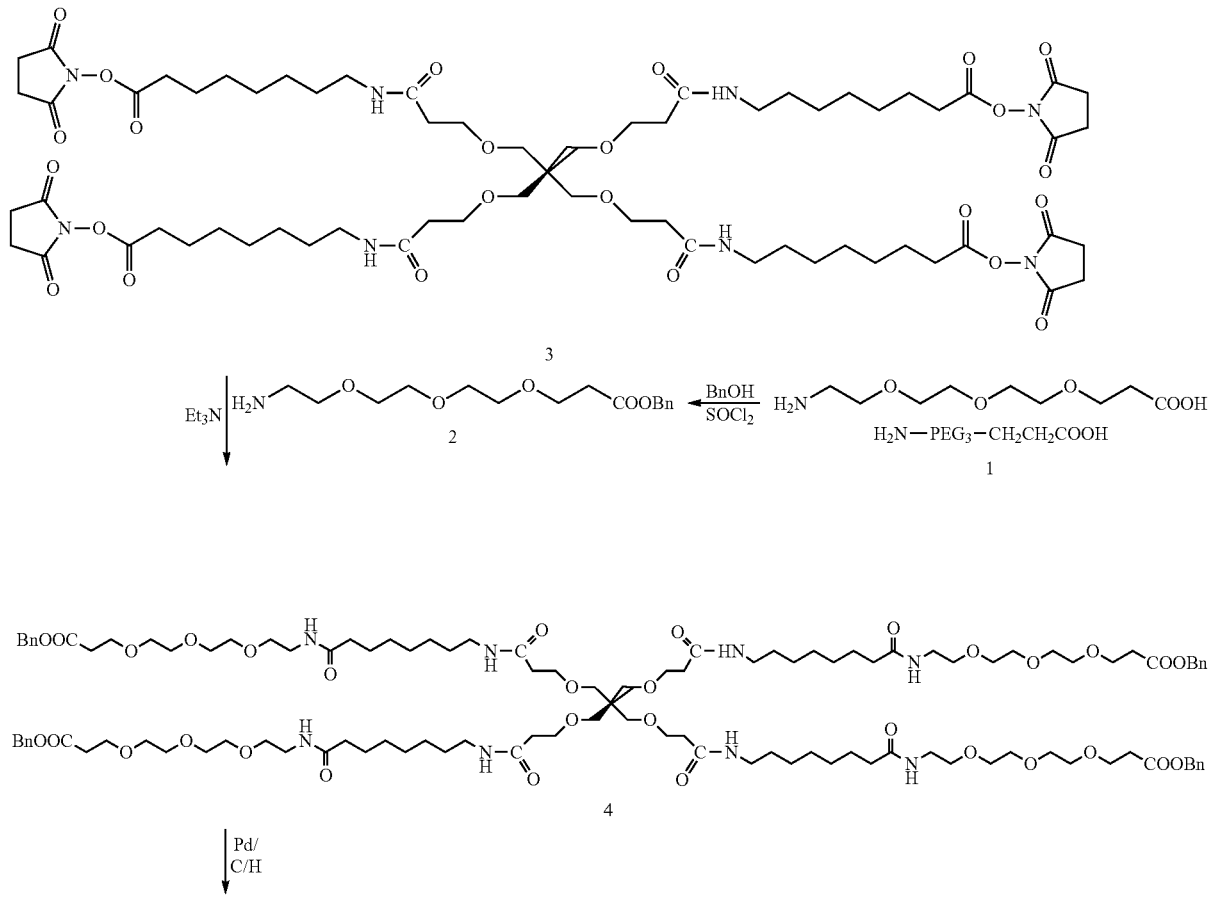

-continued

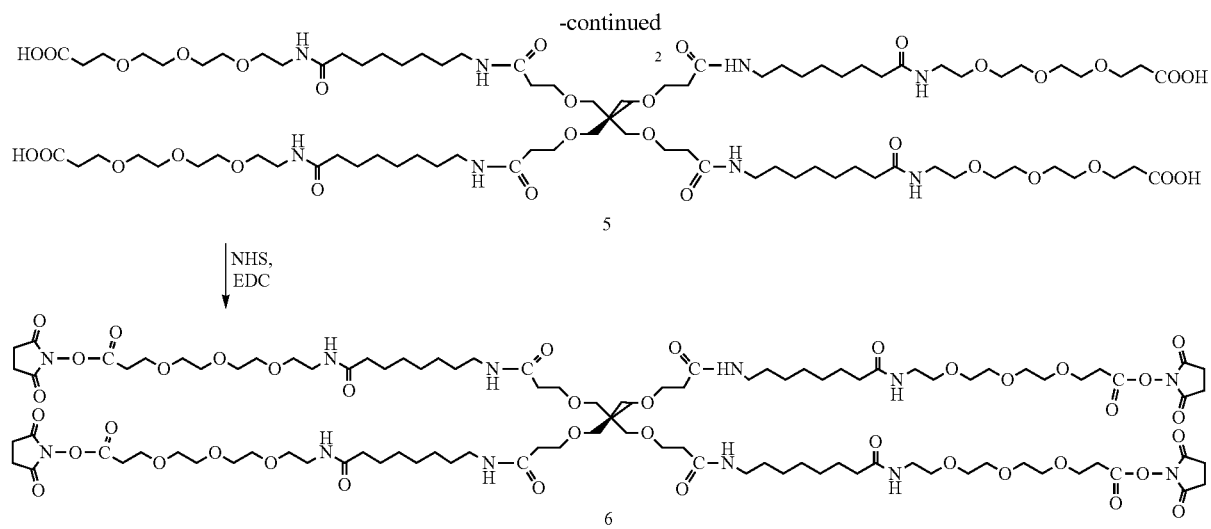

2. Synthesis of the Glycoside Units

The mono-, di- and trisaccharide units used as or used to prepare the glycosides that can be coupled to the core starting materials can be synthesised as described in WO 2012/121617.

Scheme 2 shows a general method for the synthesis of glycosides that can be used to prepare tetrameric, trimeric and dimeric compounds of the invention.

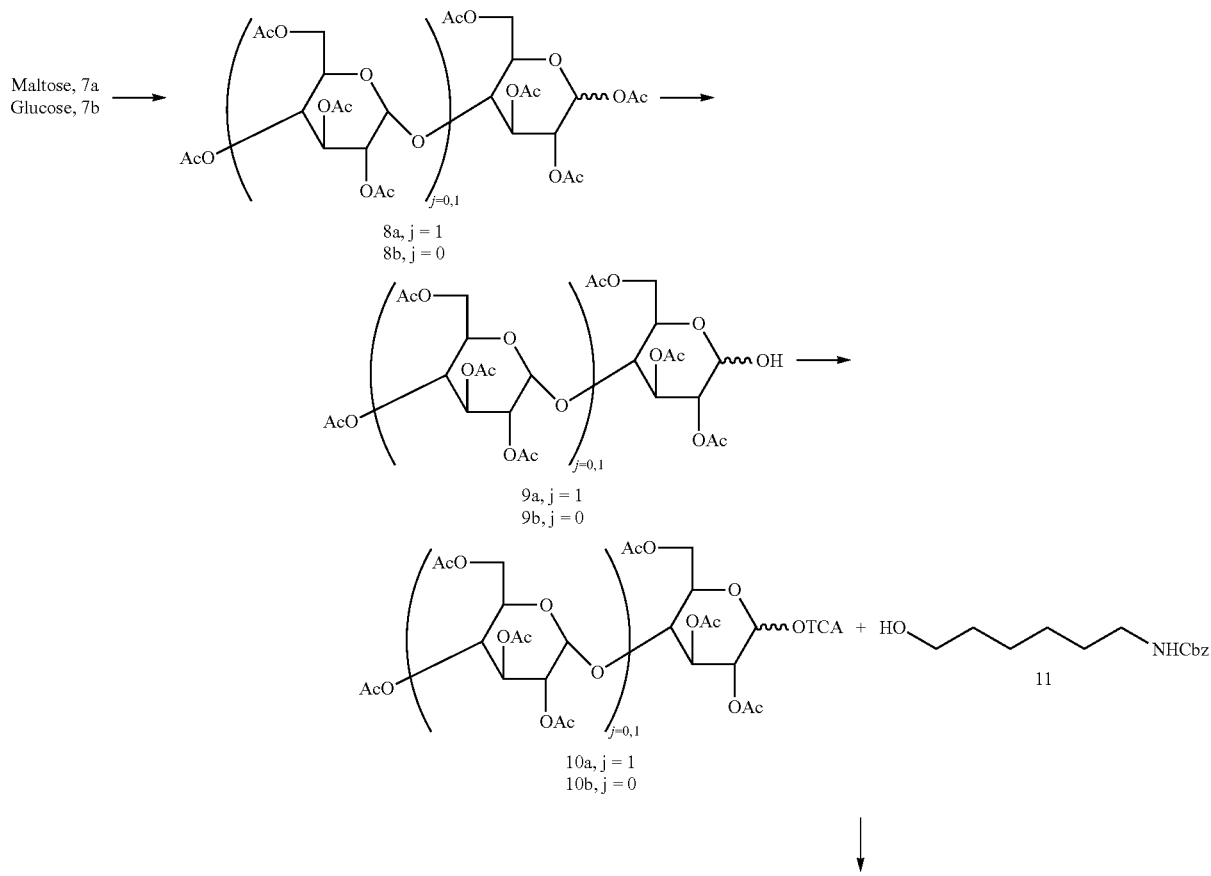

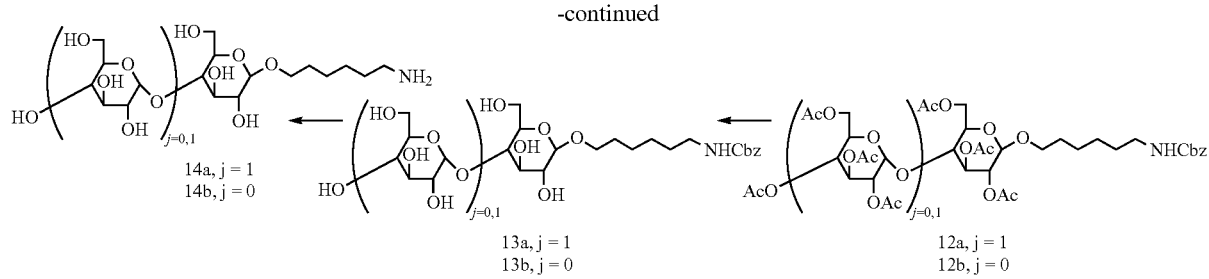

14a, j = 1
14b, j = 0

13a, j = 1
13b, j = 0

12a, j = 1
12b, j = 0

3. Synthesis of the Dendritic Compounds of the Invention

The "core" starting materials can be coupled to a glycoside which has a free amino group, thereby allowing preparation of the dendritic compounds of the invention. The coupling procedure requires a suitable solvent (e.g. DMF, DMSO, water), a small amount of base (e.g. triethylamine), and a suitable glycoside. At least about 2 equivalents of glycoside (e.g. about 2.2 equivalents) are used for coupling with dimeric cores. At least about 3 equivalents of glycoside (e.g. about 3.3 equivalents) are used for coupling with trimeric cores. At least about 4 equivalents of glycoside (e.g. about 4.4 equivalents) are used for coupling with tetrameric cores.

Schemes 3 to 6 show general methods for coupling glycosides to the tetrameric, trimeric and dimeric cores.

Scheme 3

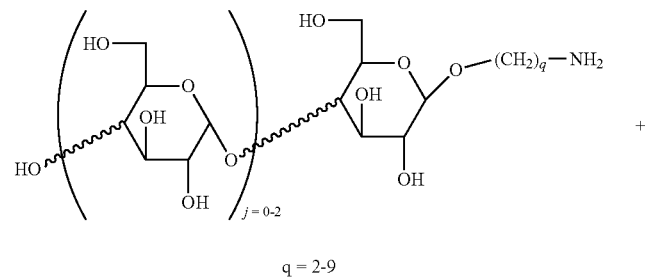

q = 2-9

14a (Gluco-gluco, j = 1, q = 6);
14b (Gluco-, j = 0, q = 6)

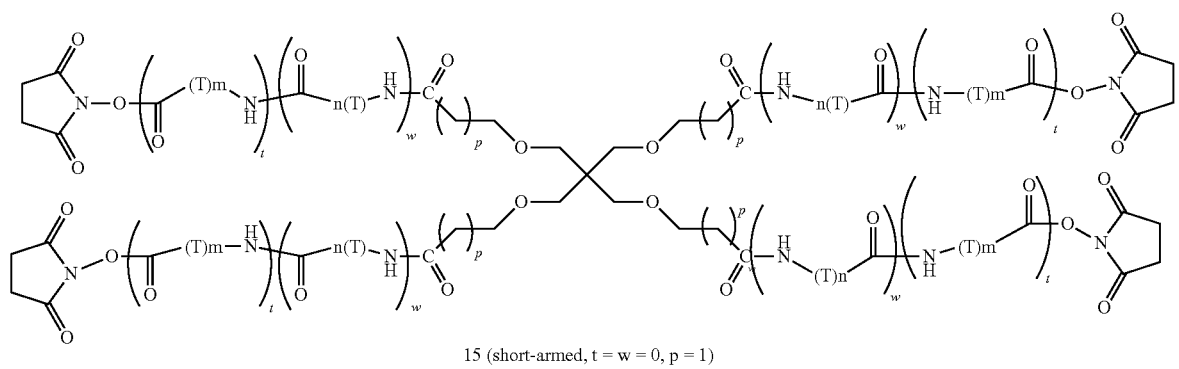

15 (short-armed, t = w = 0, p = 1)
3 (long-armed, t = 0 or 1, w = 1, p = 1, n = 7)

$\downarrow$ Et$_3$N, DMF

-continued
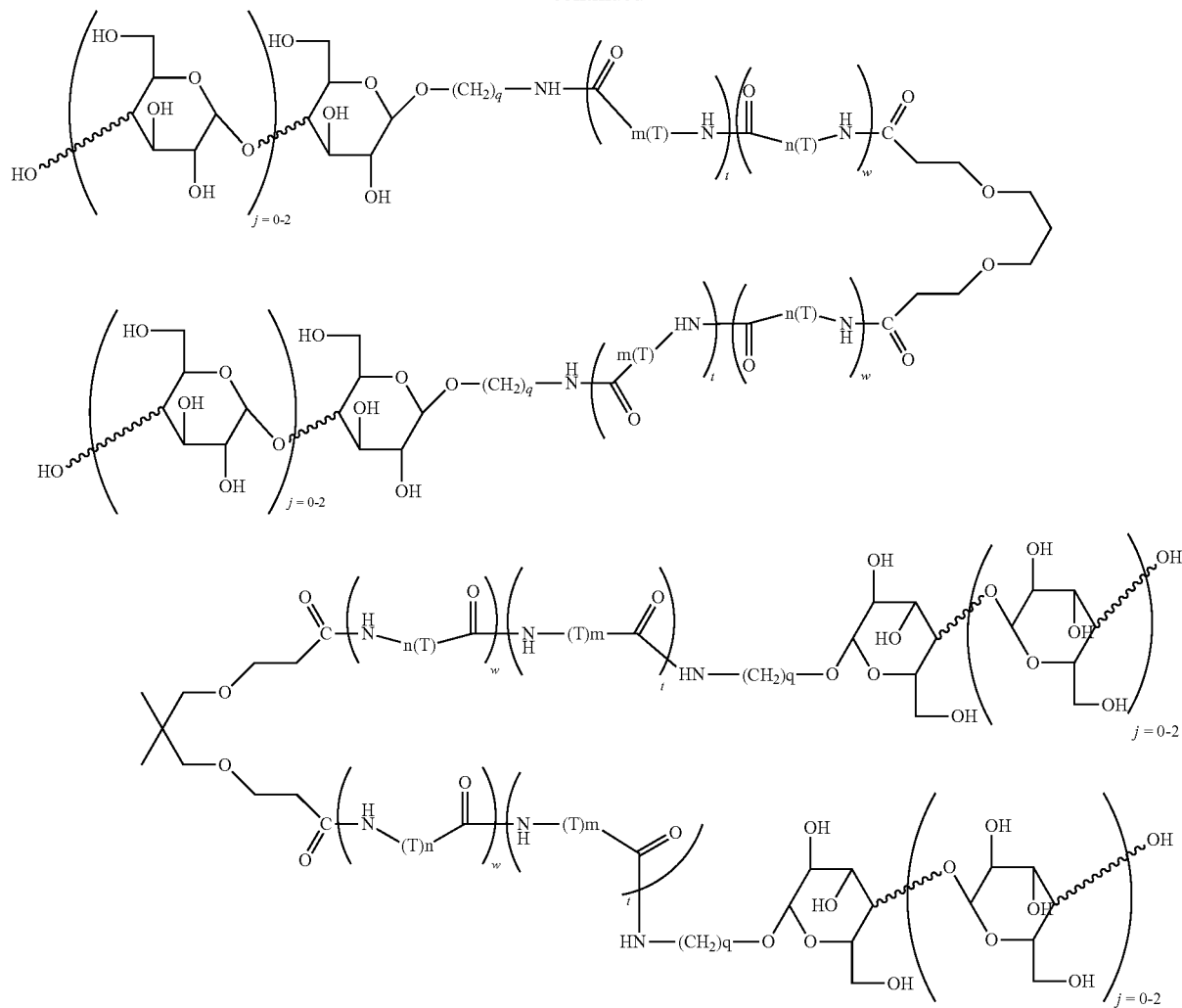
16a (short-armed, Gluco-gluco, j =1);
16b (short-armed, Gluco-, j = 0);
16c (PET core, Gluco-gluco, j = 1);
16d (PET core, Gluco-, j = 0)
↓ SO₃, NMe₃, DMF
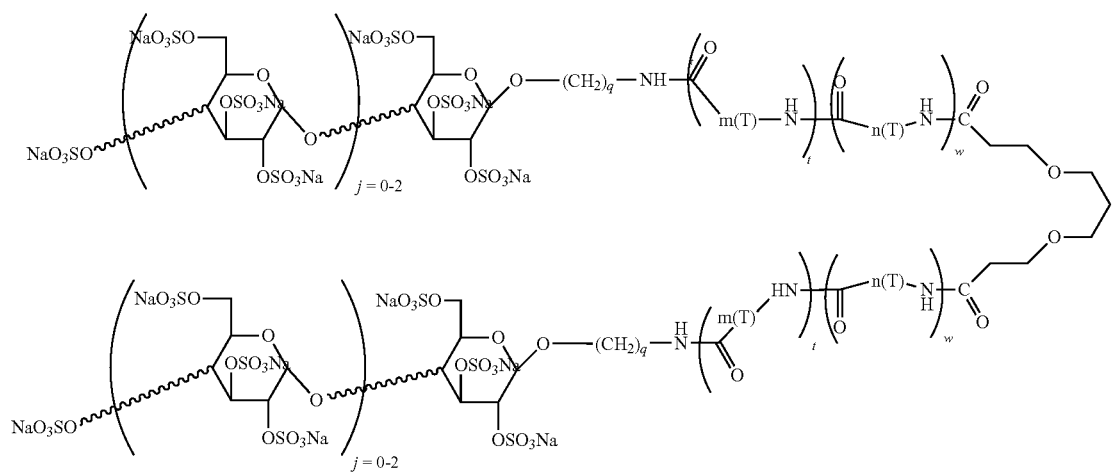

-continued
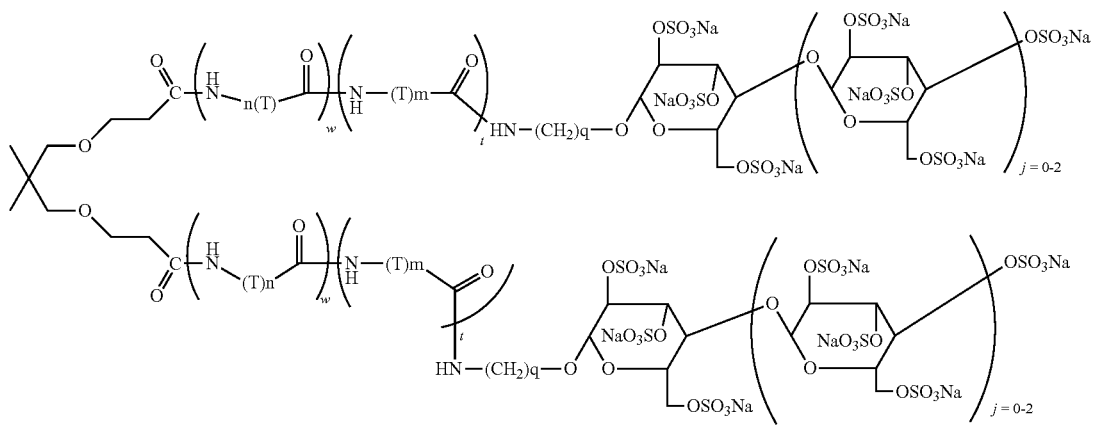
17a (short-armed, Gluco-gluco, j = 1);
17b (short-armed Gluco-, j = 0);
17c (PET core, Gluco-gluco, j = 1);
17d (PET core, Gluco-, j = 0)
For all compound in this reaction scheme:
if short-armed, t = w = 0, p = 1, q = 6;
if long-armed, t = 0 or 1, w = 1, p = 1, n = 7, q = 6
Scheme 4
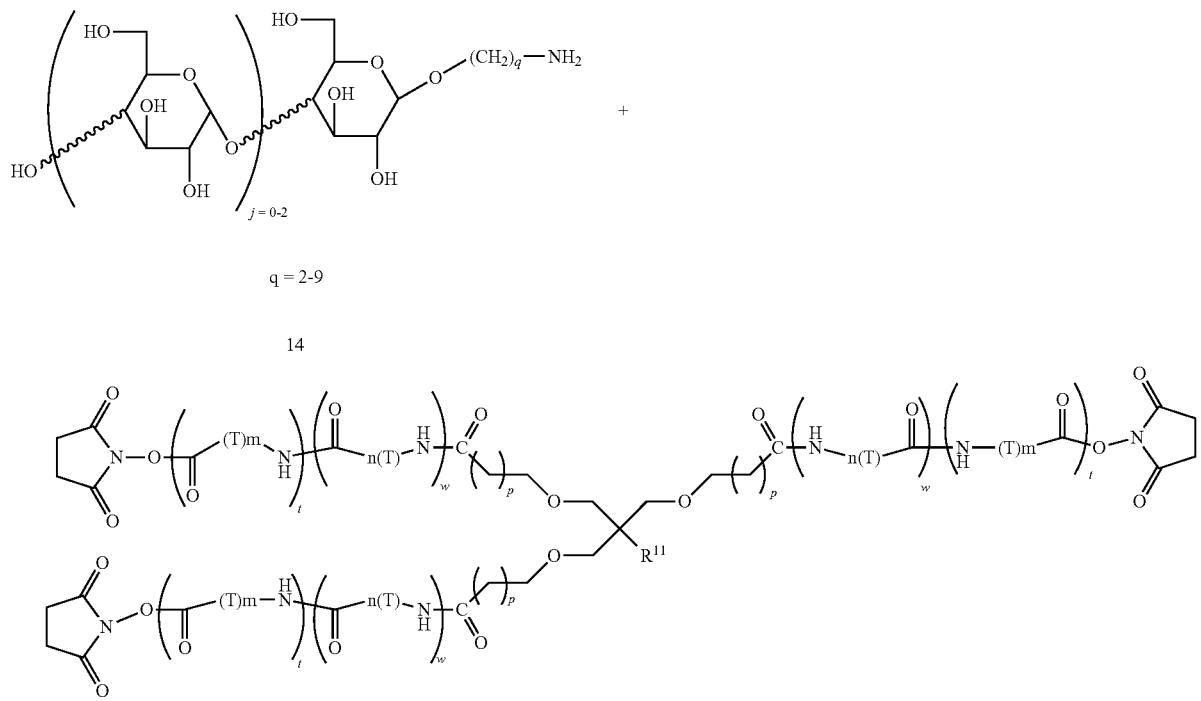
q = 2-9
14
18
$R^{11}$ = NHZ, H, $C_{1-6}$ alkyl
m = 2-11;
n = 2-11.
↓ $Et_3N$, DMF

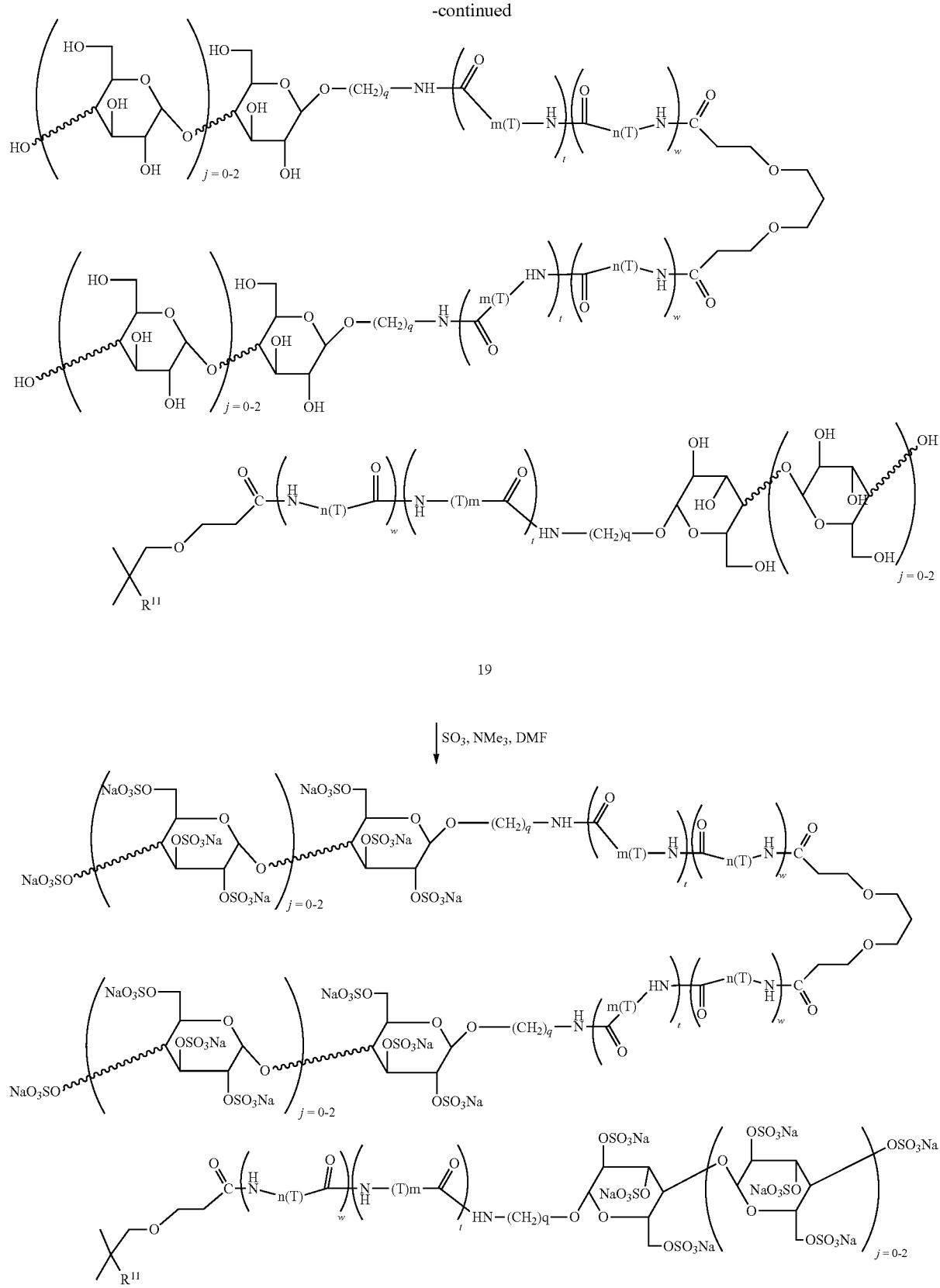

Scheme 5
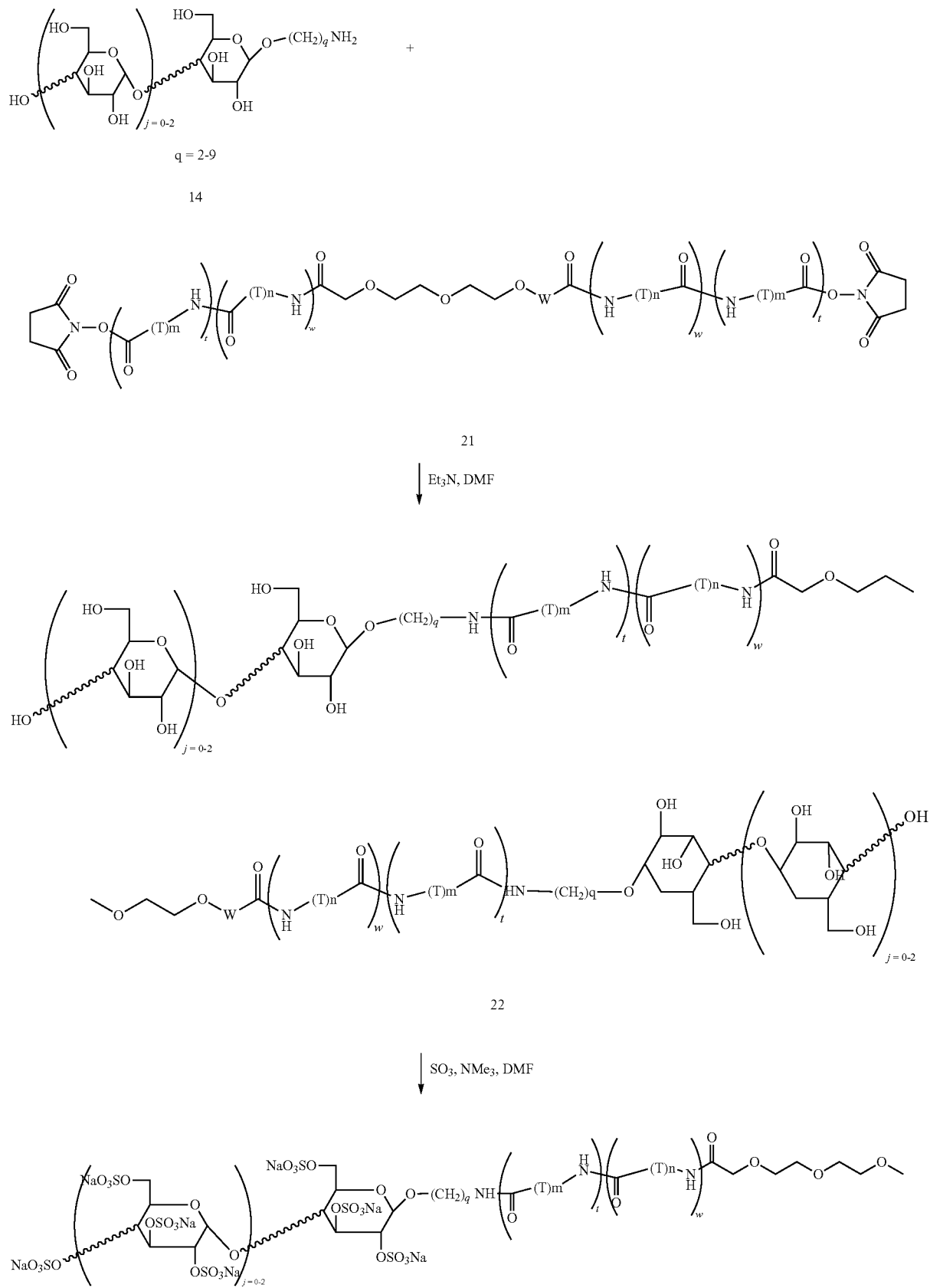

-continued
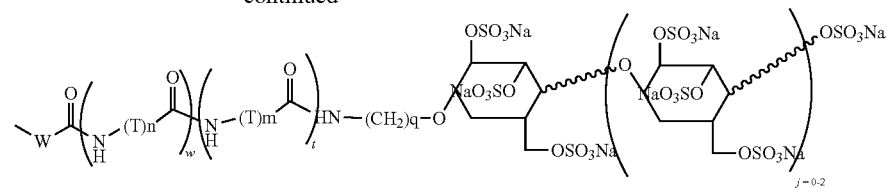
23
Scheme 6
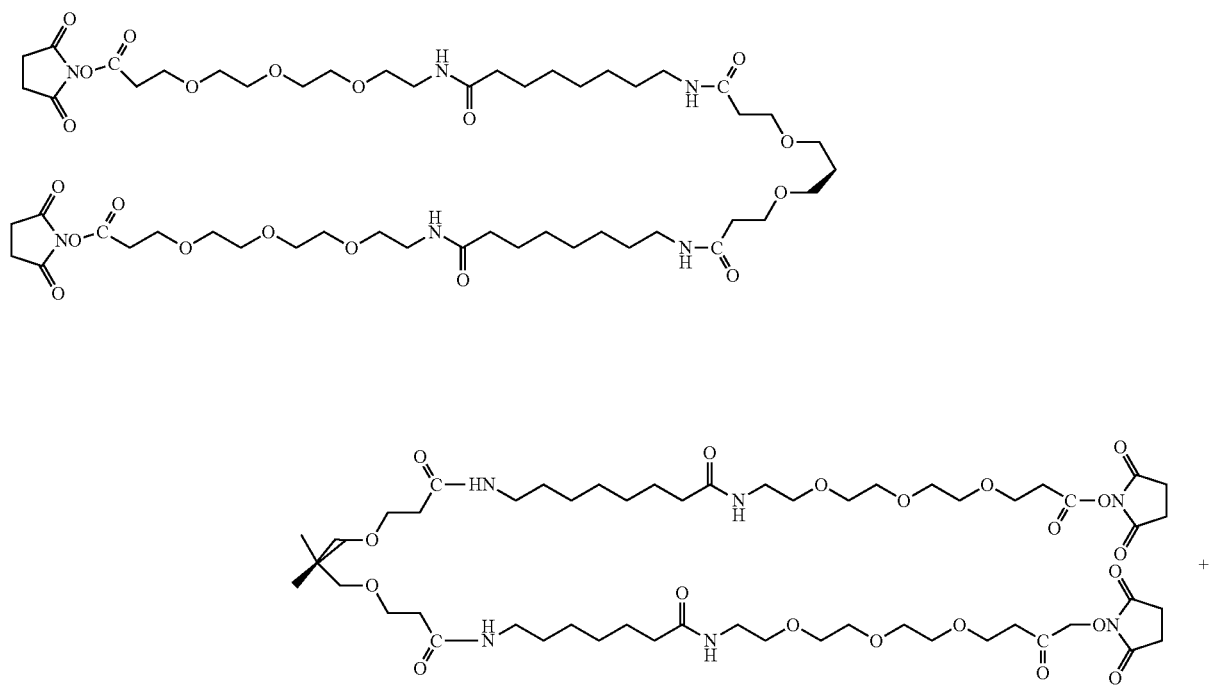
14a, j = 1
14b, j = 0
DMF, Et₃N, RT ↓

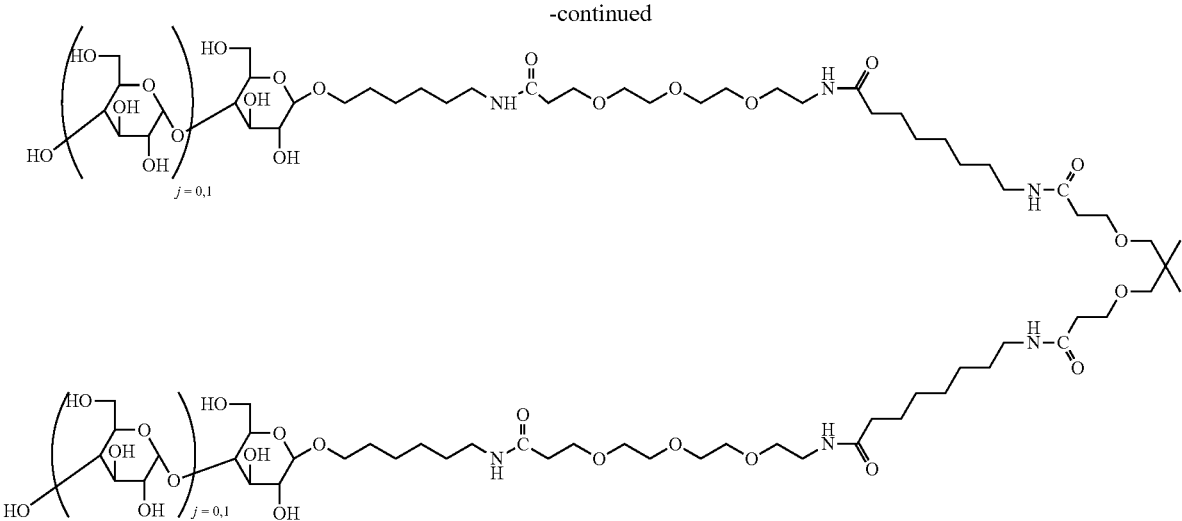
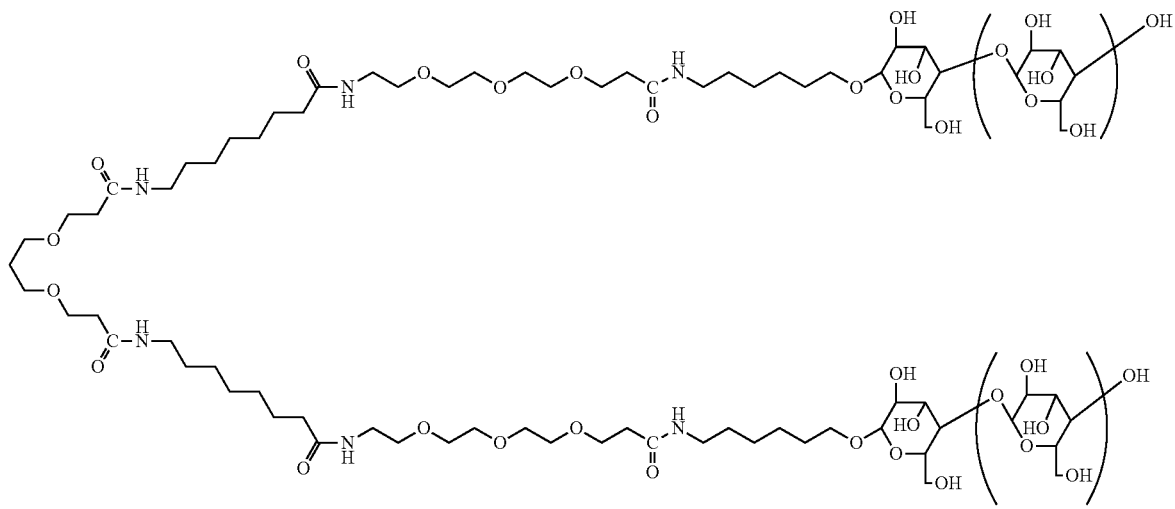
24a (Gluco-gluco, j = 1);
24b (Gluco-, j = 0)
SO$_3$•NMe$_3$ (140 eq),
DMF, Ar, 60 C.

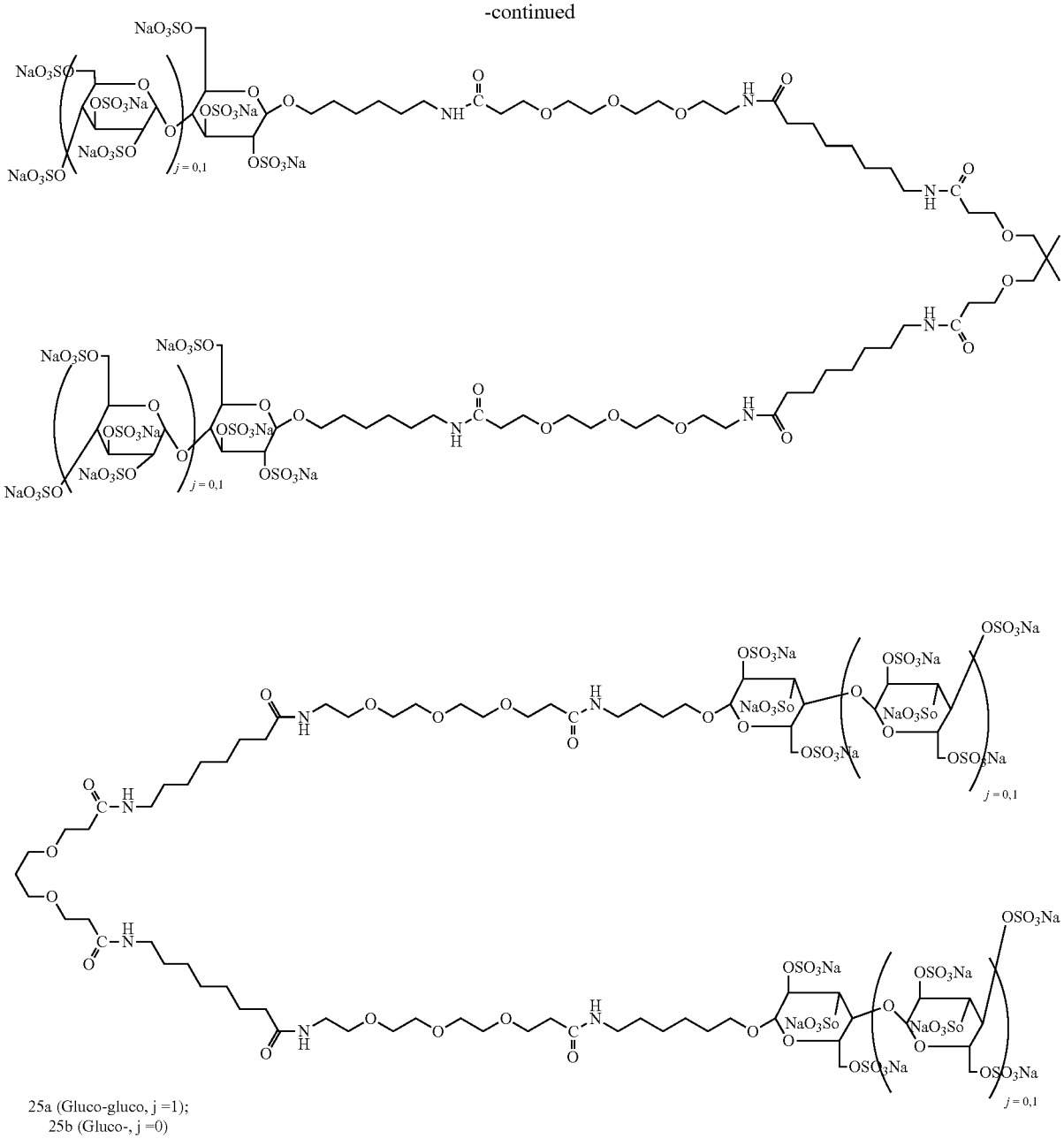

25a (Gluco-gluco, j =1);
25b (Gluco-, j =0)

EXAMPLES

The following examples further illustrate the invention. It is to be appreciated that the invention is not limited to the examples.

Abbreviations

NMR nuclear magnetic resonance
HRMS high resolution mass spectrometry
ESI electrospray ionisation
TLC thin layer chromatography
RT room temperature
DCM dichloromethane
TEMPO 2,2,6,6-tetramethyl piperidinyloxy
THF tetrahydrofuran
DMF dimethylformamide
TMS trimethylsilyl
TMS-diazomethane trimethylsilyl-diazomethane
NHS N-hydroxysuccinimide
EDC 1-ethyl-3-[3-dimethylaminopropyl]carbodiimide hydrochloride
TCA trichloroacetic acid
DABCO 1,4-diazabicyclo[2.2.2]octane
BAIB [bis(acetoxy)iodo]benzene

Example 1: Synthesis of Tetra-Succinimidyl Ester

The synthesis of the tetra-succinimidyl esters, according to Scheme 7 below, is described in WO 2014/084744.

Scheme 7
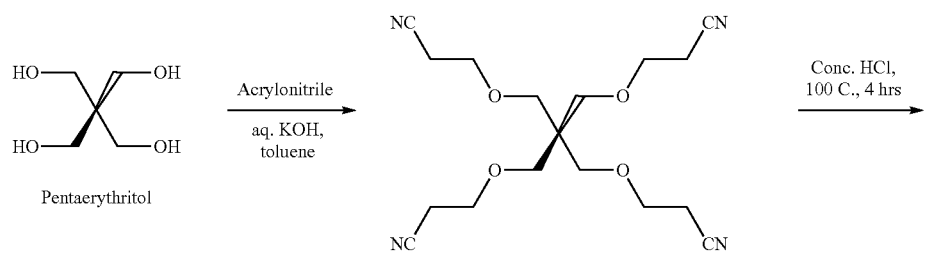
(A) Ref. 1
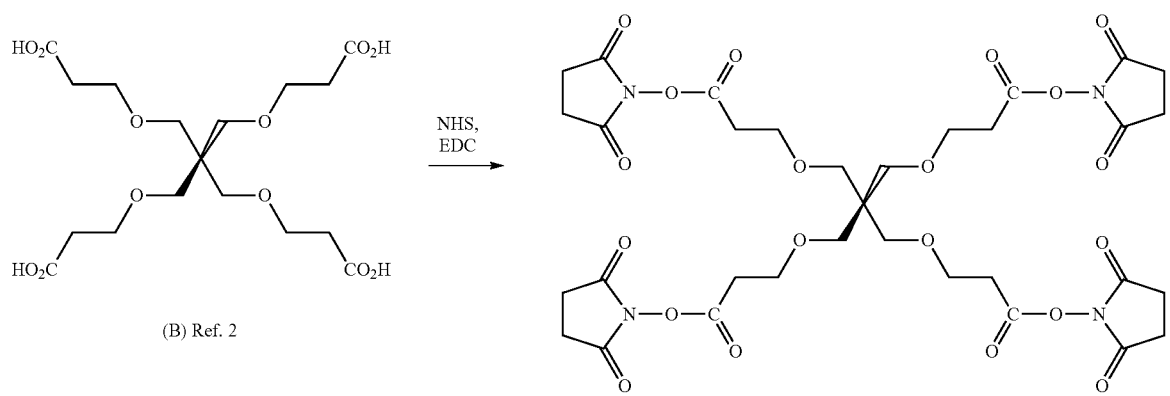
(B) Ref. 2
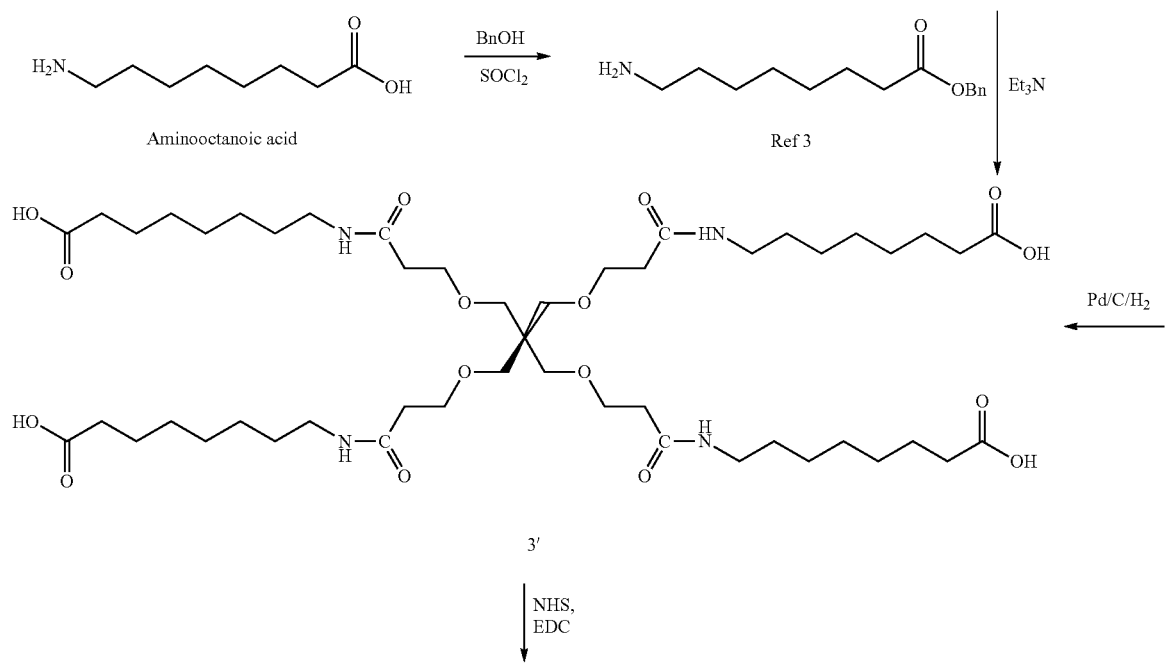

63 64
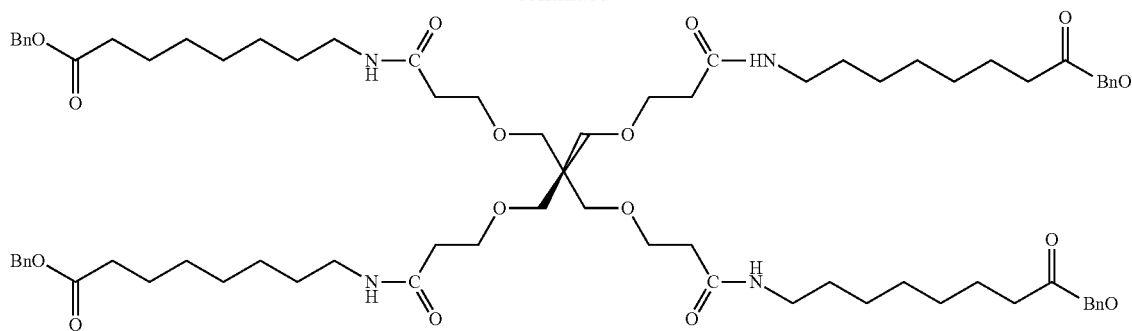
2'
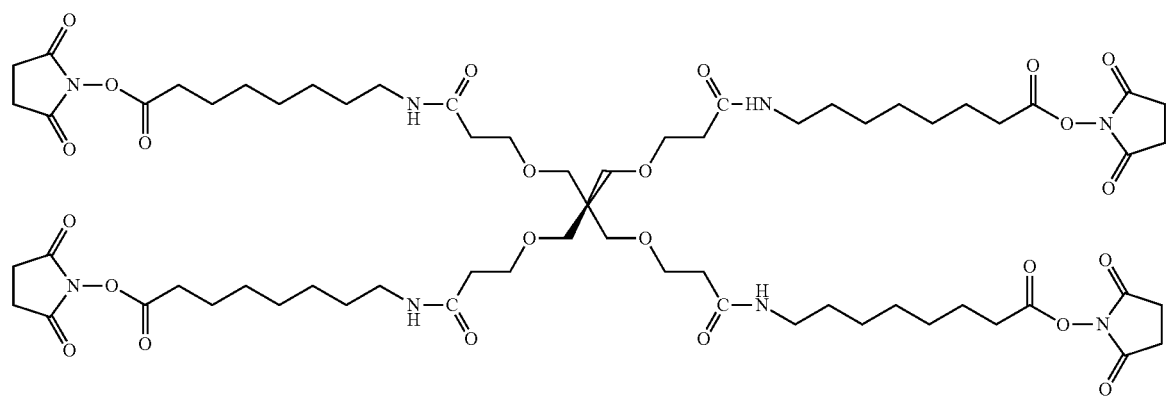
3
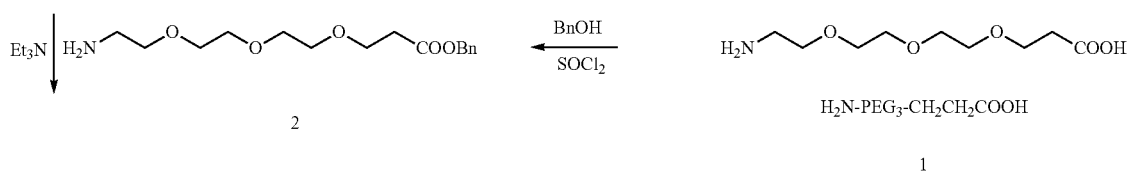
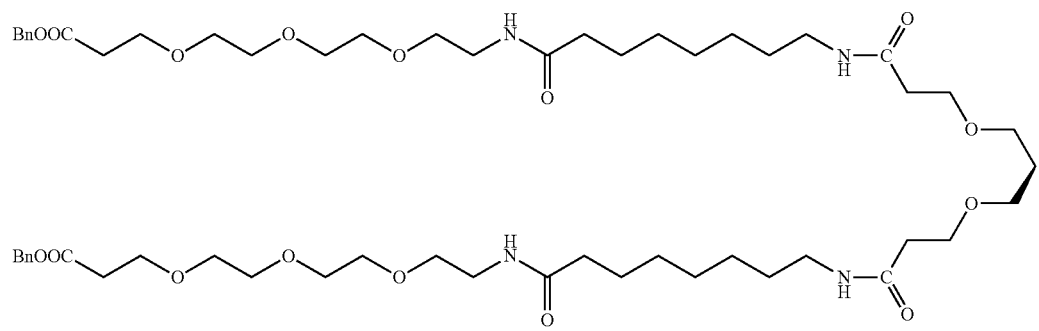

65 66
-continued
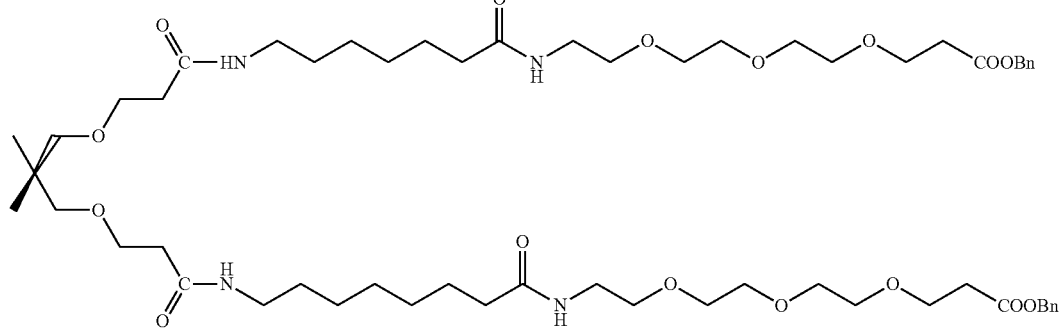
4
↓ Pd/C/H₂
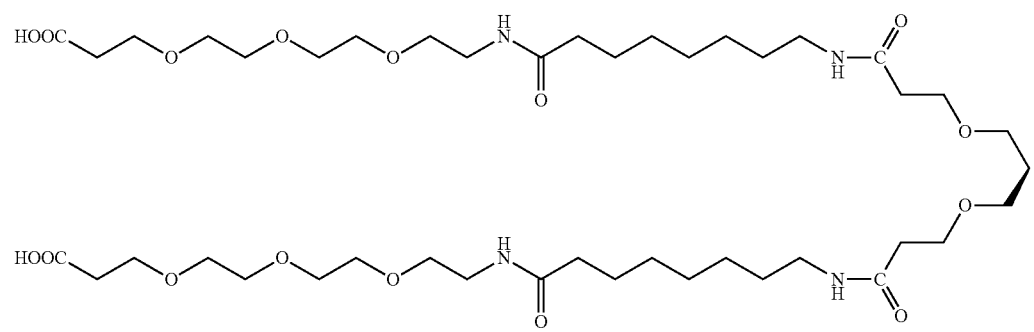
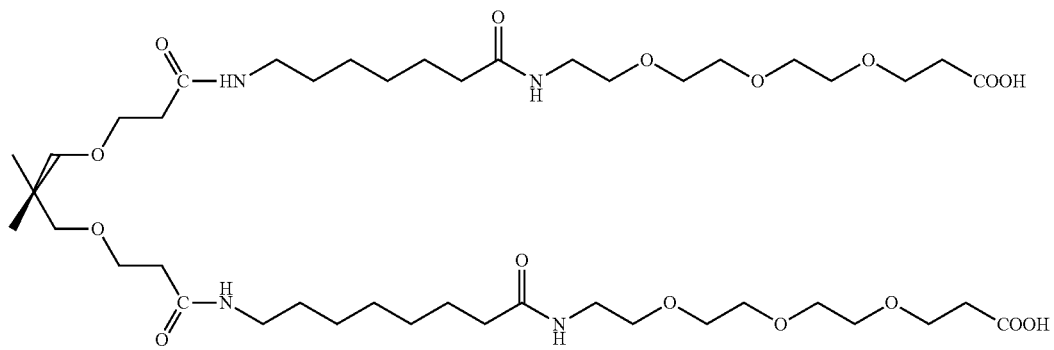
5
↓ NHS, EDC

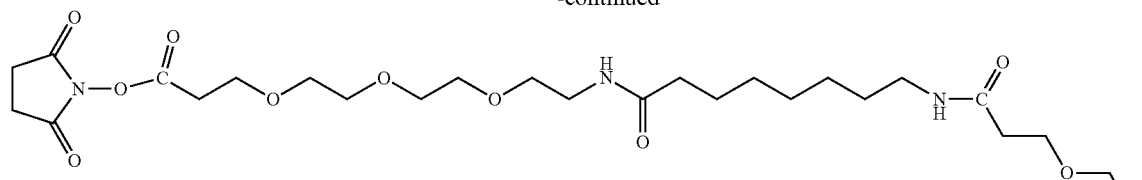
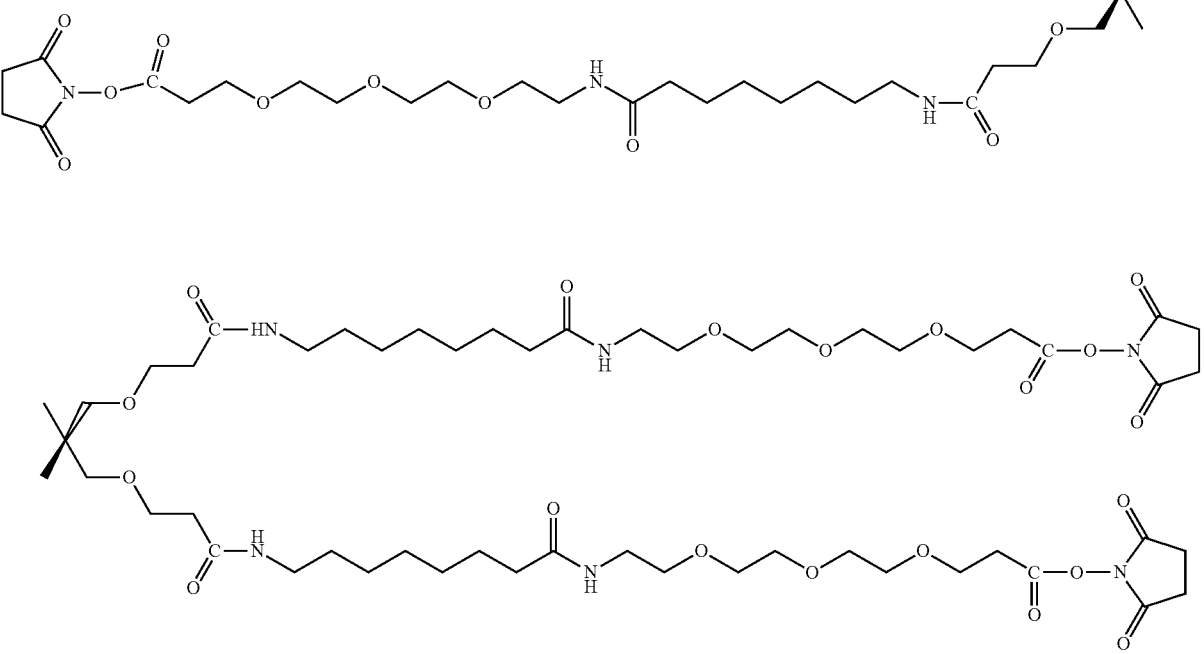
6
Example 2: Synthesis of Di-Succinimidyl Ester
The synthesis of the di-succinimidyl ester 30, according to Scheme 8 below, is described in WO 2014/084744.
Scheme 8
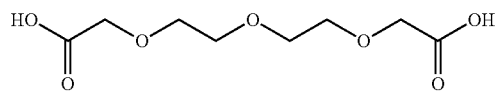
26
↓ NHS, EDC
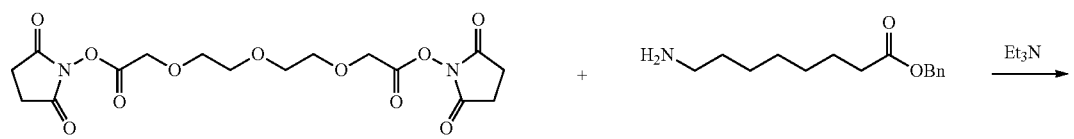
27

-continued
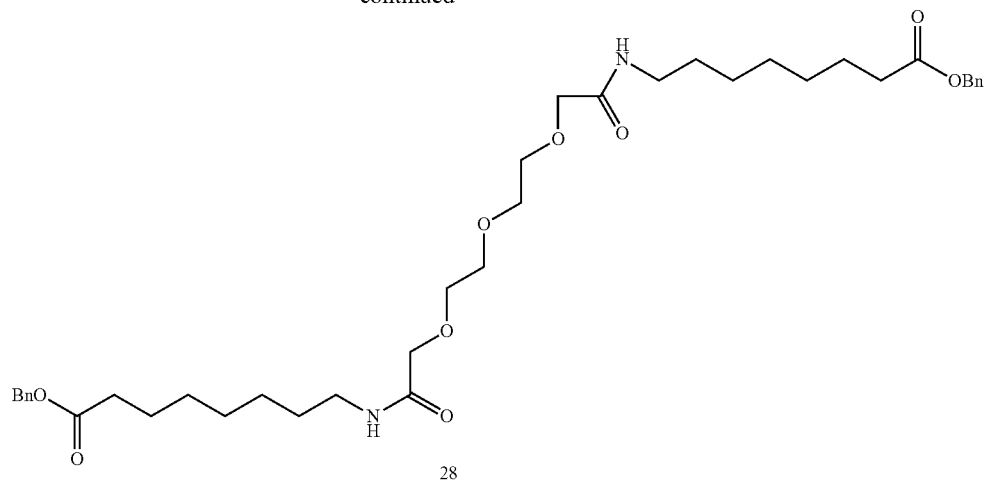
28
↓ Pd(OH)₂/C/H₂
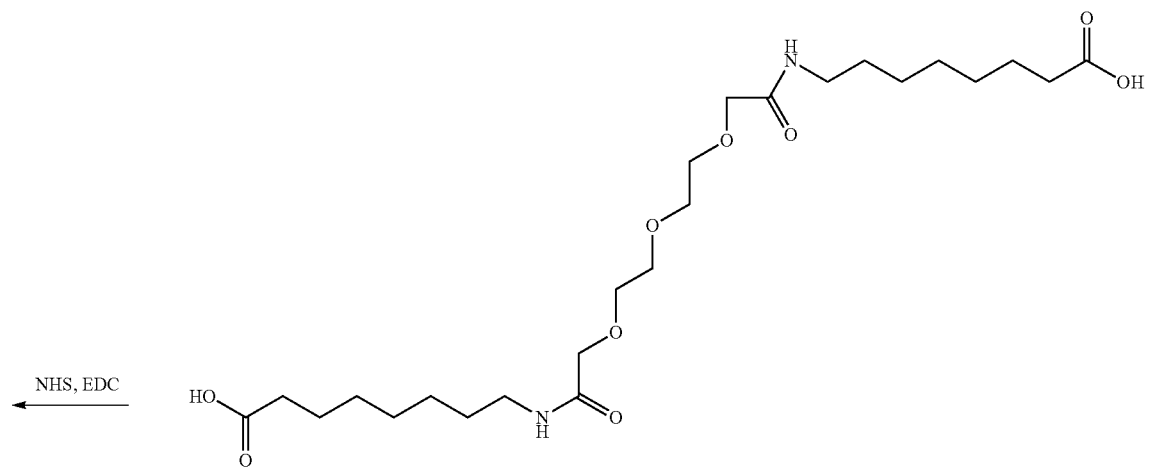
29
← NHS, EDC
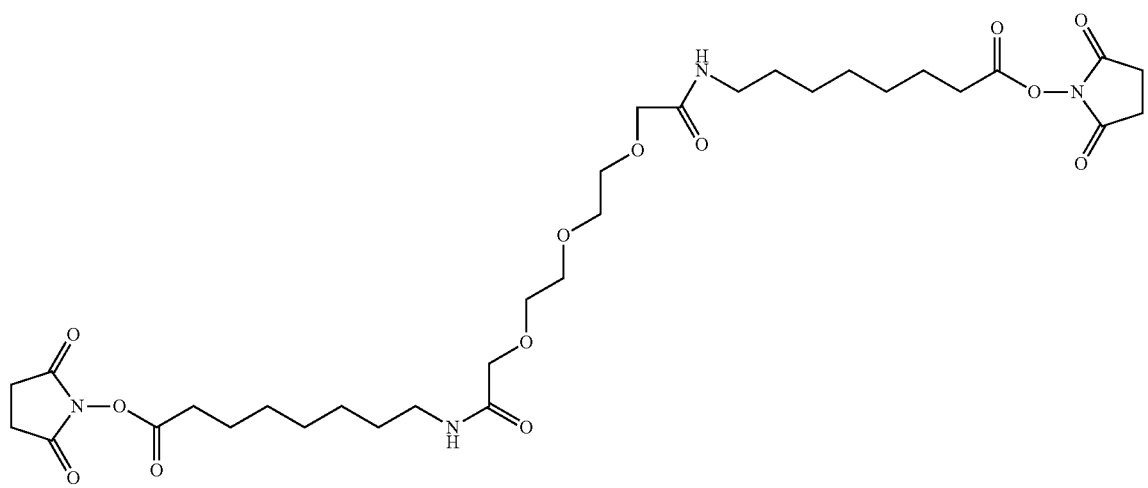
30

Example 3: Synthesis of Sulfated Dendritic Cluster Compounds

Example 3.1: Preparation of Benzyl Ester 2

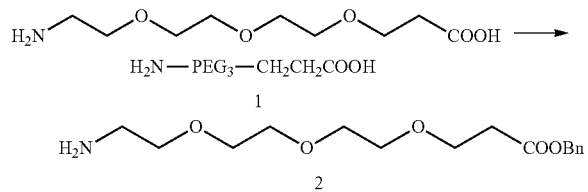

3-(2-(2-(2-Aminoethoxy)ethoxy)ethoxy)propanoic acid 1 ($H_2N(PEG)_3CH_2CH_2COOH$ or PEG aminoacid) (1.0 g, 4.52 mmol) is dissolved in benzyl alcohol (30 mL, 287 mmol) and cooled to 0° C. Thionyl chloride (6 mL, 82.2 mmol) is added slowly dropwise. The reaction mixture is stirred at 0° C. for 15 min followed by heating at 100° C. for 5 hours. Then this is diluted with diethyl ether and the oily residue is collected and purified by flash chromatography on silica gel eluting with DCM:MeOH, 9:1→1:1 to afford the benzyl ester (2, 1.2 g, 3.9 mmol, 85%). $R_f$=0.15 (DCM:MeOH, 9:1). $^{13}$C-NMR (125 MHz, $CDCl_3$) δ 171.64, 135.83, 128.51, 128.18, 128.12 70.25, 70.14, 70.13, 69.99, 66.73 66.46, 66.34, 50.07, 39.70, 35.0. HRMS (ESI) Calc for $C_{16}H_{26}NO_5$ [M+Na]$^+$ m/z, 312.1811; found, 312.1806.

Example 3.2: Preparation of tetrabenzyl ester 4

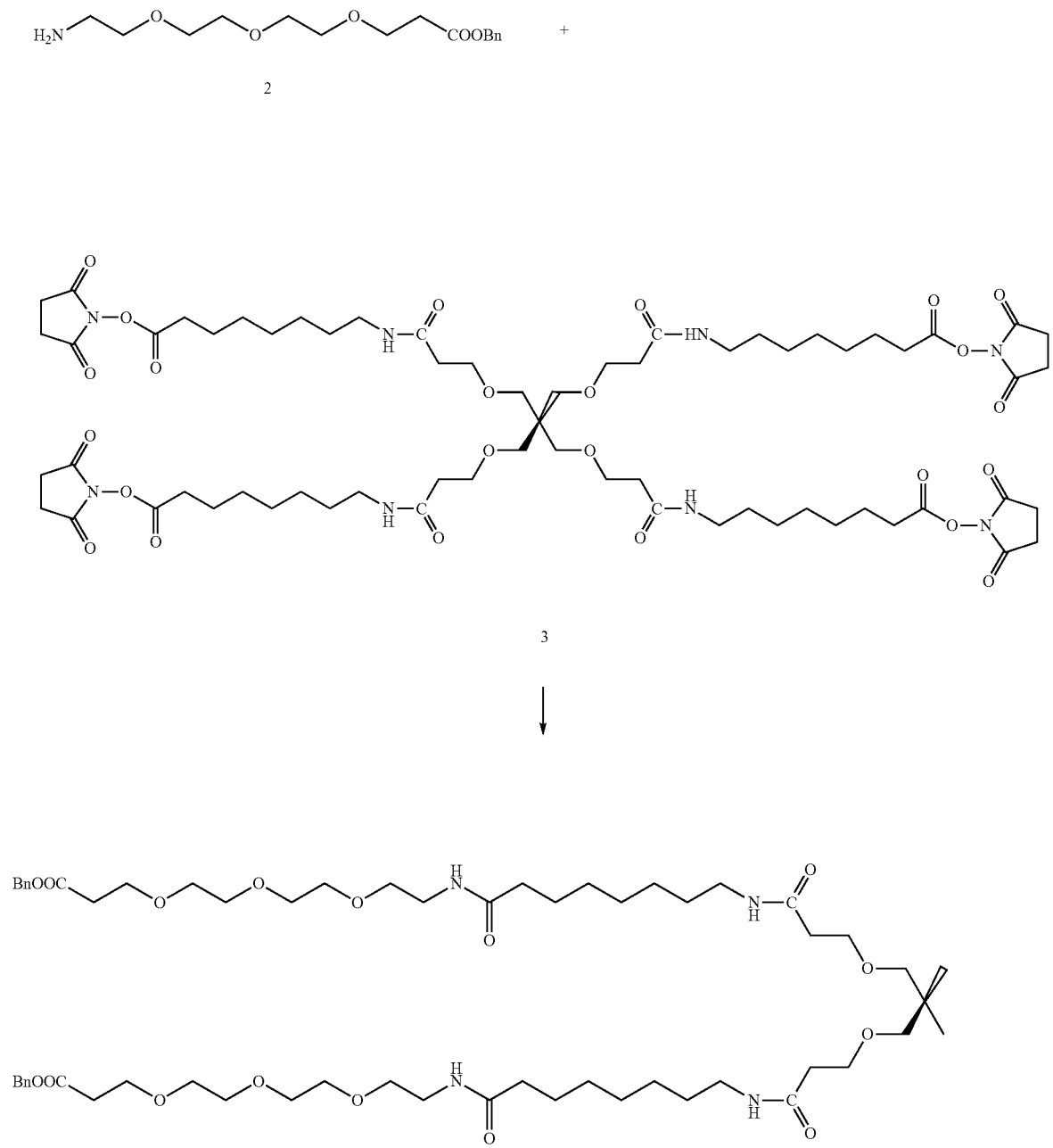

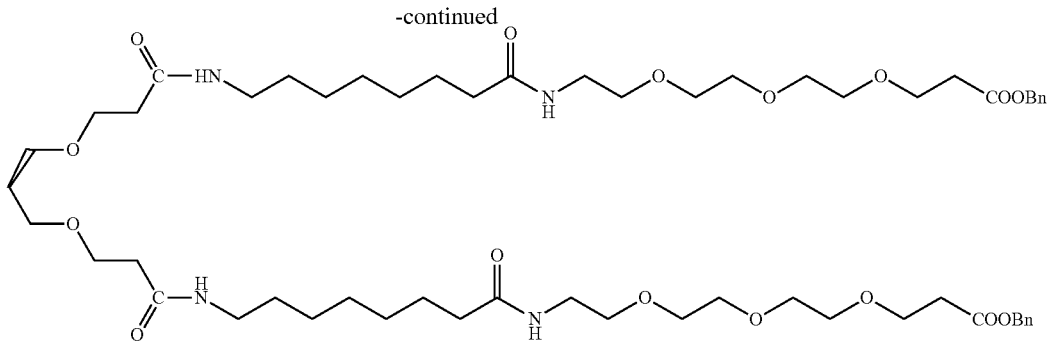

4

The benzyl ester 2 (768 mg, 2.46 mmol) and tetra-succinimidyl ester (3, 680 mg, 0.493 mmol) are dissolved in dry DMF (5 mL) and treated with triethylamine (0.5 mL, 3.94 mmol). After stirring for 24 hrs the mixture is diluted with ethyl acetate and washed with water twice, dried over magnesium sulfate and concentrated. The residue is dissolved in hot EtOAc, the crystals are filtered off and discharged. The mother liquor is concentrated and the residue is purified by flash chromatography on silica gel eluting with Chloroform:ethyl acetate:MeOH, 5:2:0.5 to afford the tetra-benzyl ester (4, 710 mg, 0.328 mmol, 78%). $R_f$=0.3 (Chloroform:ethyl acetate:MeOH, 5:2:1). $^{13}$C-NMR (125 MHz, CDCl$_3$) δ 173.24, 171.35, 135.81, 128.45, 128.12, 128.01, 70.43, 70.33, 70.12, 69.74, 69.50, 69.20, 67.41, 66.49, 66.16, 45.30, 42.37, 39.99, 39.37, 37.05, 36.74, 36.84, 35.06, 33.91, 30.40, 29.53, 29.10, 28.95, 26.72, 25.53. HRMS calcd for $C_{113}H_{180}N_8O_{32}Na$ [M+Na]$^+$ m/z 2184.2625, found 2184.2617.

Example 3.3: Preparation of tetraacid 5

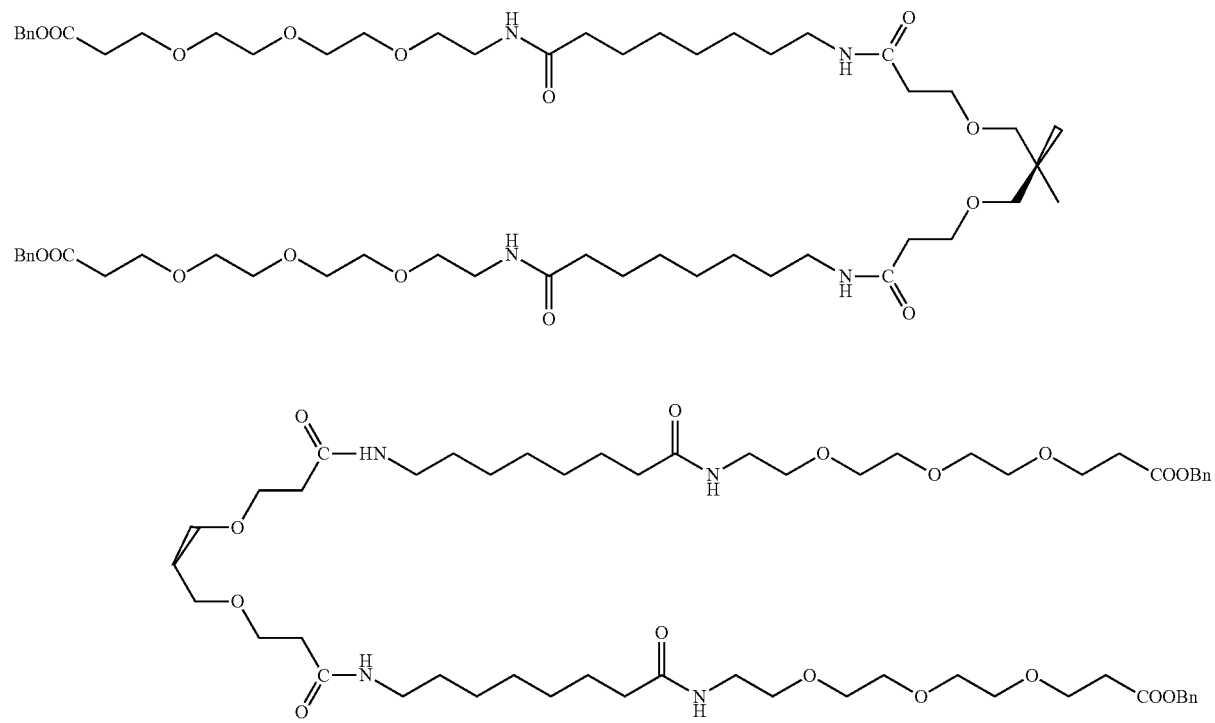

4

↓

-continued

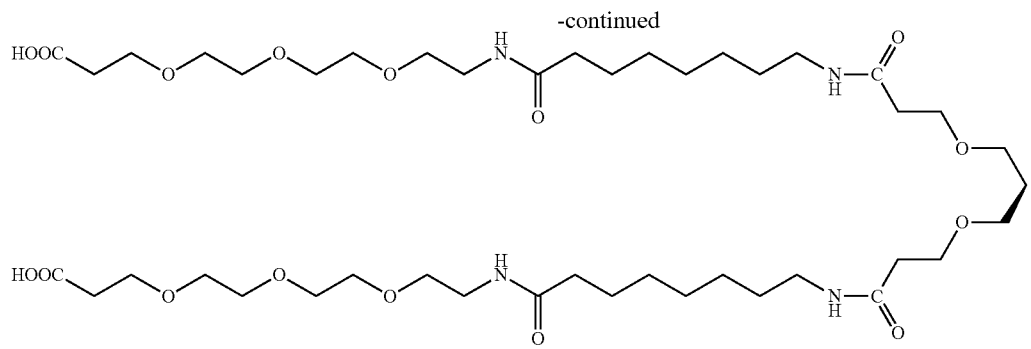

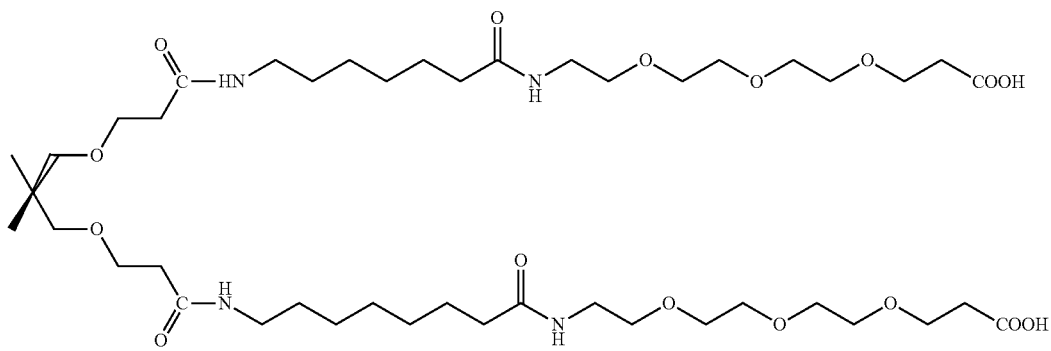

5

Tetra benzyl ester (4, 350 mg, 0.162 mmol) is dissolved in dry THF (8 mL). Water (2 mL) and glacial acetic acid (2 drops) are added. The reaction mixture is treated with palladium hydroxide on carbon (20% Pd, 20 mg) and stirred for 3 hours under hydrogen at ambient temperature and pressure. The catalyst is filtered off and washed with 50% aqueous EtOH. The solution is concentrated to dryness to give a "long-armed" PEG-PET tetraacid (5, 291 mg, 0.161 mmol, 99%). The product is used in the next step without further purification. $R_f$=0.0 (base line, Chloroform:EthylAcetate:MeOH, 5:2:1). $^{13}$C-NMR (125 MHz, MeOD) δ 176.30, 175.44, 173.87, 71.61, 71.51, 71.38, 71.31, 70.69, 68.79, 67.94, 52.07, 48.76, 48.59, 46.77, 41.38, 41.04, 40.51, 40.40, 37.84, 37.07, 36.74, 34.83, 33.10, 31.66, 30.54, 30.27, 30.17, 27.97, 26.98, 26.02. HRMS calcd for $C_{85}H_{156}N_8O_{32}Na$ [M+Na]$^+$ m/z 1824.0723, found 1824.0736.

Example 3.4: Preparation of "long-armed" PET-PEG tetra-N-succinimidyl ester 6

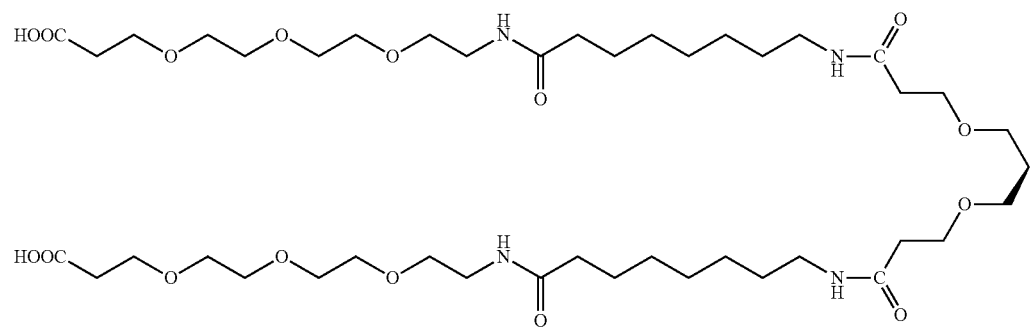

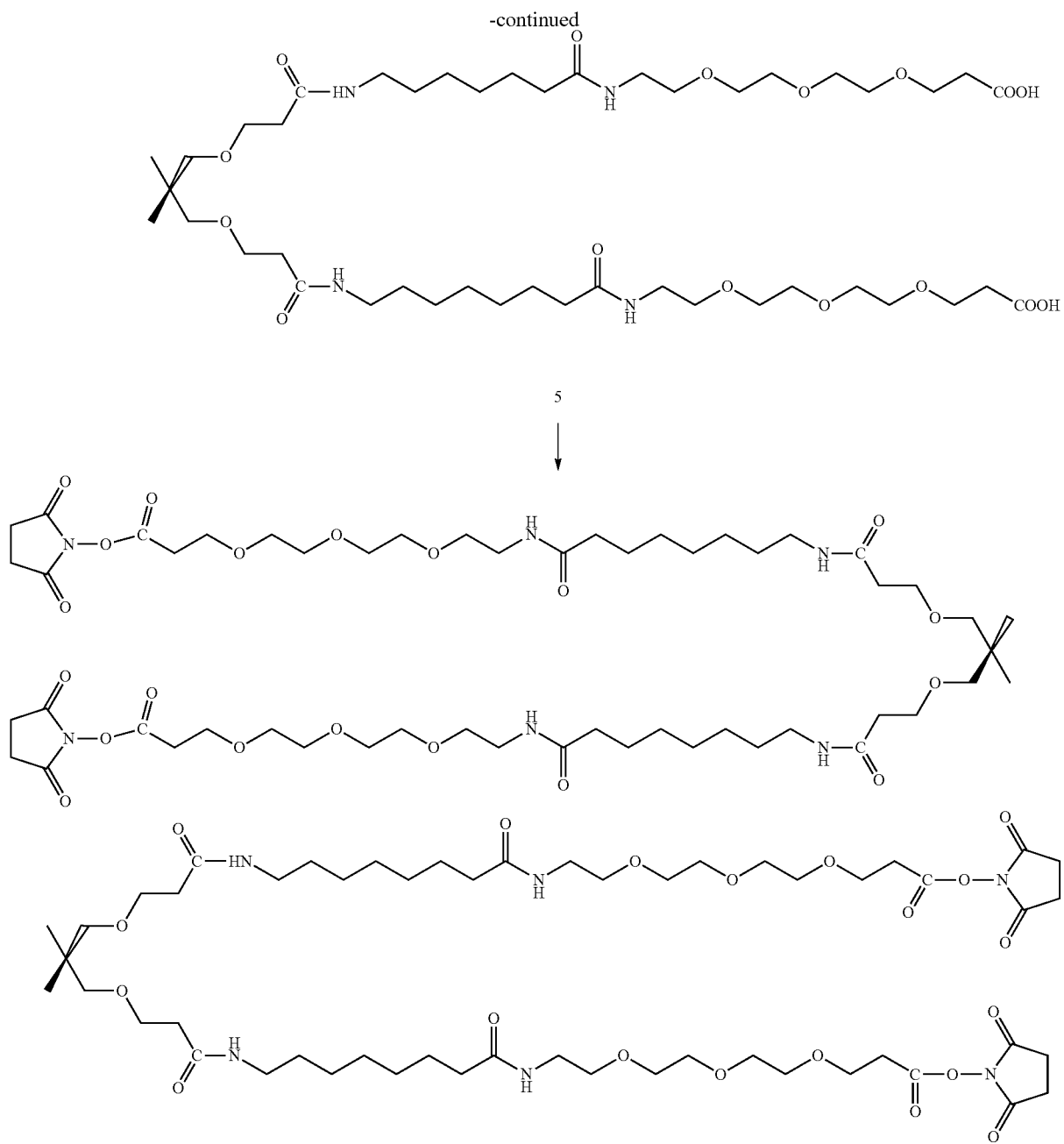

"Long-armed" PET-PEG tetraacid (5, 303 mg, 0.168 mmol) is dissolved in dry DMF (5 mL). N-Hydroxysuccinimide (118 mg, 1.0 mmol, 6 eq.), DIPEA (0.177 mL, 1.0 mmol, 6 eq.) and 1-ethyl-3-[3-dimethylaminopropyl]carbodiimide hydrochloride (EDC, 193 mg, 1.0 mmol, 6 eq.) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with chloroform:ethylAcetate:MeOH, 5:2:0.5→5:4:1 to give the "long-armed" PET-PEG tetra-succinimidyl ester (6, 306 mg, 0.14 mmol, 82%). $R_f$=0.25 (DCM:MeOH, 9:1). $^{13}$C-NMR (125 MHz, CDCl$_3$) δ 173.33, 171.97, 168.09, 166.71, 70.65, 70.48, 70.45, 70.34, 70.22, 70.14, 70.08, 69.74, 69.20, 67.43, 66.51, 65.96, 65.66, 51.62, 45.30, 40.06, 39.41, 39.11, 36.76, 36.39, 35.85, 34.80, 33.87, 32.72, 32.11, 30.32, 29.50, 29.08, 28.92, 27.42, 26.70, 25.56, 25.53, 25.41. HRMS calcd for $C_{101}H_{168}N_{12}O_{40}$Na [M+Na]$^+$ m/z 2212.1379, found 2212.1382.

Example 3.5: General Procedure a (GPA): Trichloroacetimidate Formation

Starting material with unprotected anomeric centre (1 eq) is dissolved in dry DCM (20 eq) and cooled in an ice-bath.

Trichloroacetonitrile (20 eq) and DBU (0.1 eq) are added. After 15 min the ice-bath is removed and the reaction allowed to warm to room temperature and left until tlc indicates the reaction is complete. The mixture is diluted with DCM and washed water twice, dried over magnesium sulfate and concentrated. The residue is purified by silica gel chromatography (ethyl acetate:petroleum ether, 1:1→2:1) to yield the trichloroacetimidate donor as a foam.

Example 3.6: Preparation of 2,3,4,6-tetra-O-acetyl-α-D-glucopyranosyl-(1→4)-2,3,6-tri-O-acetyl-α,β-D-glucopyranosyl trichloroacetimidate (10a)

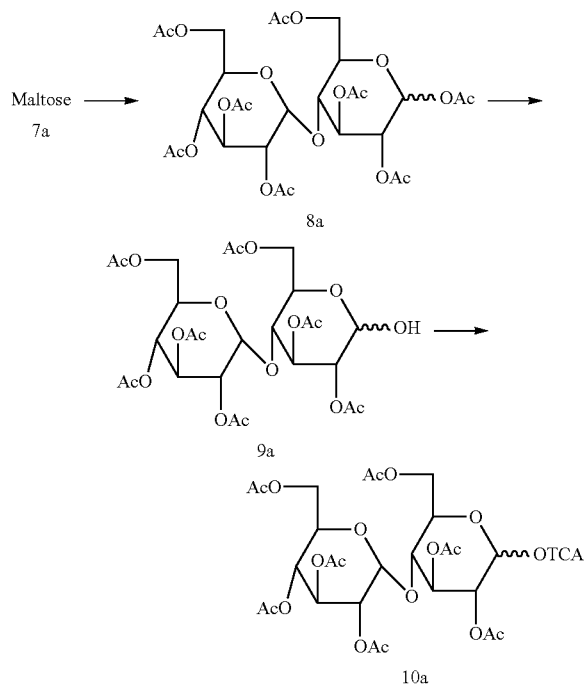

Maltose 7a (3 g, 8.76 mmol) is dissolved in dry pyridine (20 mL) and cooled to 0° C. and acetic anhydride (10 mL) is added. The reaction mixture is allowed to warm up to room temperature over 1 h and left, stirring at RT for 24 hours. Then the solvents are removed in vacuum. The mixture is diluted with DCM and washed with saturated aq. sodium bicarbonate and water, dried over magnesium sulfate and concentrated. The residue is purified by silica gel chromatography (ethyl acetate:petroleum ether, 1:1) to furnish per-acetylated maltose 8 as a syrup (5.3 g, 7.8 mmol, 89%), TLC (ethyl acetate:petroleum ether, 1:1 v/v): $R_f$=0.45. This is used directly for the synthesis of compound 9a. Compound 8a (3 g, 4.42 mmol) and hydrazine acetate (100 mg, 1.05 mmol, 0.2 eq.) are dissolved in dry DMF and stirred at 50° C. for 40 min. Then the mixture is diluted with EtOAc and washed with saturated aq. sodium bicarbonate and water, dried over magnesium sulfate and concentrated. The residue is purified by silica gel chromatography (ethyl acetate:petroleum ether, 1:1→2:1) to afford 9 as a syrup (2.6 g, 4.1 mmol, 92%), TLC (ethyl acetate:petroleum ether, 2:1 v/v): $R_f$=0.35. Compound 10a is prepared from 9a (1.8 g, 2.8 mmol) following general procedure A: the residue was purified by silica gel chromatography to afford a known compound 10a (2.05 g, 2.63 mmol, 93% yield); TLC (ethyl acetate:toluene, 1:1, v/v): $R_f$=0.35. $^{13}$C-NMR (125 MHz, CDCl$_3$) δ 170.58, 170.46, 170.33, 169.93, 169.64, 169.41, 160.93, 127.85, 129.02, 128.21, 125.29, 95.83, 95.07, 92.82, 90.72, 74.82, 72.92, 72.65, 72.29, 72.00, 70.59, 70.17, 70.03, 69.39, 68.60, 68.05, 62.63, 62.30, 61.44, 20.88, 20.74, 20.64, 20.58, 20.35.

Example 3.7: General Procedure B (GPB): Glycosylatlon—TCA Chemistry

A solution of the trichloroacetimidate donor (1.3 eq) and the glycosyl acceptor alcohol (1 eq) in anhydrous DCM (40 mL per mmol acceptor) is cooled to reaction temperature (between 0° C. and −20° C.), powdered molecular sieves (4&) are added and the suspension stirred at the temperature. After 15 min, trimethylsilyl trifluoromethanesulfonate (0.3 eq) is added and the reaction mixture stirred at reaction temperature until TLC (toluene/ethyl acetate 4:1) indicated completion. The mixture is diluted with ethyl acetate and filtered through celite into aq. sodium bicarbonate, the organic layer is washed with water and saturated aq. sodium chloride, dried over magnesium sulfate and concentrated. The residue is purified by flash chromatography to yield the fully protected saccharides with linkers.

Example 3.8: Preparation of β-N-benzyloxycarbonyl-hexyl (2,3,4,6-tetra-O-acetyl-α-D-glucopyrano-syl)-[1→4]-2,3,6-tri-O-acetyl-β-D-glucopyranoslde (12a)

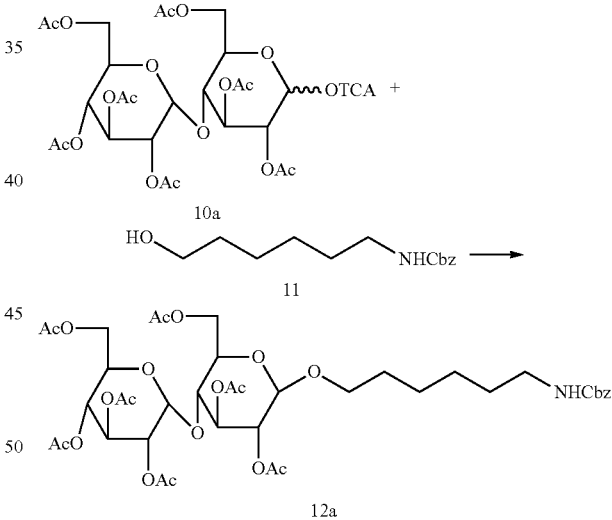

Compound 12a is prepared from compound 10a (1.9 g, 2.4 mmol) and N-benzyloxycarbonyl-6-hydroxyhexyl amine 11 (Z=Cbz, 0.92 g, 3.7 mmol) in the presence of TMSOTf (0.13 mL, 0.70 mmol) according to general procedure B. The residue is purified by silica gel chromatography (15-40% ethyl acetate in petroleum ether) to furnish the title compound (1.95 g, 2.24 mmol, 92%). TLC (ethyl acetate:petroleum ether, 1:2, v/v): $R_f$=0.45. $^{13}$C-NMR (125 MHz, CDCl$_3$) δ 170.41, 170.37, 170.12, 169.83, 169.51, 169.33, 156.49, 156.45, 136.74, 128.70, 128.38, 128.23, 127.92, 100.16, 95.46, 75.34, 72.87, 72.17, 72.00, 71.38, 69.97, 69.77, 69.29, 68.40, 68.07, 66.33, 62.82, 62.28, 61.52, 60.25, 40.83, 32.47, 29.82, 29.72, 28.45, 26.34, 26.22, 25.37, 25.30, 20.87, 20.77, 20.67, 20.51, 20.49, 20.44. HRMS (ESI) Calc for $C_{40}H_{55}NO_{20}Na$ [M+Na]$^+$ m/z, 829.3215; found, 829.3220.

Example 3.9: Preparation of 6-N-benzyloxycarbonyl-hexyl-2,3,4,6-tetra-O-acetyl-β-D-glucopyranoside (12b)

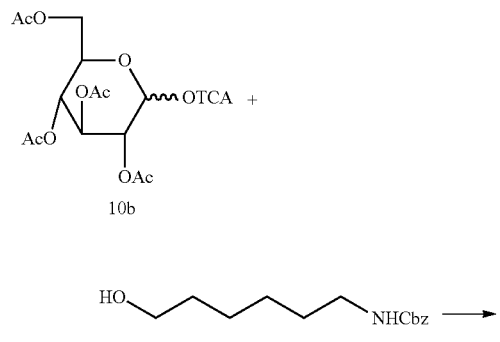

Compound 12b is prepared from a TCA donor 10b (6.4 g, 13 mmol) and N-benzyloxycarbonyl-6-hydroxyhexyl amine 11 (4.2 g, 1.3 eq., 17 mmol) in the presence of TMSOTf (0.72 mL, 0.3 eq., 3.9 mmol) according to general procedure B. The residue is purified by silica gel chromatography (15-40% ethyl acetate in petroleum ether) to furnish the title compound 12b (5.1 g, 8.8 mmol, 68%). TLC (toluene:ethyl acetate, 2:1, v/v): $R_f$=0.4. $^{13}$C-NMR (125 MHz, CDCl$_3$) δ 170.6, 170.2, 169.3, 169.2, 156.4, 137.8, 136.7, 100.8, 72.8, 71.7, 71.3, 70.9, 70.2, 69.9, 68.5, 67.1, 66.5, 62.0, 40.9, 29.8, 29.2, 26.3, 25.7, 25.4, 21.4, 20.7, 20.6, 20.5. HRMS (ESI) Calc for $C_{28}H_{39}NO_{12}Na$ [M+Na]$^+$ m/z, 604.2370; found, 604.2371.

Example 3.10: General Procedure C (GPC): Zemplen De-O-Acetylation

Starting material is dissolved in dry methanol (10 mL for 50 μmol) at RT and treated with a 1% freshly prepared solution of sodium methoxide (20 μL for 150 mg). Stirring of the reaction mixture is continued for 24 h at RT. After TLC (DCM:MeOH, 9:1) indicated the completion of the reaction the solution was concentrated and dried. The residues are purified by silica gel chromatography (DCM:MeOH, 9:1→5:1) to give de-O-acetylated products.

Example 3.11: Preparation of 6-N-benzyloxycarbonyl-hexyl (α-D-glucopyranosyl)-[1→4]-β-D-glucopyranoside (13a)

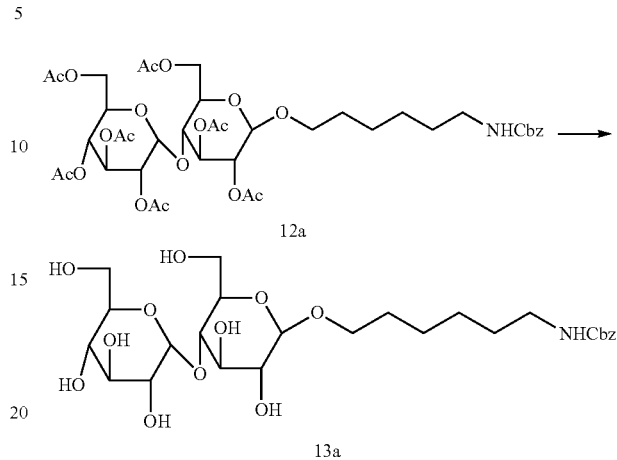

Compound 13a is prepared from compound 12a (600 mg, 0.689 mmol) according to general procedure C. The residue is purified by silica gel chromatography (ethyl acetate) to furnish the title compound (337 mg, 0.585 mmol, 85%). TLC (ethyl acetate:MeOH, 9:1, v/v): $R_f$=0.3. $^{13}$C-NMR (125 MHz, MeOD) δ 157.51, 137.10, 128.12, 127.60, 127.41, 102.9, 101.47, 79.91, 76.47, 75.17, 73.72, 73.37, 73.32, 72.84, 72.74, 71.80, 70.94, 70.15, 69.45, 67.81, 66.34, 65.95, 61.52, 61.41, 60.98, 40.52, 40.39, 29.44, 29.27, 26.21, 25.55, 25.34. HRMS (ESI) Calc for $C_{26}H_{41}NO_{13}Na$ [M+Na]$^+$ m/z, 598.2476; found, 598.2474.

Example 3.12: Preparation of 6-N-benzyloxycarbonyl-hexyl-β-D-glucopyranoside (13b)

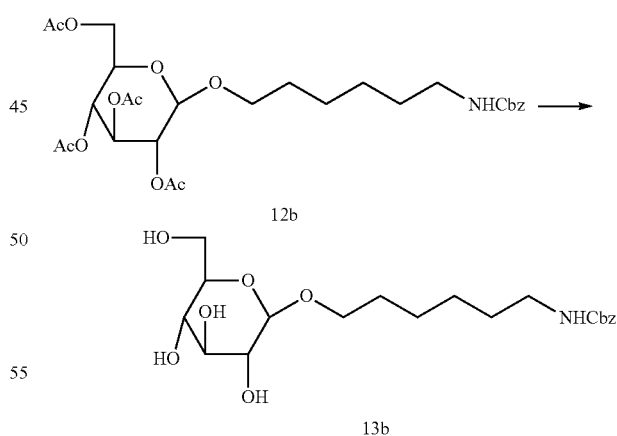

Compound 13b is prepared from compound 12b (600 mg, 1.03 mmol) according to general procedure C. The residue is purified by silica gel chromatography (ethyl acetate: MeOH, 9:1) to furnish the title compound (342 mg, 0.585 mmol, 80%). TLC (ethyl acetate:MeOH, 9:1, v/v): $R_f$=0.3. $^{13}$C-NMR (125 MHz, MeOD) δ 157.5, 137.1, 128.1, 127.5, 127.3, 102.9, 76.7, 76.5, 73.7, 72.2, 70.3, 69.3, 67.6, 66.3, 65.9, 61.4, 40.3, 29.2, 26.1, 25.5, 25.3.

Example 3.13: General Procedure D (GPD): Removal of N-Cbz Group

Palladium hydroxide on carbon (20% Pd, 500 mg per 1 g of substrate) is added to the solution of starting material in MeOH (10 mL for 1 g). The reaction mixture is stirred for just 20 min under hydrogen at ambient temperature and pressure. The catalyst is filtered off and washed with ethyl acetate:MeOH, 1:1. The solution is concentrated to dryness and chromatography of the residue (ethyl acetate:methanol: aq. ammonia, 4:1:0.05) gave compounds with a free amino-linker.

Example 3.14: Preparation of 6-aminohexyl (α-D-glucopyranosyl)-[1→4]-β-D-glucopyranoside (14a)

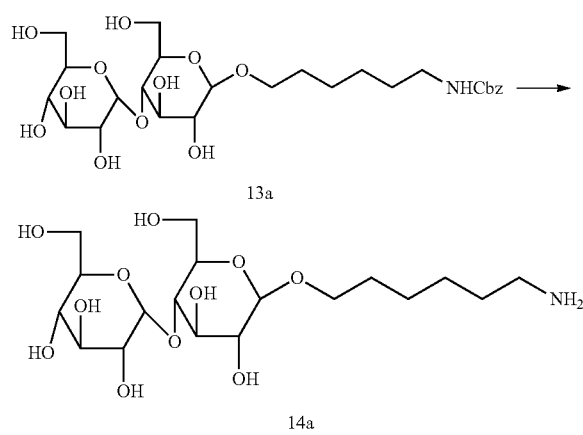

Compound 14a is prepared from compound 13a (333 mg, 0.578 mmol) according to general procedure D. The residue is purified by silica gel chromatography (33% MeOH in ethyl acetate) to afford the title compound (246 mg, 0.557 mmol, 96%). TLC (DCM:MeOH, 5:1, v/v): $R_f$=0.2. $^{13}$C-NMR (125 MHz, D$_2$O) δ 102.07, 99.65, 76.95, 76.33, 74.59, 73.63, 73.07, 72.90, 72.75, 71.71, 71.16, 70.47, 69.40, 68.29, 60.81, 60.57, 57.48, 39.76, 28.56, 27.99, 25.94, 25.44, 24.67, 16.88. HRMS (ESI) Calc for C$_{18}$H$_{35}$NO$_{11}$Na [M+Na]$^+$ m/z, 464.2108; found, 464.2111.

Example 3.15: Preparation of 6-aminohexyl-β-D-glucopyranoside (14b)

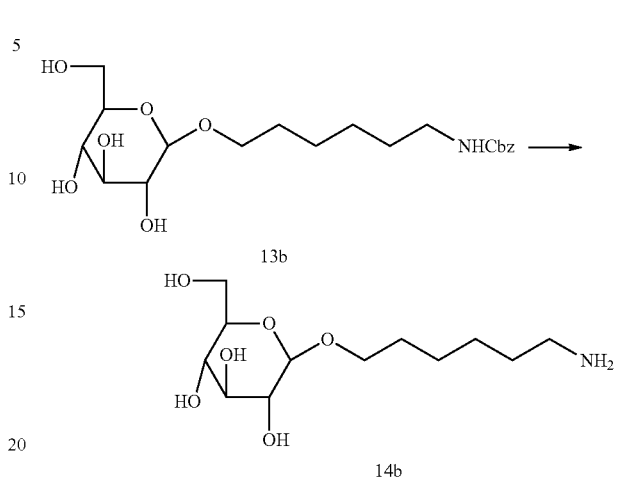

Compound 14b is prepared from compound 13b (627 mg, 1.52 mmol) according to general procedure D. The residue is purified by silica gel chromatography (33% MeOH in ethyl acetate→MeOH) to afford the title compound (419 mg, 1.5 mmol, 98.9%). TLC (DCM:MeOH, 5:1, v/v): $R_f$=0.2. $^{13}$C-NMR (125 MHz, D$_2$O) δ 101.2, 75.0, 74.9, 72.2, 70.4, 69.5, 68.7, 67.2, 59.8, 39.3, 29.8, 27.7, 27.6, 25.3, 24.9. HRMS (ESI) Calc for C$_{12}$H$_{26}$NO$_6$ [M+H]$^+$ m/z, 280.1760; found, 280.1754.

Example 3.16: General Procedure E (GPE): Coupling with Tetra-Succinimidyl Esters A solution of tetra-succinimidyl ester (1 eq) in dry DMF (40 mg per 1 mL of DMF) is added to the solution of glycoside with a 6 carbon linker, free hydroxyls and an unmasked amino-function (4-6 eq.) in dry DMF (100 mg per 1 mL of DMF) at room temperature. The reaction mixture is treated with triethylamine (8 eq) and stirred at RT for 24 hrs. DMF is removed in vacuo and the residue is purified by flash chromatography on silica gel eluting with acetonitrile:water: aq. ammonia, 6:2:1→3:2:1 to give the tetramer.

Example 3.17: Preparation of 16b (Short-Armed Cluster with Glucose)

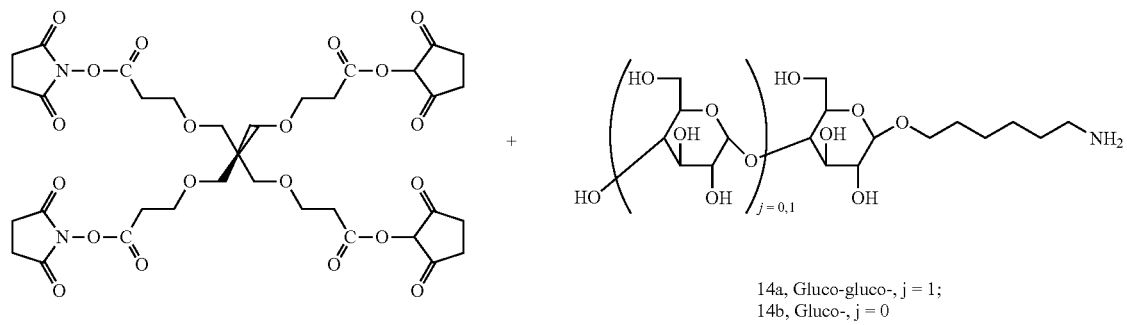

14a, Gluco-gluco-, j = 1;
14b, Gluco-, j = 0

-continued

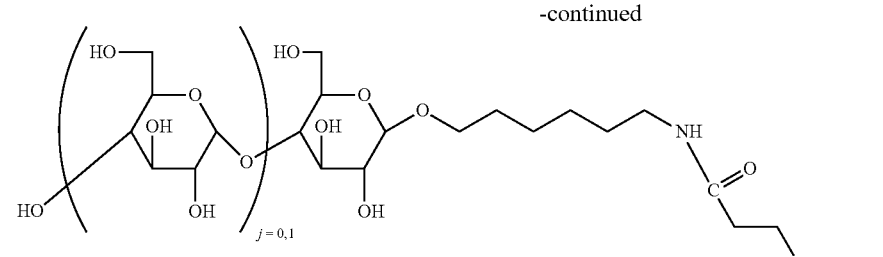

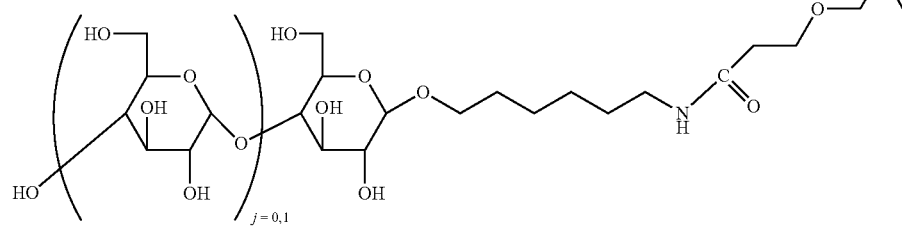

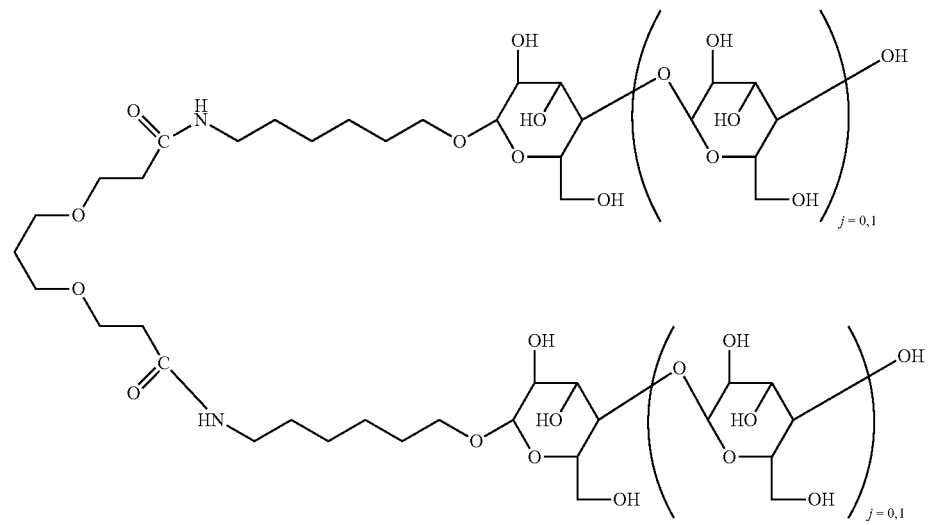

16a, Gluco-gluco-, j = 1;
16b, Gluco-, j = 0

Compound 16b is prepared from compounds 15 (103 mg, 0.126 mmol) and 14b (212 mg, 0.76 mmol) following general procedure E: The residue is purified by silica gel chromatography (acetonitrile:water:aq. ammonia, 6:2:1→3:2:1) to give the tetramer 16b as a foam (179 mg, 0.122 mmol, 96% yield); TLC (acetonitrile:water:aq. ammonia, 6:2:1, v/v): $R_f$=0.2. $^{13}$C-NMR (125 MHz, $D_2O$) δ 172.9, 101.0, 75.03, 75.0, 72.3, 70.9, 70.5, 69.5, 68.8, 68.4, 67.2, 66.7, 59.9, 44.3, 38.5, 35.5, 35.1, 34.5, 27.8, 27.7, 27.5, 25.0, 23.9. HRMS (ESI) Calc for $C_{65}H_{120}N_4Na$ $[M+Na]^+$ m/z, 1491.7783; found, 1491.7773.

Example 3.18: Preparation of 16c (PET Clusters with Maltose)
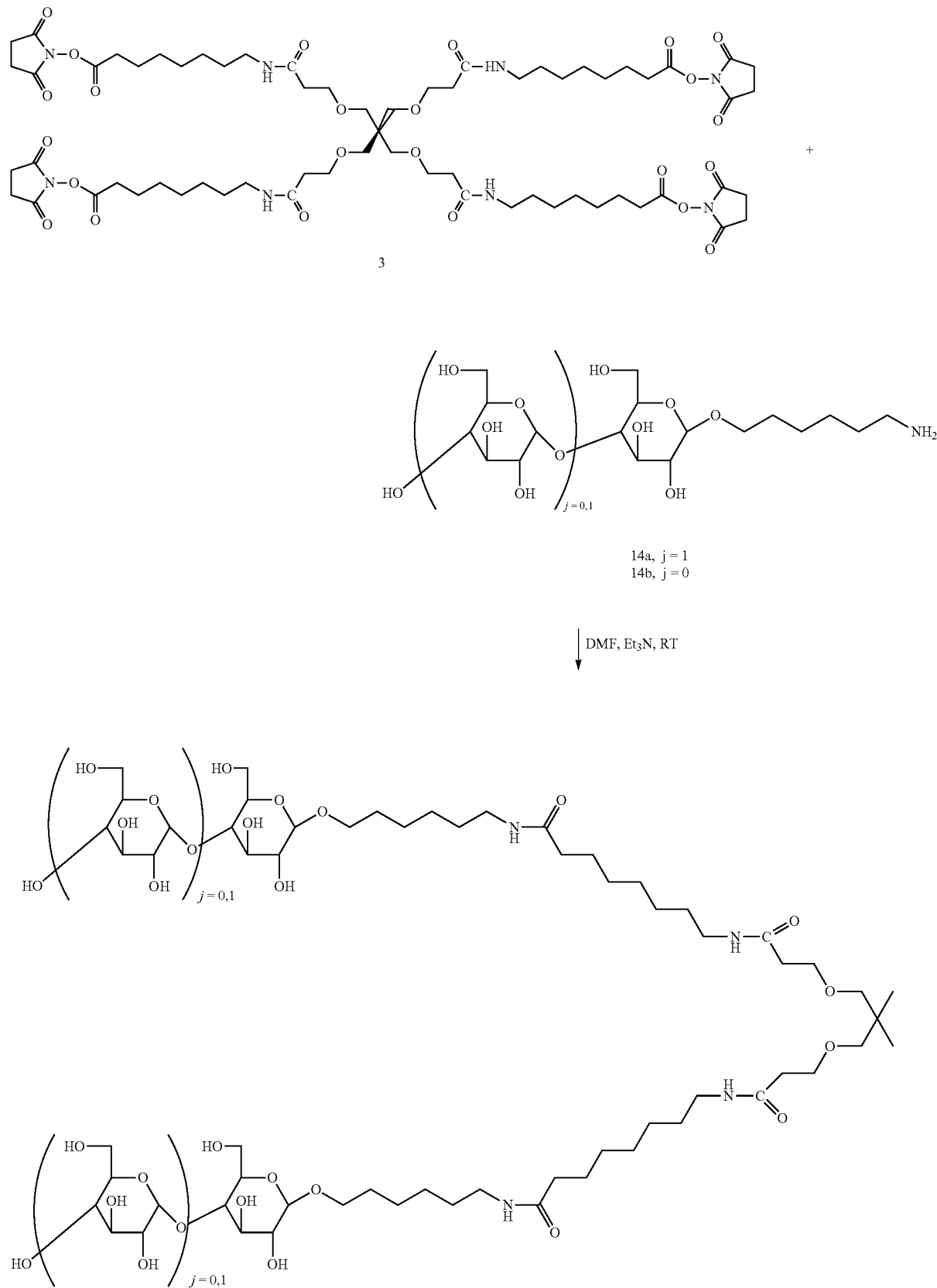

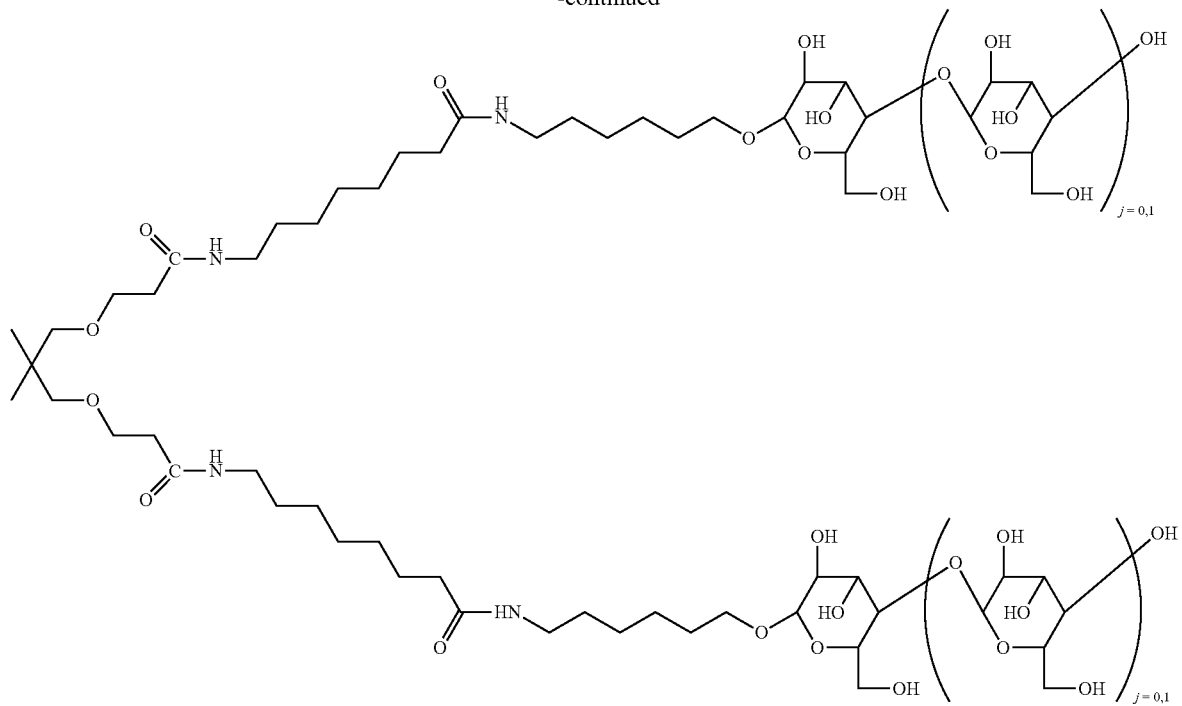

16c, j = 1
16d, j = 0

Compound 16c is prepared from compounds 3 (53 mg, 38.5 µmol) and 14a (87.5 mg, 0.198 mmol) following general procedure E: The residue is purified by silica gel chromatography (acetonitrile:water:aq. ammonia, 6:2:1→3:2:1) to give the tetramer 16c as a foam (89 mg, 33.2 µmol, 86% yield); TLC (acetonitrile:water:aq. ammonia, 6:2:1, v/v): $R_f$=0.2. $^{13}$C-NMR (125 MHz, D$_2$O) δ 175.37, 172.73, 101.31, 98.90, 76.29, 75.45, 73.76, 72.18, 72.05, 71.89, 70.86, 69.55, 68.49, 68.35, 66.80, 59.93, 59.69, 44.47, 38.58, 38.38, 35.63, 35.02, 27.96, 27.81, 27.60, 27.52, 25.40, 25.12, 24.68, 24.01. HRMS (ESI) Calc for C$_{121}$H$_{220}$N$_8$O$_{56}$Na [M+Na]$^+$ m/z, 2704.4511; found, 2704.4529.

Example 3.19: Preparation of 16d (PET Clusters with Glucose)

Compound 16d is prepared from compounds 3 (82 mg, 59.5 µmol) and 14b (99.7 mg, 0.357 mmol) following general procedure E: The residue is purified by silica gel chromatography (acetonitrile:water:aq. ammonia, 6:2:1→3:2:1) to give the tetramer 16d as a foam (118 mg, 58.0 µmol, 97% yield); TLC (acetonitrile:water:aq. ammonia, 6:2:1, v/v): $R_f$=0.2. $^{13}$C-NMR (125 MHz, D$_2$O) δ 175.4, 172.7, 101.6, 75.2, 72.5, 69.6, 69.0, 68.4, 66.8, 60.1, 47.8, 47.6, 47.4, 47.3, 47.1, 46.9, 46.7, 44.5, 38.6, 38.4, 35.7, 35.2, 28.1, 27.9, 27.7, 27.6, 25.5, 25.2, 24.8, 24.1. HRMS (ESI) Calc for C$_{97}$H$_{180}$N$_8$O$_{36}$Na [M+Na]$^+$ m/z, 2056.2398; found, 2056.2388.

Example 3.20: Preparation of 24a (PET-PEG with Maltose)

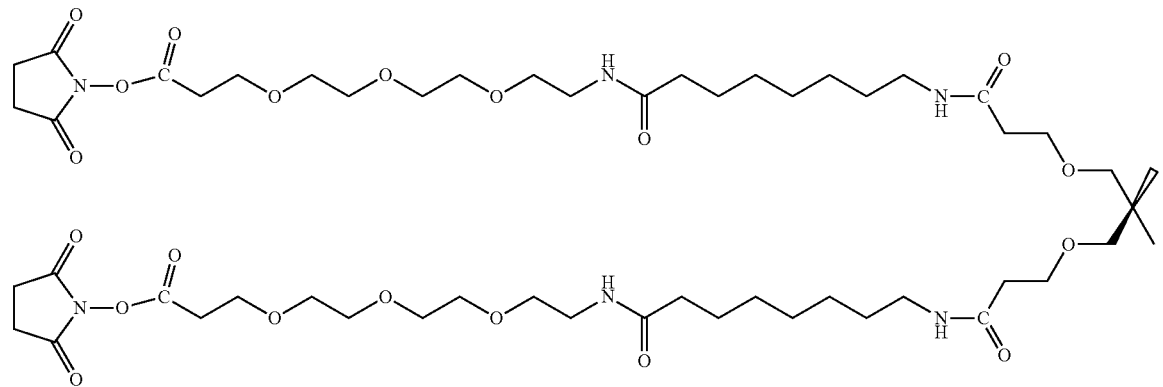

91
92
-continued
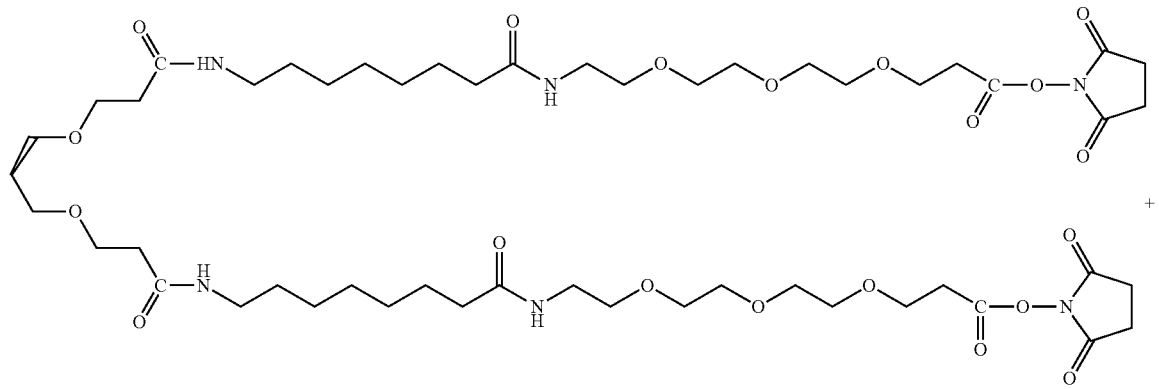
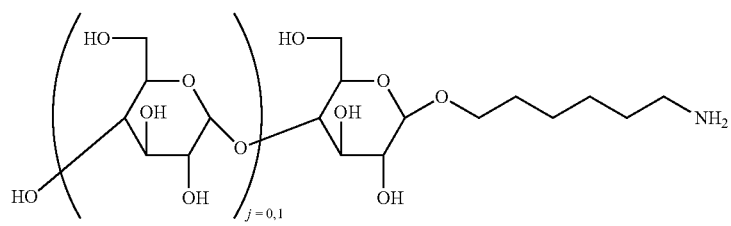
14a, j = 1
14b, j = 0
↓ DMF, Et₃N, RT
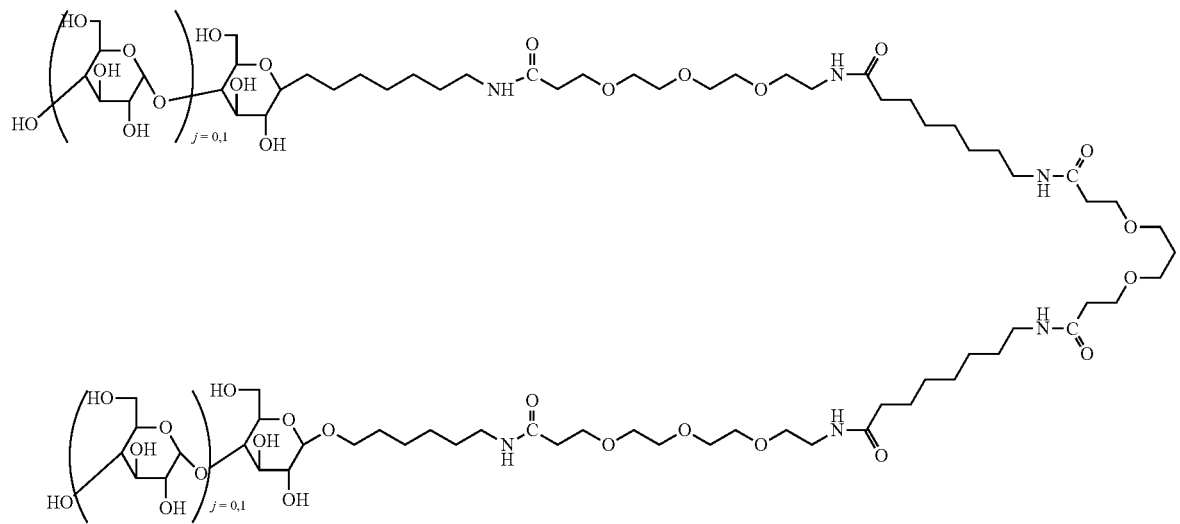

-continued

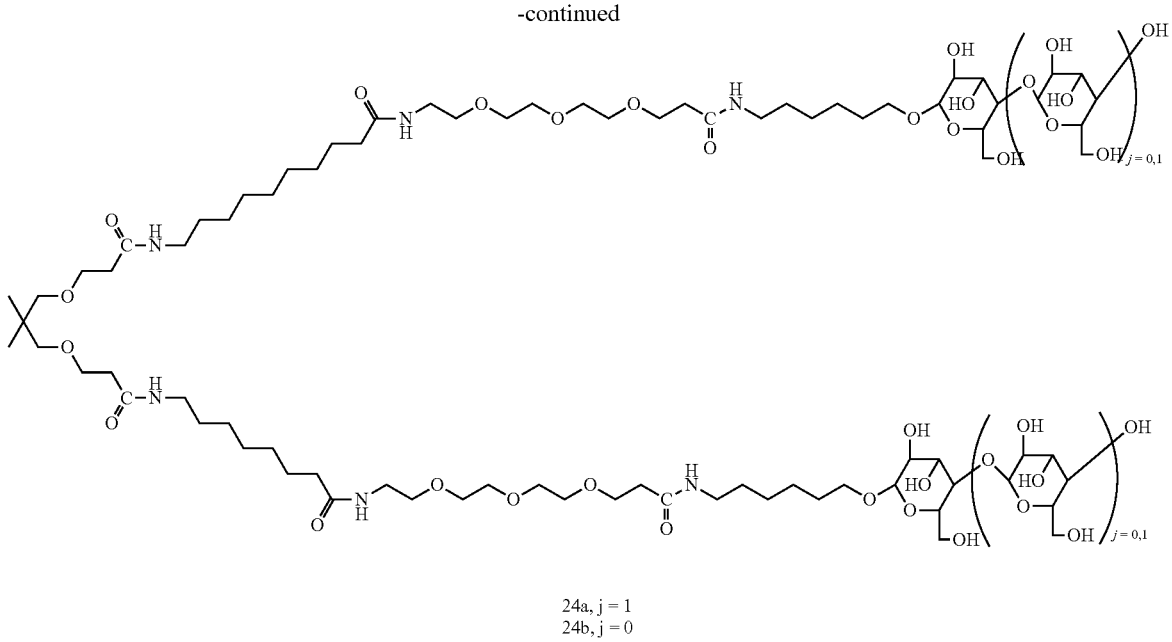

24a, j = 1
24b, j = 0

Compound 24a is prepared from compounds 6 (76 mg, 34.6 µmol) and 14a (81 mg, 0.183 mmol) following general procedure E: The residue is purified by silica gel chromatography (acetonitrile:water:aq. ammonia, 6:2:1→3:2:1) to give the tetramer 24a as a foam (110 mg, 31.5 µmol, 90% yield); TLC (acetonitrile:water:aq. ammonia, 6:2:1, v/v): $R_f$=0.2. $^{13}$C-NMR (125 MHz, $D_2O$) δ 173.75, 173.67, 102.17, 99.74, 77.09, 76.35, 74.64, 73.09, 72.94, 72.78, 71.75, 70.49, 69.77, 69.71, 69.63, 69.57, 69.41, 69.22, 69.01, 67.68, 66.94, 66.24, 60.83, 48.94, 39.50, 39.39, 38.97, 36.50, 36.23, 35.82, 34.41, 28.80, 28.65, 28.34, 26.23, 25.91, 25.44, 24.85. HRMS (ESI) calcd for $C_{157}H_{286}N_{12}O_{72}Na_2$ [M+2Na]$^{2+}$ m/z (%) 1769.9519 (50), 1770.4536 (100), 1770.9552 (98), 1771.4567 (70), 1771.9581 (40), 1772.4595 (25), 1772.9609 (10); found 1769.9454 (50), 1770.4546 (100), 1770.9449 (95), 1771.4470 (80), 1771.9501 (50), 1772.4545 (30), 1772.9556 (20).

Example 3.21: Preparation of 24b (PET-PEG with Glucose)

Compound 24b is prepared from compounds 6 (77 mg, 35.1 µmol) and 14b (58.9 mg, 0.211 mmol) following general procedure E: The residue is purified by silica gel chromatography (acetonitrile:water:aq. ammonia, 6:2:1→3: 2:1) to give the tetramer 24b as a foam (95 mg, 33.4 µmol, 94% yield); TLC (acetonitrile:water:aq. ammonia, 6:2:1, v/v): $R_f$=0.2. $^{13}$C-NMR (125 MHz, $D_2O$) δ 176.7, 174.6, 173.7, 173.6, 102.3, 76.0, 75.9, 73.2, 70.4, 69.7, 69.6, 69.5, 69.2, 69.0, 67.7, 66.9, 66.2, 60.8, 52.3, 45.3, 39.5, 39.4, 38.9, 36.5, 36.2, 35.8, 34.4, 28.8, 28.6, 28.3, 26.2, 25.9, 25.4, 24.8. HRMS (ESI) calcd for $C_{133}H_{248}N_{12}O_{52}Na$ [M+Na]$^+$ m/z (%) 2868.7131; found 2868.7120.

Example 3.22: General Procedure F (GPF): O-Sulfation

Sulfur trioxide trimethylamine complex (5 equiv. per hydroxyl group) is added to the starting materials in dry DMF (3 mL for 50 mg). The mixture is heated at 50-60° C. under argon for 72 h. MeOH (1 mL) is added and the mixture stirred for 15 min and concentrated in vacuo. Chromatography (acetonitrile:water:aq. ammonia, 6:2:1→3: 2:1→water:aq. ammonia, 6:1) affords O-sulfated products as ammonium salts. The resulting materials are dissolved in water, passed through a Dowex 50WX8-200 (Na$^+$) resin column (8×1 cm) and eluted with water. Fractions containing the products are evaporated and dried in vacuo to furnish sodium salts of final products.

Example 3.23: Preparation of 17b (Short-Armed Cluster with Glucose)
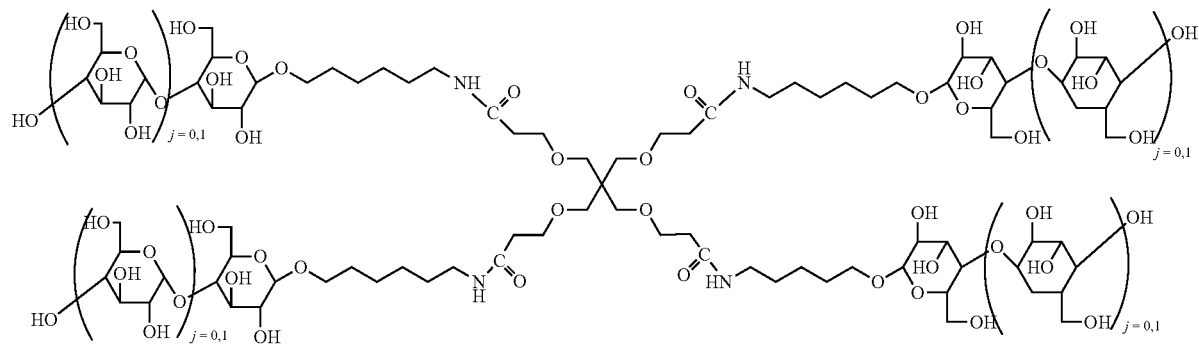
16a, j = 1;
16b, j = 0
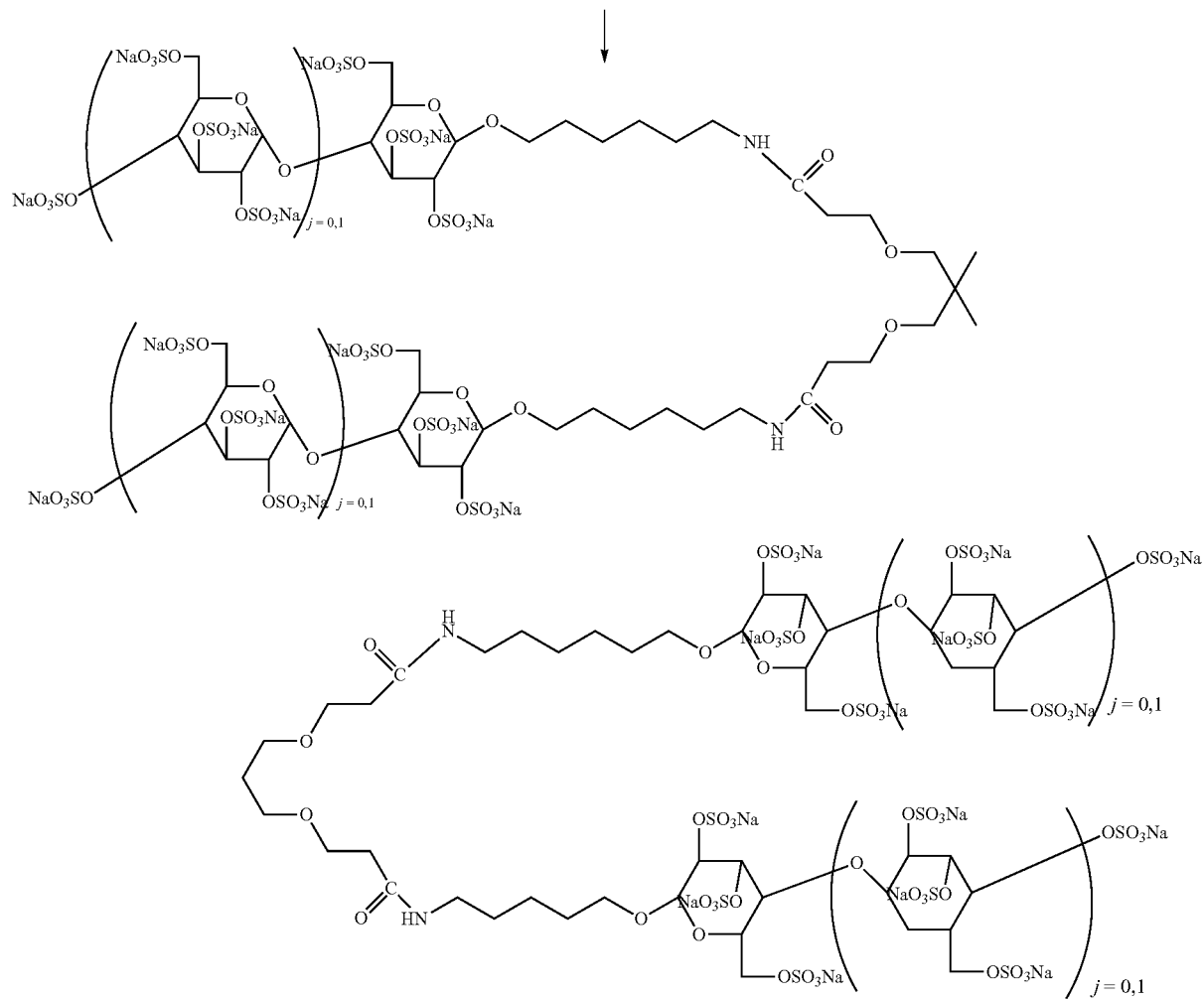
17a, j = 1;
17b, j = 0

Compound 17b is prepared from compound 16b (117 mg, 79.6 μmol) and sulfur trioxide trimethylamine complex (80 eq., 0.933 g, 6.36 mmol) following general procedure F to furnish 17b as a foam (208 mg, 75.6 μmol, 95% yield); TLC (acetonitrile:water:aq. ammonia, 3:2:1): $R_f$=0.2. $^{13}$C-NMR (125 MHz, D$_2$O) δ 173.1, 99.1, 75.2, 74.6, 72.5, 71.5, 69.5, 68.3, 67.0, 66.6, 66.2, 44.3, 38.5, 35.4, 27.6, 27.4, 25.0, 23.8.
Example 3.24: Preparation of 17c (PET Cluster with Maltose)
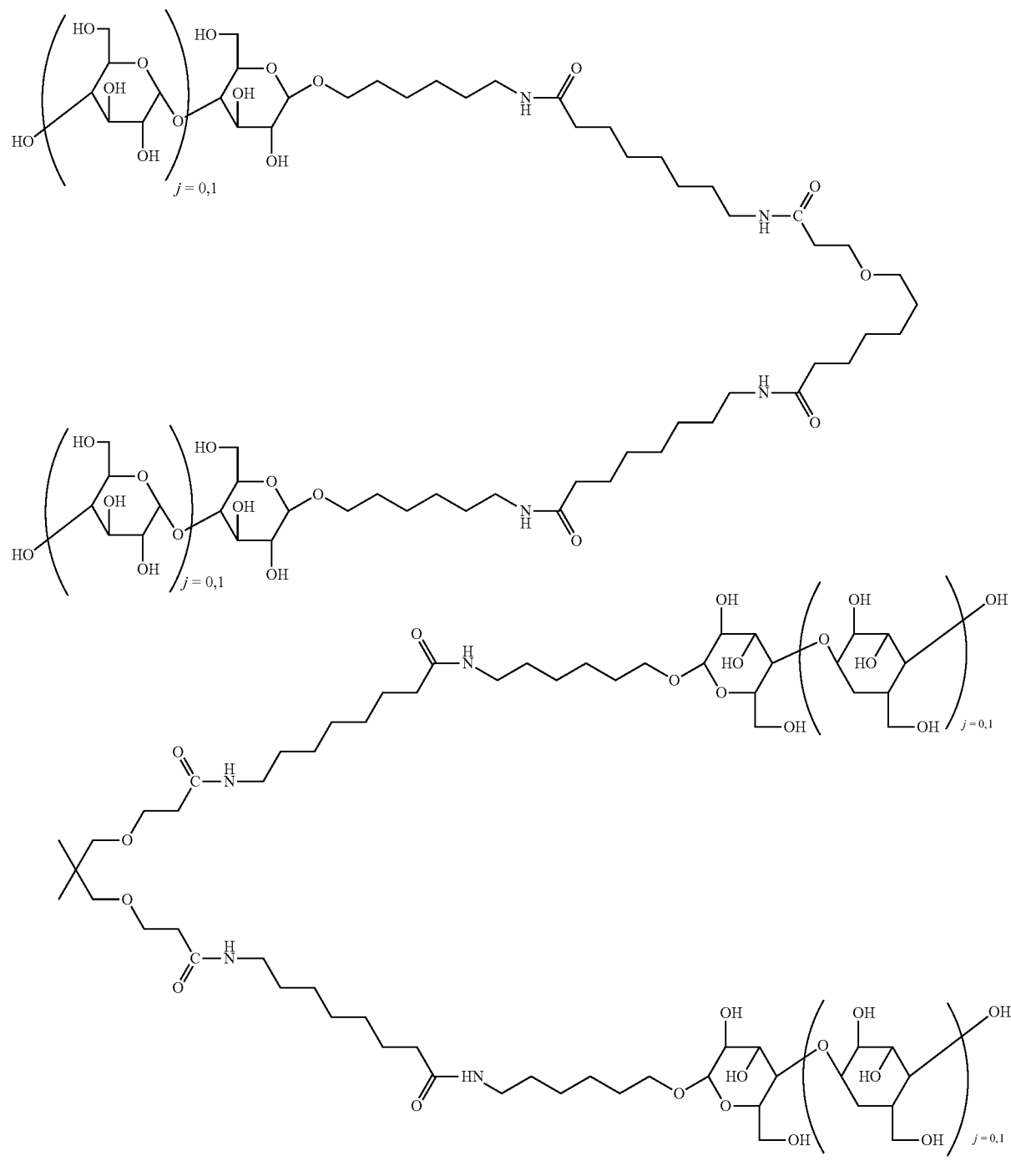
16c, j = 1
16d, j = 0
SO3•NMe (140 eq),
DMF, Ar, 60° C.

-continued

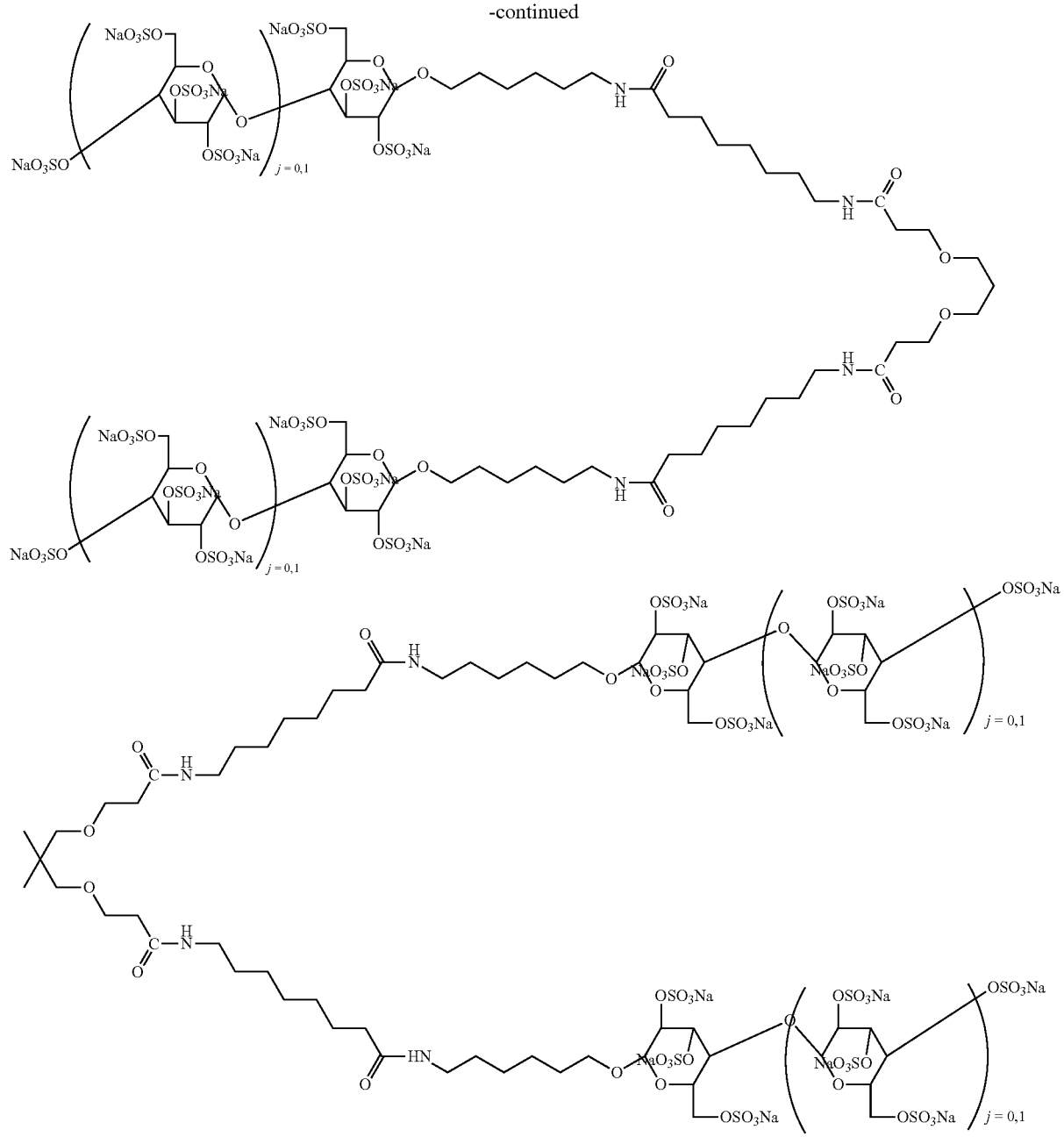

17c, j = 1
17d, j = 0

Compound 17c is prepared from compound 16c (62 mg, 23.1 μmol) and sulfur trioxide trimethylamine complex (140 eq., 542 mg) following general procedure F to furnish 17c as a foam (91 mg, 18.5 μmol, 69% yield); TLC (acetonitrile: water:aq. ammonia, 3:2:1): $R_f$=0.2. $^{13}$C-NMR (125 MHz, $D_2O$) δ 176.82, 174.04, 99.73, 94.39, 77.24, 76.16, 75.22, 73.82, 73.49, 72.26, 71.97, 70.09, 69.91, 69.29, 67.73, 66.27, 49.11, 39.58, 39.48, 36.56, 35.87, 28.62, 28.29, 26.21, 25.98, 25.54, 24.90.

Example 3.25: Preparation of 17d (PET Cluster with Glucose)

Compound 17d is prepared from compound 16d (48 mg, 23.5 μmol) and sulfur trioxide trimethylamine complex (80 eq., 542 mg, 1.88 mmol) following general procedure F to furnish 17d as a foam (71 mg, 21.4 μmol, 90% yield); TLC (acetonitrile:water:aq. ammonia, 3:2:1): $R_f$=0.2. $^{13}$C-NMR (125 MHz, $D_2O$) δ 176.6, 173.9, 100.0, 82.5, 80.4, 76.1, 75.5, 73.6, 72.4, 70.3, 69.2, 67.9, 67.6, 45.3, 39.5, 39.3, 36.5, 35.8, 28.5, 28.3, 28.2, 26.1, 25.8, 25.5, 24.7.

Example 3.26: Preparation of 25a (PET-PEG Cluster with Maltose)
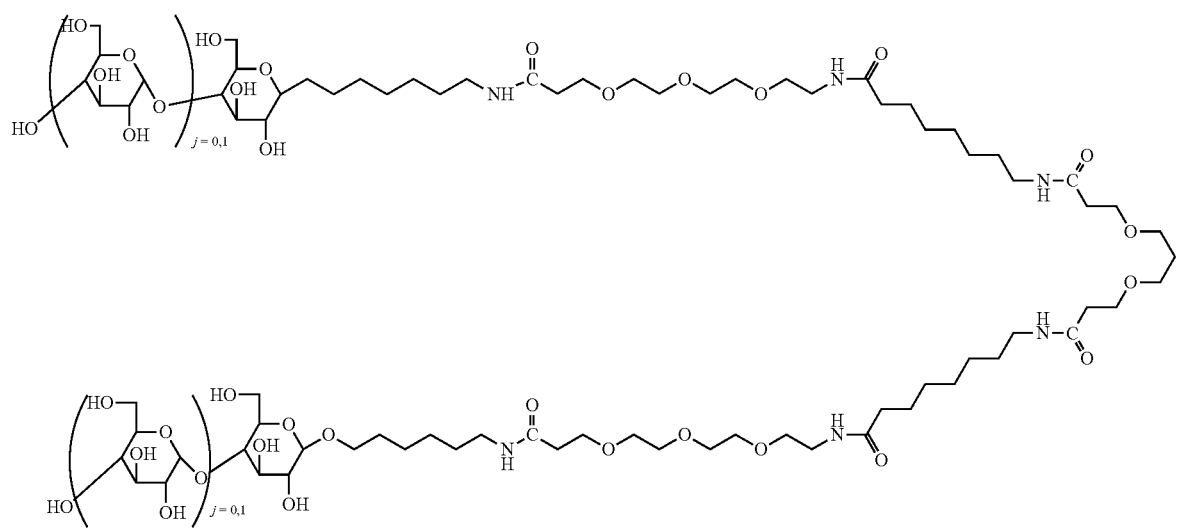
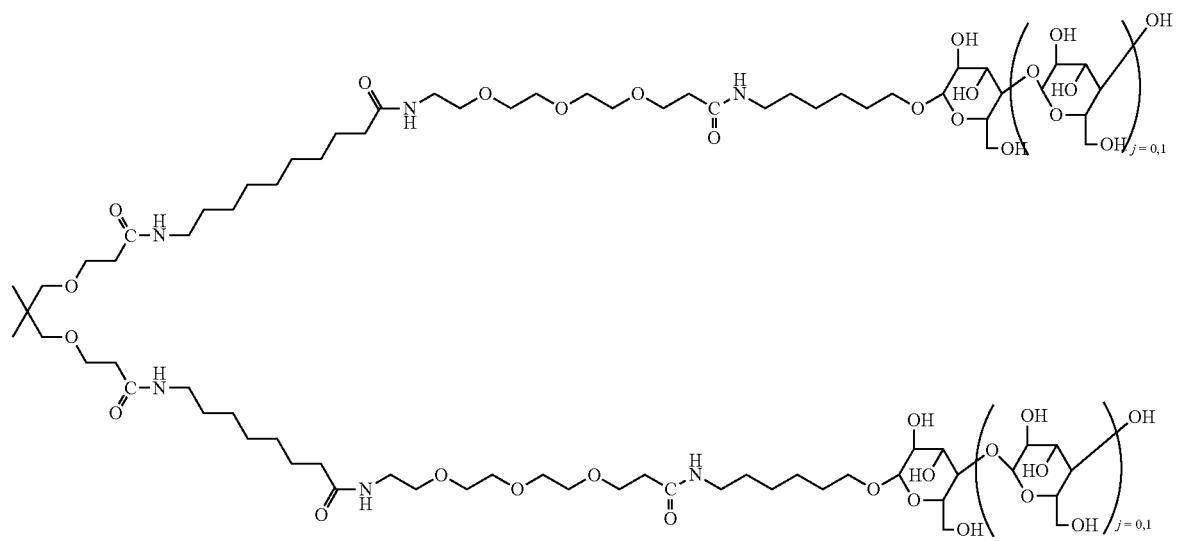
24a, j = 1
24b, j = 0
SO$_3$•NMe$_2$ (140 eq),
DMF, Ar, 60° C.

-continued

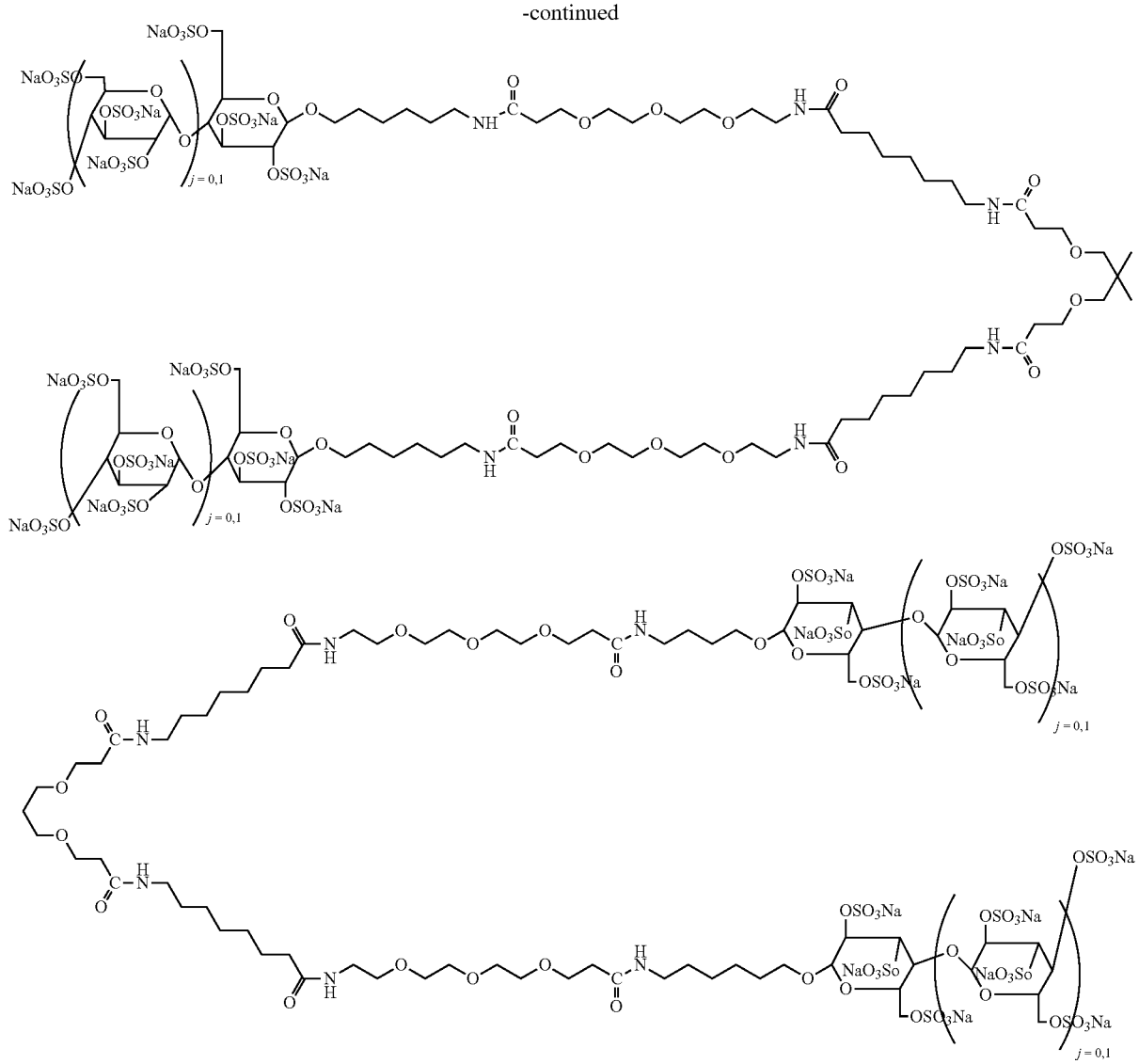

25a, j = 1
25b, j = 0

Compound 25a is prepared from compound 24a (49 mg, 14 μmol) and sulfur trioxide trimethylamine complex (140 eq., 287 mg) following general procedure F to furnish 25a as a foam (75 mg, 13.1 μmol, 93% yield); TLC (acetonitrile: water:aq. ammonia, 3:2:1): $R_f$=0.2. $^{13}$C-NMR (125 MHz, D$_2$O) δ 177.54, 174.41, 174.28, 100.14, 94.85, 77.78, 76.69, 75.65, 75.14, 74.26, 73.95, 73.28, 72.77, 72.48, 70.51, 70.44, 70.26, 50.20, 70.07, 69.75, 69.47, 68.33, 68.19, 67.47, 66.77, 45.87, 40.02, 39.49, 37.02, 36.72, 36.33, 29.11, 28.80, 28.76, 26.69, 26.43, 25.93, 25.09.

Example 3.27: Preparation of 25b (PET-PEG Cluster with Glucose)

Compound 25b is prepared from compound 24b (44 mg, 15.5 μmol) and sulfur trioxide trimethylamine complex (80 eq., 0.181 g, 1.236 mmol) following general procedure F to furnish 25b as a foam (60 mg, 14.5 μmol, 94% yield); TLC (acetonitrile:water:aq. ammonia, 3:2:1): $R_f$=0.2. $^{13}$C-NMR (125 MHz, D$_2$O) δ 176.9, 174.7, 173.8, 173.7, 99.9, 76.0, 75.3, 73.7, 72.3, 70.3, 69.7, 69.6, 69.5, 69.2, 68.9, 68.1, 67.6, 66.9, 66.2, 52.3, 45.3, 44.8, 39.5, 39.4, 38.9, 36.4, 36.2, 35.8, 34.4, 28.5, 28.2, 26.1, 25.8, 25.4, 24.8.

Example 4: Inhibition of Heparanase

Example 4.1: Assay Methodology

The assay methodology used is described in Hammond, E., et al., Development of a colorimetric assay for heparanase activity suitable for kinetic analysis and inhibitor screening, Anal. Biochem. 2010, 396 (1), 112-116.

Reagents were obtained from Sigma-Aldrich. Assays were carried out in 96-well microplates (Costar 9018 EIA/

RIA, Corning) that had been pretreated with a solution of 4% bovine serum albumin (BSA) in phosphate-buffered saline containing 0.05% Tween 20 (PBST) for 2 h at 37° C. The plates were then washed three times with PBST and shaken dry. Pretreated plates were stored at 4° C. for up to 2 weeks before use.

Recombinant human heparanase was expressed in insect cells and then purified from the cell medium into which it had been secreted. The medium was clarified by centrifugation at 17,700 g at 4° C. for 30 min before being loaded onto a 100 ml heparin-Sepharose column (GE Healthcare) preequilibrated to 20 mM sodium phosphate (pH 7.5). The column was eluted with a series of three 150 ml NaCl concentration steps in the same phosphate buffer: 0.3, 0.6, and 0.8 M. Heparanase-containing fractions eluting in the 0.8 M step were pooled (typically 70 ml) and dialyzed against 2 L of 10 mM sodium phosphate (pH 7.0) at 4° C. for 20 h. This material was then loaded onto a 55-ml Source 30S column (GE Healthcare) preequilibrated to 20 mM sodium phosphate (pH 7.0) and eluted with a 900-ml linear NaCl gradient of 0-0.6 M in the same buffer. Fractions containing pure heparanase, determined by silver staining of sodium dodecyl sulfate-polyacrylamide gel electrophoresis (SDS-PAGE), were pooled, dialyzed into 10 mM sodium phosphate (pH 7.0), concentrated using Centriplus concentrating devices (Millipore), and stored at −80° C. until use.

Assay solutions (100 μl) were composed of 40 mM sodium acetate buffer (pH 5.0) and 100 mM fondaparinux (GlaxoSmithKline) with or without inhibitor. Heparanase was added to a Final concentration of 140 μM, unless stated otherwise, to start the assay. The plates were sealed with adhesive tape and incubated at 37° C. for 2-24 h before the assays were stopped by the addition of 100 μl of a solution containing 1.69 mM 4-[3-(4-iodophenyl)-2-(4-nitrophenyl)-2H-5-tetrazolio]-1,3-benzene disulfonate (WST-1) in 0.1 M NaOH. The plates were resealed with adhesive tape and developed at 60° C. for 60 min, and the absorbance was measured at 584 nm (FLUOstar, BMG Labtech).

Example 4.2: Assay Results

Figure 2:
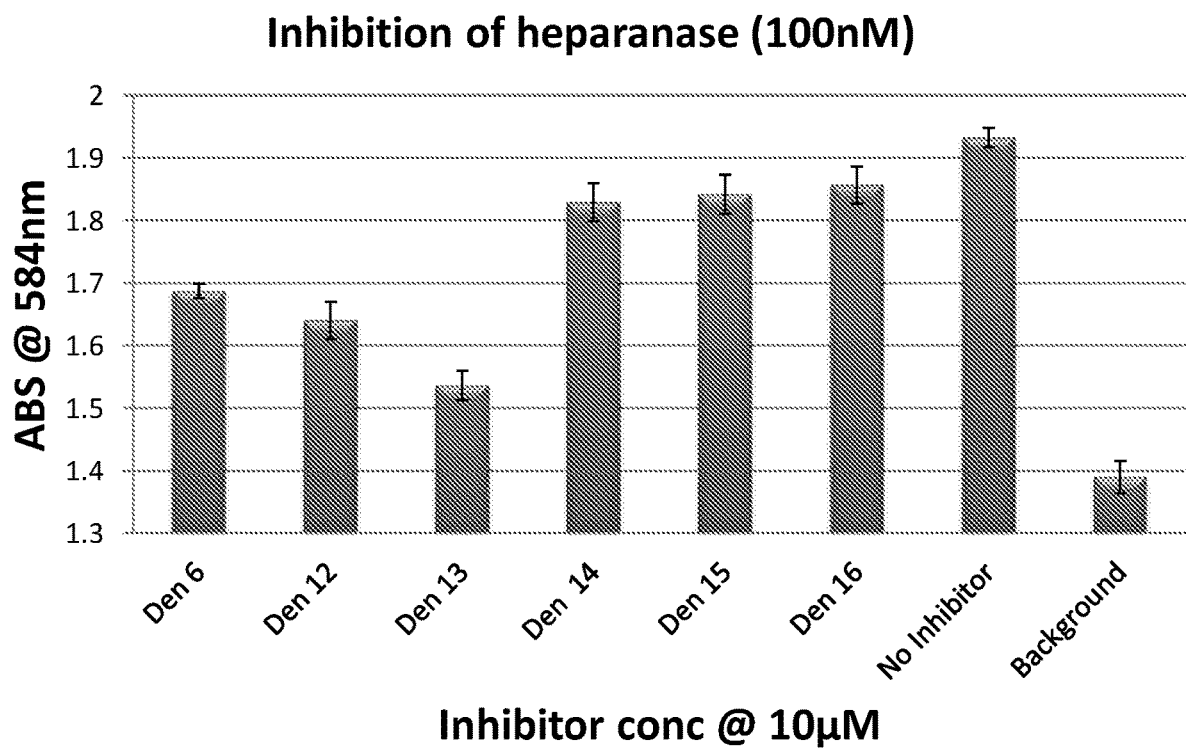
FIG. 2 shows the inhibition of heparanase by compounds of the invention at an inhibitor concentration of 10 μM.
Figure 3:
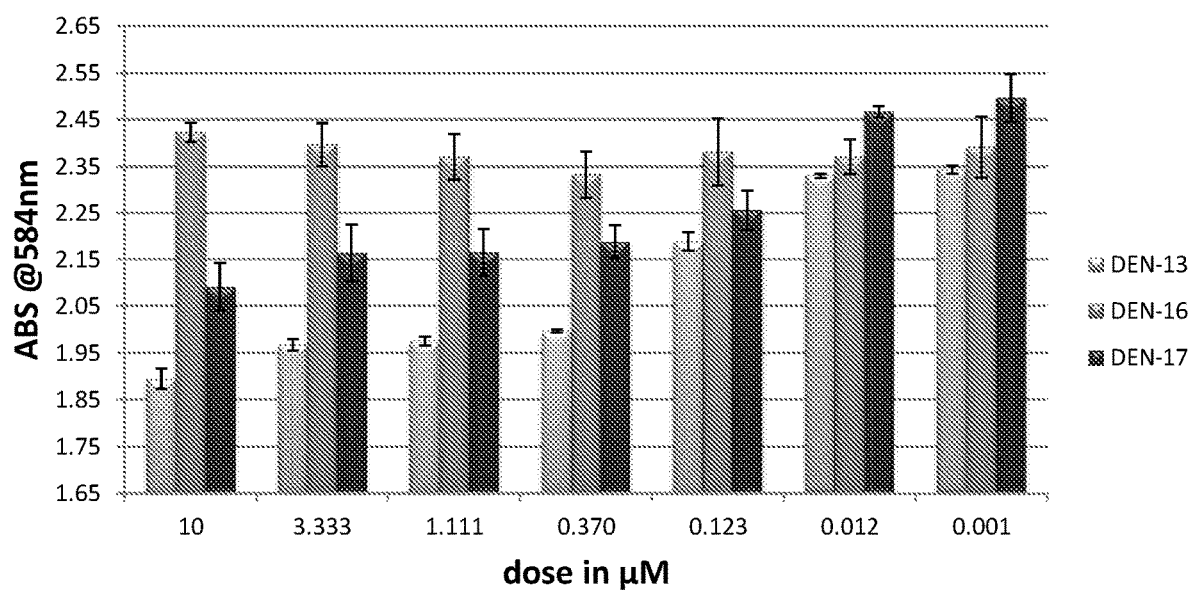
FIG. 3 shows heparanase inhibition dose response of compounds of the invention.

The results from the heparanase inhibition assay are shown in FIGS. 1 to 3. The compounds can be identified according to the following key:
Den 12=Compound 25a (Scheme 6)
Den 13=Compound 17c (Scheme 3)
Den 14=Compound 17b (Scheme 3)
Den 15=Compound 17d (Scheme 3)
Den 16=Compound 25b (Scheme 6)
Den 17=Compound 17a (Scheme 3)

FIG. 1 shows the inhibition of heparanase by compounds 17c, 25b and 17a, against a control (negative control, no heparanase) and a positive control of HPE (heparanase alone with no inhibitor), at inhibitor concentrations of 1 μM.

FIG. 2 shows the inhibition of heparanase by compounds 25a, 17c, 17b, 17d and 25b, against a background control (no heparanase added) and a positive control with no inhibitor (heparanase alone), at an inhibitor concentration of 10 μM.

FIG. 3 shows the dose response of compounds 17c, 25b, and 17a.

Compounds 17a-d, 25a and 25b were assessed as inhibitors of heparanase. All compounds showed the ability to inhibit heparanase, with compounds 17a, 17b and 17c found to be particularly good inhibitors. In addition, compound 17b showed very good inhibition of heparanase at various concentrations in solution.

Example 5: Cholesterol Activity in NPC

Example 5.1: Assay Methodology

Cell Culture and Cell Lines

Fibroblast cell lines derived from Alzheimer and Niemann-Pick Type C (NPC) patients and healthy controls were obtained from the Cornell Institute for Medical Research (Camden, N.J., USA). Cell line GM03123 was derived from a 9 year old NPC patient with two heterozygous mutations in the NPC1 gene. Cell line GM09503 was used as a healthy control for the NPC cell line. Cell line ND41001 was derived from a 47 year old patient carrying a Presenilin 1 mutation with familial (early onset) Alzheimer's disease (AD). Cell line ND38530 was used as a healthy control for the AD cell line. Further details of the cell lines are available at the Cornell Cell Repository website (https://catalog.coriell.org/).

Cell culture work was carried out in sterile conditions in an Email Air Handling Class II Biological Safety Cabinet (AES Environmental Pty LTD, Australia). All cell lines were cultured in DMEM (10313-021, Life Technologies New Zealand) supplemented with 10% fetal calf serum (Thermo Fisher Scientific New Zealand), 1× GlutaMAX™ Supplement (stabilised L-glutamine, Gibco Life Technologies New Zealand), 100 units/mL penicillin and 100 units/mL streptomycin (Life Technologies New Zealand). Cell lines were maintained in or 75 cm² flasks (Corning, Invitro Technologies New Zealand) in a humidified incubator (Sanyo Electric Co. Ltd, Japan) at 37° C. and 5% $CO_2$. Experimental cultures were carried out in the same media omitting the antibiotics to avoid any potential interaction with the compound being tested.

For experiments, cells were seeded at a density of 1.25× $10^3$ cells/mL in black, 96 well plates (Cell-carrier, Perkin Elmer, Scimed New Zealand) in a volume of 100 μL media and grown for 24 hours before treating. The media was then replaced with fresh media supplemented with the required treatment. Cell lines GM03123 and ND41001 were either left untreated, or treated with either 10 μM or 100 μM of the heparan sulphate compound dissolved in sterile deionised water ($dH_2O$), 10 μM suberoylanilide hydroxamic acid (SAHA) dissolved in DMSO, or 0.1% DMSO. The healthy control cell lines GM09503 and ND38530 were left untreated or treated with U18666A dissolved in sterile $dH_2O$ at a final concentration of 1 μg/mL. U18666A causes cholesterol accumulation in the cell and is therefore a positive control for the filipin stain. Cells were then grown for 48 hours.

Filipin Staining and Confocal Microscopy

Before fixing, cells were washed three times with 1× phosphate buffered saline (PBS). From this point all treatments and washes were undertaken on a rotating table at 45 revs per minute. Cells were fixed with 1.5% paraformaldehyde (PFA) in 1×PBS (Thermo Fisher Scientific New Zealand) for 20 minutes. Cells were then washed with 1×PBS for four minutes. This was repeated twice. The cells were then stained for 2 hours with 50 μg/mL Filipin dye (Filipin complex from *Streptomyces filipinensis*, Sigma Aldrich, Australia) protected from the light. With minimal light exposure, the cells were washed with 1×PBS for four minutes and this was repeated twice. Cells were left in 1×PBS for confocal microscopy. The filipin stained cells were imaged using a Perkin Elmer Opera™ high-throughput spinning disk confocal microscope using 405 nm laser and 20× water immersion objective. Perkin Elmer Acapella™ software was used for image analysis. In NPC cells cholesterol accumulates in organelles with the characteristics of late endosomes or early lysosomes. These can be described as lysosome-like storage organelles (LSO). Analysis of free cholesterol levels in the cells was carried out using a method designed for high throughput confocal images described by Pipalia et al., Automated microscopy screening for compounds that partially revert cholesterol accumulation in Niemann-Pick C cells, J. Lipid Res., 2006, 47(2): 284-301. A low fluorescence threshold was chosen which identified the total area occupied by cells and another higher threshold was chosen to determine the areas of bright filipin staining of cholesterol within the cell. These regions were generally perinuclear.

The lysosome-like storage organelle (LSO) ratio was defined as:
LSO ratio=total intensity above high threshold/number of pixels above low threshold.
Percent LSO (% LSO) values were defined as:
LSO ratio (treated)/LSO ratio (untreated)×100.
Statistical significance was determined by a two-tailed student's T-test.
SAHA is a histone deacetylase (HDAC) inhibitor and was used as a standard.

Example 5.2: Assay Results

The results from the NPC cholesterol activity assay are shown in Table 1. Compounds 17c and 25a showed a positive effect on filipin (cholesterol) fluorescence in fibroblast cells derived from Niemann-Pick type C and Alzheimer's disease patients. These compared favourably to a clinically approved histone deacetylase (HDAC) inhibitor SAHA with the ability to reverse the dysregulation of the majority of HDAC genes. The results of the bioassay correlate with changes in lysosomal accumulation of both cholesterol and sphingolipids in organisms, defective esterification of cholesterol and multiple aspects of lipid transport. HDAC inhibition is identified as a potential novel and promising therapy for NPC disease.

TABLE 1

| | NPC cholesterol activity | | | |
| --- | --- | --- | --- | --- |
| Compound | GM03123 (NPC), LSO % 10 µM | GM03123 (NPC), LSO % 100 µM | ND41001 (AD), LSO % 10 µM | ND41001 (AD), LSO % 100 µM |
| SAHA | 43.0 | — | 42.4 | — |
| 25a | 76.1 | 64.2 | 60.1 | 67.9 |
| 17c | 73.0 | 56.6 | 61.2 | 57.4 |

Example 6: Treatment of Myeloma in Mice

Using methodology reported in Weissmann et al., (PNAS, 113(2016), 704), NOD/SCID mice (n=12) were inoculated with human CAG myeloma cells labeled with luciferase ($5*10^6$ cells/mouse) by intravenous injection. Starting 24 hours after inoculation, a treatment group (n=6) was administered daily with 600 µg of compound 17c (see Example 3.25 above) dissolved in 100 µL of phosphate buffered saline by intraperitoneal injection during 4 weeks. A control group (n=6) was similarly injected with 100 µL of phosphate buffered saline. Starting from week 2, images of in vivo luminescence signal were detected, 5-20 min after the mice were injected with luciferin. Quantification of whole body bioluminescent images from animals was performed using Living Image® software. Mice were injected intraperitoneally with D-luciferin substrate at 150 mg/kg, anesthetised, and placed onto a stage inside the light-tight camera box, with continuous exposure to isoflurane (EZAnesthesia). Light emitted from the bioluminescent cells was detected by the IVIS camera system, with images quantified for tumour burden using a log-scale colour range set at $5\times10^4$ to $1\times10^7$ and measurement of total photon counts per second, using Living Image software (Xenogen). Images were collected from individual animals from both ventral (front) and dorsal (back) positions.

Figure 4:
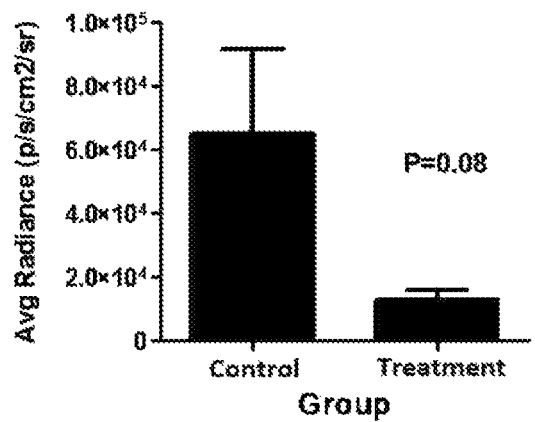
FIG. 4 shows average radiance determined at 3 and 4 weeks for control mice and mice treated with compound 17c (Top left: back of mice, 3 weeks after inoculation; Top right: front of mice, 3 weeks after inoculation; Bottom left: back of mice, 4 weeks after inoculation; Bottom right: front of mice, 4 weeks after inoculation).
Figure 4:
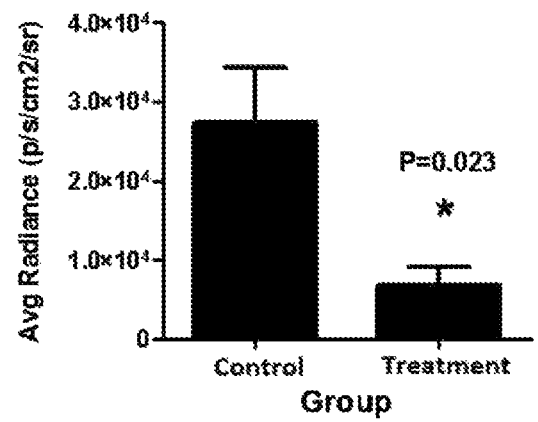
Figure 4:
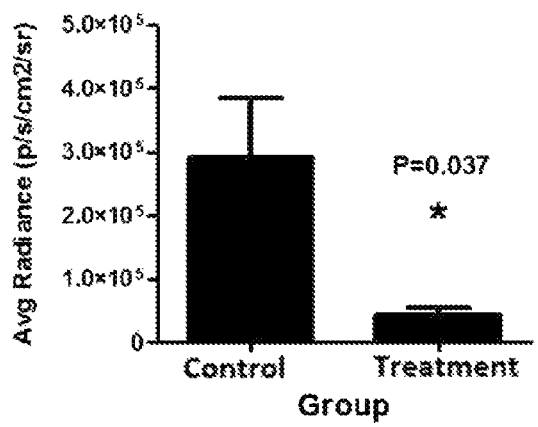
Figure 4:
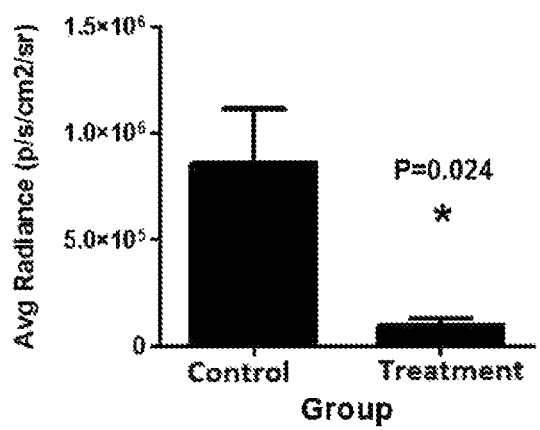

The results at weeks 3 and 4 are shown in FIG. 4. They demonstrate that treatment with compound 17c caused a significant reduction of tumour burden in treated compared to untreated mice.

Example 7: Production of Collagen Type I

Cells from the human dermal fibroblast cell line, CRL2071 (passages 12-14), obtained from normal breast skin of a 52 year old Caucasian female, were allowed to attach for 6-8 hours before the addition of the test compounds. After 72 h of exposure to the test articles the media was removed, cells counted and the cell-associated fraction extracted. The media and cell-associated fraction were analysed for the concentration of collagen type I using a Chondrex Human type I Collagen Detection Kit ELISA (Cat #6021).

After complete dissolution the solutions were sterile filtered through a 0.22 µM syringe filter and kept at 4° C. until use. Prior to each experiment dilutions were freshly prepared by diluting to 100 nM, 1 µM or 10 µM in cell-specific media.

The test compounds, positive controls and no treatment media were added to the flasks (2.5 ml/flask) and cells were incubated for 72 h before removal of the supernatant. After removal of the supernatant, cell monolayers were trypsinsed with 2.5 ml of 0.025% trypsin/0.1 mm EDTA in PBS to each flask. After cell detachment (7-10 min), 1 ml of the cell/trypsin mixture was added to a 20 ml counting vial containing 9 ml of normal saline. The cells were quantitated with a Coulter Counter Z2.

In some treatments cells were found floating. They were collected, counted and subjected to viability testing using 1% trypan blue staining. The remaining 1.5 ml of trypsin/cell mixture was sonicated with a Branson tip-probed sonicator for 1 min, setting 6 before centrifugation at 10,000 rpm for 10 min. The supernatant was removed and used in the collagen ELISA for the quantitation of cell-associated collagen.

TABLE 2

Effect of heparanase inhibitors on collagen type I

| Treatment | μg collagen (Mean ± SD) | Collagen as % of No Treatment Control (Mean ± SD) | Is treatment significantly better than No Treatment? | Ranking of statistically significant data 1 = best |
|---|---|---|---|---|
| Liberated Collagen Type 1 | | | | |
| No treatment control | 0.04 ± 0.00 | 100 ± 0 | Not applicable | |
| TGF-β2 + ve control (20 ng/ml) | 0.19 ± 0.03 | 446 ± 73 | YES: 0.017 | |
| TGF-β1 + ve control (20 ng/ml) | 1.23 ± 0.12 | 2,852 ± 285 | YES: 0.004 | 2 |
| Bakuchiol + ve control (5 μg/ml) | 0.02 ± 0.01 | 43 ± 17 | YES: 0.012 | |
| Bakuchiol + ve control (10 μg/ml) | 0.15 ± 0.01 | 357 ± 20 | NO: 0.250 | |
| B2: 1 μM | 0.39 ± 0.05 | 902 ± 108 | NO: 0.066 | |
| B2: 10 μM | 0.21 ± 0.02 | 492 ± 34 | YES: 0.050 | |
| 17b: 1 μM | 4.36 ± 0.26 | 10,072 ± 604 | YES: 0.028 | 1 |
| 17b: 10 μM | 0.01 ± 0.01 | 23 ± 2 | YES: 0.043 | |
| 17d: 1 μM | 0.06 ± 0.07 | 146 ± 13 | NO: 0.214 | |
| 17d: 10 μM | 0.24 ± 0.04 | 544 ± 82 | NO: 0.092 | |
| 16a: 1 μM | 1.11 ± 0.04 | 2,558 ± 94 | YES: 0.019 | 3 |
| 16a: 10 μM | 0.43 ± 0.07 | 997 ± 151 | NO: 0.080 | |
| 17a: 1 μM | Not Detected | Not Detected | Not applicable | |
| 17a: 10 μM | 0.54 ± 0.05 | 1,251 ± 107 | YES: 0.038 | |
| 17c: 1 μM | Not Detected | Not Detected | Not applicable | |
| 17c: 10 μM | Not Detected | Not Detected | Not applicable | |
| Cell-Associated Collagen Type 1 | | | | |
| No treatment control | 0.04 ± 0.00 | 100 ± 0 | Not applicable | |
| TGF-β2 + ve control (20 ng/ml) | 0.03 ± 0.00 | 77 ± 9 | NO: 0.249 | |
| TGF-β1 + ve control (20 ng/ml) | 0.31 ± 0.02 | 719 ± 57 | YES: 0.003 | |
| Bakuchiol + ve control (5 μg/ml) | 0.28 ± 0.02 | 1,085 ± 60 | YES: <0.001 | |
| Bakuchiol + ve control (10 μg/ml) | 0.29 ± 0.01 | 600 ± 348 | NO: 0.136 | |
| 17b: 1 μM | 0.50 ± 0.01 | 1,155 ± 25 | YES: 0.019 | |
| 17b: 10 μM | 1.02 ± 0.02 | 2,371 ± 49 | YES: 0.006 | 3 |
| 17d: 1 μM | 1.32 ± 0.35 | 3,076 ± 803 | NO: 0.123 | |
| 17d: 10 μM | 2.20 ± 0.10 | 5,116 ± 231 | YES: 0.022 | 1 |
| 16a: 1 μM | 1.92 ± 0.01 | 4,462 ± 28 | YES: <0.001 | 2 |
| 16a: 10 μM | 0.53 ± 0.04 | 1,219 ± 82 | YES: 0.041 | |
| 17a: 1 μM | 0.75 ± 0.13 | 1,739 ± 296 | NO: 0.076 | |
| 17a: 10 μM | 0.79 ± 0.05 | 1,508 ± 112 | YES: 0.024 | 4 |
| 17c: 1 μM | 0.70 ± 0.16 | 1,629 ± 377 | NO: 0.105 | |
| 17c: 10 μM | 0.62 ± 0.03 | 1,447 ± 68 | YES: 0.016 | 5 |

Mean ± SD is the result of 2-3 biological replicates
Bakuchiol (Syntenol ® A): Sytheon Ltd., Boonton, NJ 07005, USA.
Transforming growth Factor β1: Sigma Aldrich, St Louis, USA.
Transforming growth Factor β2: Sigma Aldrich, St Louis, USA.

Example 8: Inhibition of Bacterial Collagenase Type II

A colorimetric gelatinolytic assay was used to evaluate the effects of heparanase inhibitors on the activity of bacterial collagenase type II from *Clostridium histolyticum*. The reaction mixture was prepared in a total volume of 20 μl for each well of the microplate/inhibition assay. First, 1 ul of 100 ng of bacterial collagenase and 2 μl of the heparanase inhibitor or positive control (50 μg/ml doxycycline) were added into each well of a 96-well plate and incubated at 37° C. for 60 min. On completion of the incubation, 10 μg of gelatin and 2 μl of 10× collagenase buffer (500 mM Tris-HCl, 100 mM $CaCl_2$, and 1.5 M NaCl) were added to distilled water to obtain the final volume of 20 μl. The plate was then incubated at 37° C. for 4 h. Subsequently, the amount of gelatin remaining was quantified by the addition of 20 μl of 2.5% w/v of Coomassie Brilliant blue R-250 (Sigma-Aldrich) dissolved in 40% methanol/10% acetic acid, followed by shaking on an orbital shaker for 5 min. The supernatant was carefully removed by pipette to ensure that the gelatin pellet was not disturbed and 50 μl of dimethyl sulfoxide was added to dissolve the pellet. The plate was incubated at room temperature for 15 min followed by shaking on an orbital shaker for 5 min. The plate was then read in a Versa max microplate reader at 600 nm.

TABLE 3

Effect of heparanase inhibitors on collagenase type II from Clostridium histolyticum

| Treatment | Collagenase inhibition as a % of the "No Treatment" control (Mean ± SD) | Collagen as % of No Treatment Control (Mean ± SD) | | Hyaluronan as % of No Treatment Control (Mean ± SD) |
|---|---|---|---|---|
| | | Liberated | Cell-associated | Liberated |
| 17b: 10 µM | 74 ± 2 | 23 ± 2p = 0.043 | 2,371 ± 49P = 0.006 | 167 ± 36p = 0.233 |

Example 9: Production of Hyaluronan

Cells from the human dermal fibroblast cell line, CRL2071 (passages 12-14), obtained from normal breast skin of a 52 year old Caucasian female, were allowed to attach for 6-8 hours before the addition of the test compounds. After 72 h of exposure to the test articles the media was removed, cells counted and the cell-associated fraction extracted. The media and cell-associated fraction were analysed for the concentration of hyaluronan using a Hyaluronan Detection Kit ELISA.

The test compounds, positive controls and no treatment media were added to the flasks (2.5 ml/flask) and cells were incubated for 72 h before removal of the supernatant. After removal of the supernatant, cell monolayers were trypsinsed with 2.5 ml of 0.025% trypsin/0.1 mm EDTA in PBS to each flask. After cell detachment (7-10 min), 1 ml of the cell/trypsin mixture was added to a 20 ml counting vial containing 9 ml of normal saline. The cells were quantitated with a Coulter Counter Z2.

In some treatments cells were found floating. They were collected, counted and subjected to viability testing using 1% trypan blue staining. The remaining 1.5 ml of trypsin/cell mixture was sonicated with a Branson tip-probed sonicator for 1 min, setting 6 before centrifugation at 10,000 rpm for 10 min. The supernatant was removed and used in the hyaluronan ELISA for the quantitation of cell-associated hyaluronan.

TABLE 4

Effect of treatments on synthesis and liberation of hyaluronan (>6400Da)

| Treatment | ng Hyaluronan/ 1 × 10[6] cells (Mean ± SD) | Hyaluronan as % of No Treatment Control (Mean ± SD) | Is Treatment significantly better than No treatment | Ranking of statistically Significant data 1 = best |
|---|---|---|---|---|
| No treatment control | 43 ± 0 | 100 ± 0 | Not applicable | |
| TGF-β1 + ve control (20 ng/ml) | 507 ± 68 | 1,186 ± 159 | YES: 0.042 | 2 |
| Retinol + ve control (5 µg/ml) | 576 ± 0 | 1,346 ± 0 | YES: <0.001 | 1 |
| 17a: 1 µM | 145 ± 26 | 340 ± 60 | No: 0.112 | |
| 17a: 10 µM | 120 ± 7 | 281 ± 17 | YES: 0.043 | 5 |
| 17c: 1 µM | 178 ± 52 | 416 ± 121 | No: 0.168 | 6 |
| 17c: 10 µM | 99 ± 3 | 231 ± 7 | YES: 0.024 | |

Mean ± SD is the result of 2-3 biological replicates

Example 10: Inhibition of Tyrosinase

The human primary epidermal melanocyte cell line (PCS-200-013) was attached for 24 h before incubation with the test reagents for 72 h. After incubation, cells were solubilised and tyrosinase activity was determined using L-dopa as the substrate and a standard curve of mushroom tyrosinase was established to quantitate the inhibitory activity of each compound. After 72 h of exposure to the test and control compounds, the cell monolayers were washed in 1 ml of PBS and solubilised in 1 ml of 0.5% (v/v) Triton X-100 in 50 mM sodium phosphate buffer (pH 6.9), and freeze-thawed by incubating at −80° C. for 30 min followed by room temperature for 25 min and 37° C. for 5 min. This cell extract was analysed for tyrosinase activity.

Tyrosinase activity was estimated using a modified mushroom tyrosinase assay. First, 3 ml of 8 mM L-DOPA (Sigma, USA) dissolved in 50 mM phosphate buffer, pH 6.8, was added to a the 1 ml of tube, the above cell extracts and the tubes were incubated at 37° C. for 60 min. The tubes were read in a Pharmacia Novatec Model II at $A_{492}$ nm with each tube being read against a blank.

TABLE 5

Effect of heparanase inhibitors on the activity of cellular tyrosinase

| Treatment | Tyrosinase inhibition as a % of the "No Treatment" control (Mean ± SD) | Statistical Significance compared to the "No Treatment" control |
|---|---|---|
| No Treatment Control | 0 ± 0 | Not Tested |
| 17d: 100 nM | 0 ± 0 | P = 1.00 |
| 17d: 1 µM | 0 ± 0 | P = 1.00 |
| 17d: 10 µM | 44 ± 2 | YES: P = 0.002 |
| 17c: 100 nM | 0 ± 0 | P = 1.00 |
| 17c: 1 µM | 0 ± 0 | P = 1.00 |
| 17c: 10 µM | 21 ± 2 | YES: P = 0.002 |

Example 11: Inhibition of Hyaluronidase

The heparanase inhibitors were incubated with testicular hyaluronidase in the presence of hyaluronan and after incubation the amount of hyaluronic acid remaining was quantitated. Hyaluronidase activity was measured according to the method of Tolksdorf [Tolksdorf, S. & McCready, M. H., The turbometric determination of hyaluronidase, The Journal of Laboratory and Clinical Medicine, 1949, 34(1):74-89]. Hyaluronic acid is measured by its ability to form turbidity with an acid albumin solution. Turbidity is a function of hyaluronic acid concentration and can hence be related to enzyme activity. One unit is based on the change in absorbency (turbidity) at 540 nm of an internal USP standard. All tubes were placed in a boiling water bath for 5 min and then cooled to room temperature. On cooling 9.0 ml of albumin reagent was added and tubes were allowed to stand for 10 min. Readings of absorbance at 540 nm in a Pharmacia Novatec Model II were taken. The $A_{540nm}$ was plotted versus the hyaluronic acid concentration (mg) to form a standard curve.

TABLE 6

Effect of heparanase inhibitors on the activity of testicular hyaluronidase

| Treatment | Hyaluronidase inhibition as a % of the "No Treatment" control (Mean ± SD) | Statistical Significance compared to the "No Treatment" control |
|---|---|---|
| Porcine heparin + ve control: 100 nM | 0 ± 0 | P = 1.00 |
| Porcine heparin + ve control: 1 µM | 13 ± 1 | YES: P = 0.017 |
| Porcine heparin + ve control: 10 µM | 56 ± 2 | YES: P < 0.001 |
| No Treatment Control | 0 ± 0 | Not Tested |
| 17d: 100 nM | 0 ± 0 | P = 1.00 |
| 17d: 1 µM | 0 ± 0 | P = 1.00 |
| 17d: 10 µM | 23 ± 1 | YES: P = 0.021 |
| 17c: 100 nM | 0 ± 0 | P = 1.00 |
| 17c: 1 µM | 0 ± 0 | P = 1.00 |
| 17c: 10 µM | 19 ± 0 | YES: P = 0.011 |

INDUSTRIAL APPLICABILITY

The invention relates to compounds that are useful for the treatment or prevention of diseases including cancer, inflammation, diabetic nephropathy, neurodegenerative disorders, Niemann-Pick Type C disease, and for certain cosmeceutical and dermatological uses.

The invention claimed is:
1. A compound of formula (i):

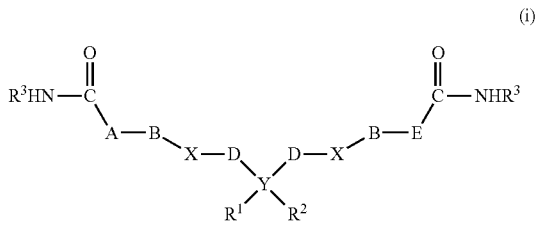

(i)

wherein:
$R^3$ is a radical of formula (ii), (iii) or (iv):

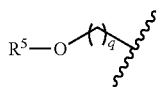

(ii)

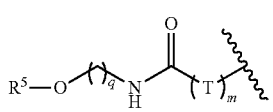

(iii)

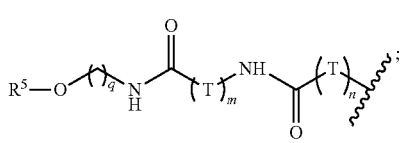

(iv)

$R^5$ is a radical of formula (vii):

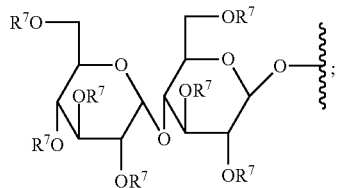

(vii)

$R^7$ $SO_3H$;
and:
Y is O; B is O; $R^1$ and $R^2$ are absent; and either A, E, D and X are all $CH_2$; or A, D and X are all $CH_2$ and E is $(CH_2CH_2O)_t{}^{\#}CH_2$ wherein $^{\#}$ indicates a point of attachment of E to its adjacent carbonyl group; t is an integer from 1 to 10;
or:
Y is C; $R^1$ and $R^2$ are both H; and A, E, B and D are $CH_2$ and X is O;
or:
Y is C; A is $(CH_2)_u$; $R^1$ and $R^2$ are both H; B, X, D and E are all absent; and u is an integer from 1 to 10;
or:
Y is C; X is O; B is $(CH_2)_p$; A, E and D are all $CH_2$; and $R^1$ is H, NHZ or $C_{1-6}$alkyl and $R^2$ is a radical of formula (viii), (ix) or (x):

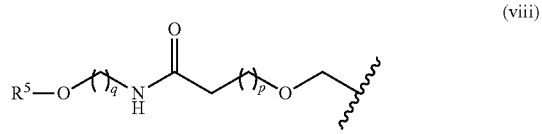

(viii)

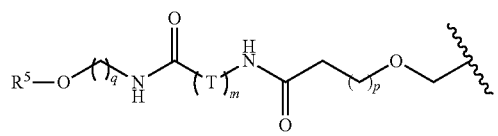

(ix)

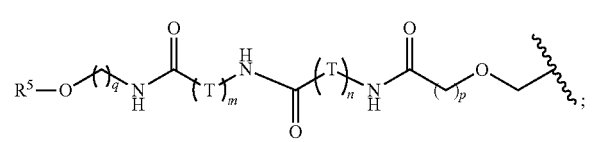

(x)

Z is H, acyl, $C(O)(CH_2)_wN(H)G$, or an imaging agent;
w is an integer from 1 to 11;
G is H, acyl, Boc (t-butoxycarbonyl), Troc (2,2,2-trichloroethyloxycarbonyl), Fmoc (9-fluorenylmethoxycarbonyl), Cbz (benzyloxycarbonyl), or an imaging agent;
or:
Y is C; X is O; B is $(CH_2)_p$; A, E and D are all $CH_2$; and $R^1$ and $R^2$, both the same, are a radical of formula (viii), (ix) or (x):

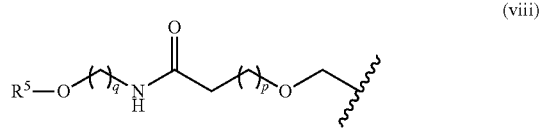

(viii)

(ix)

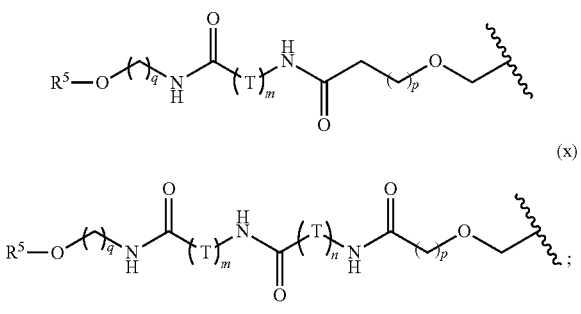

(x)

each T is independently selected from the group consisting of $(CH_2CH_2O)_xCH_2CH_2$ and $CH_2$;
each x is independently an integer from 1 to 12;
n is an integer from 1 to 11, provided that when T is $(CH_2CH_2O)_xCH_2CH_2$ then n is 1;
q is an integer from 1 to 11;
m is an integer from 1 to 11, provided that when T is $(CH_2CH_2O)_xCH_2CH_2$ then m is 1;
p is an integer from 1 to 5;
or a pharmaceutically acceptable salt thereof, or a prodrug thereof.

2. A compound as claimed in claim 1, wherein each T is $CH_2$.

3. A compound as claimed in claim 1, wherein at least one T is $(CH_2CH_2O)_xCH_2CH_2$.

4. A compound as claimed in claim 1, wherein $R^1$ and $R^2$ are both a radical of formula (viii):

(viii)

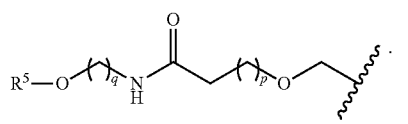

5. A compound as claimed claim 1, wherein $R^1$ and $R^2$ are both a radical of formula (ix):

(ix)

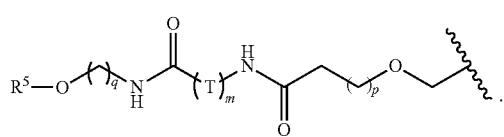

6. A compound as claimed claim 1, wherein $R^1$ and $R^2$ are both a radical of formula (x):

(x)

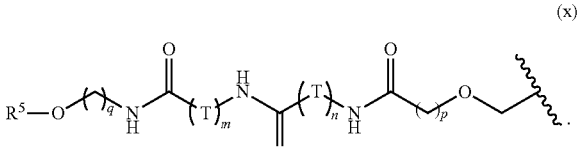

7. A compound as claimed in claim 1, wherein $R^3$ is a radical of formula (ii):

(ii)

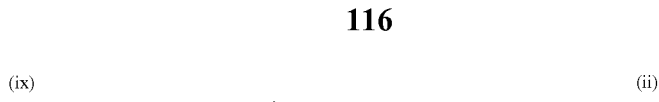

8. A compound as claimed in claim 1, wherein $R^3$ is a radical of formula (iii):

(iii)

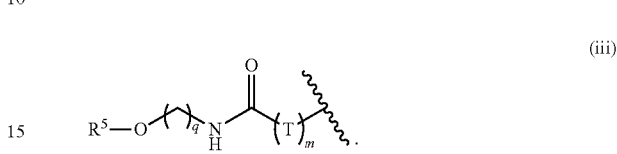

9. A compound as claimed in claim 1, wherein $R^3$ is a radical of formula (iv):

(iv)

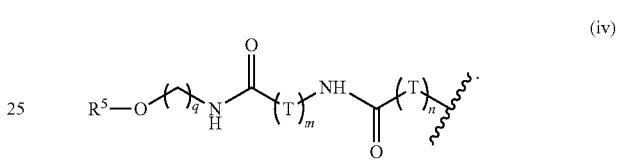

10. A compound as claimed in claim 1, wherein both of Z and G is an acetyl group.

11. A compound as claimed in claim 1, wherein Y is C; X is O; A, E and D are all $CH_2$; B is $(CH_2)_p$;
$R^1$ is H, NHZ or $C_{1-6}$alkyl;
$R^2$ is a radical of formula (viii), a radical of formula (ix) or a radical of formula (x):

(viii)

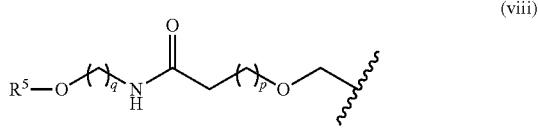

(ix)

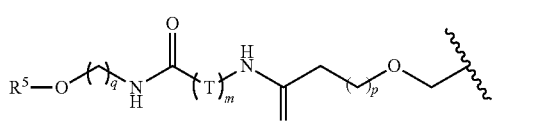

(x)

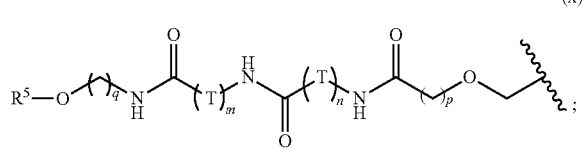

Z is H, acyl, $C(O)(CH_2)_wN(H)G$, or an imaging agent;
w is an integer from 1 to 11; and
G is H, acyl, Boc (t-butoxycarbonyl), Troc (2,2,2-trichloroethyloxycarbonyl), Fmoc (9-fluorenylmethoxycarbonyl), Cbz (carboxybenzyl), or an imaging agent.

12. A compound as claimed in claim 1, wherein Y is C; X is O; A, E and D are all $CH_2$; B is $(CH_2)_p$; and $R^1$ and $R^2$, both the same, are a radical of formula (viii), a radical of formula (ix) or a radical of formula (x):

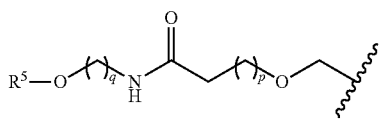

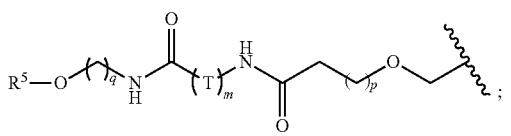

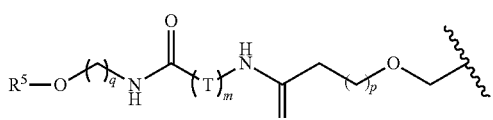

and R³ is a radical of formula (iii):

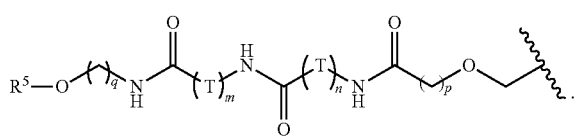

13. A compound as claimed claim 1, wherein Y is C; X is O; A, E and D are all CH₂; B is (CH₂)$_p$; R¹ and R², both the same, are a radical of formula (viii):

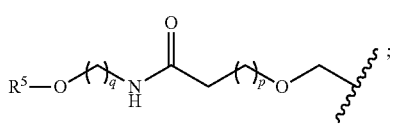

and R³ is a radical of formula (ii):

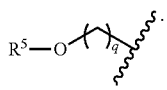

14. A compound as claimed in claim 1, wherein Y is C; X is O; A, B, E and D are all CH₂; R¹ and R², both the same, are a radical of formula (ix):

15. A compound as claimed in claim 1, wherein Y is C; X is O; A, B, E and D are all CH₂; R¹ and R², both the same, are a radical of formula (x):

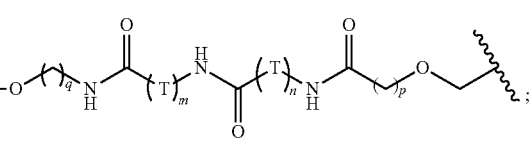

and R³ is a radical of formula (iv):

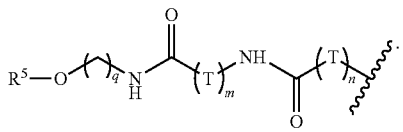

16. A compound as claimed in claim 1, wherein p is 1, q is 6, n is 7, or x is 3.

17. A compound as claimed in claim 1, wherein the compound of formula (i) is selected from the group consisting of:

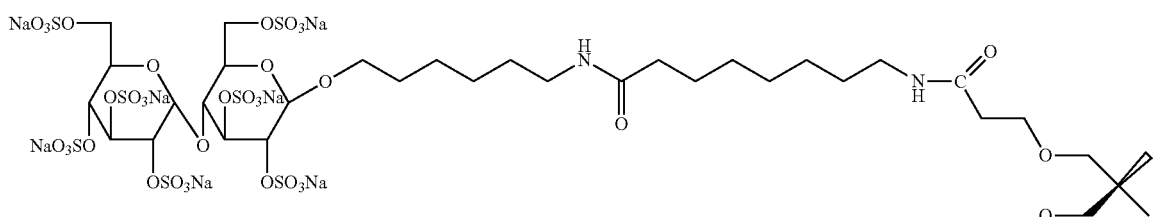
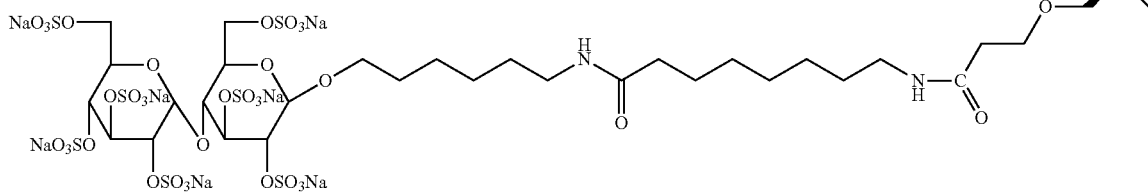

119 120
-continued
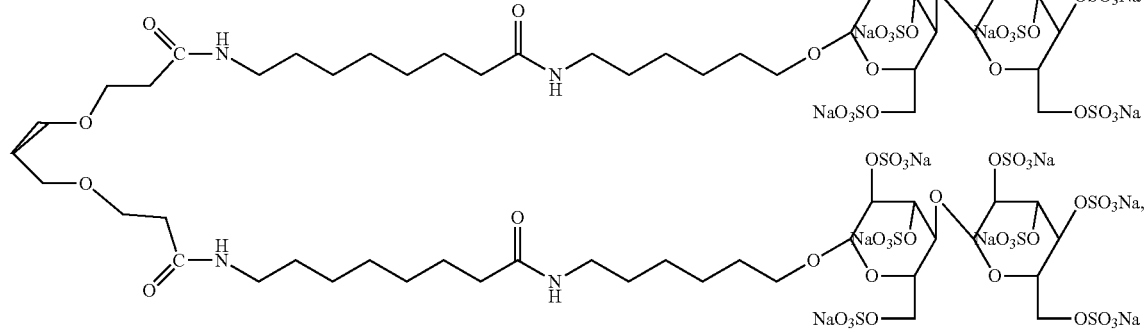
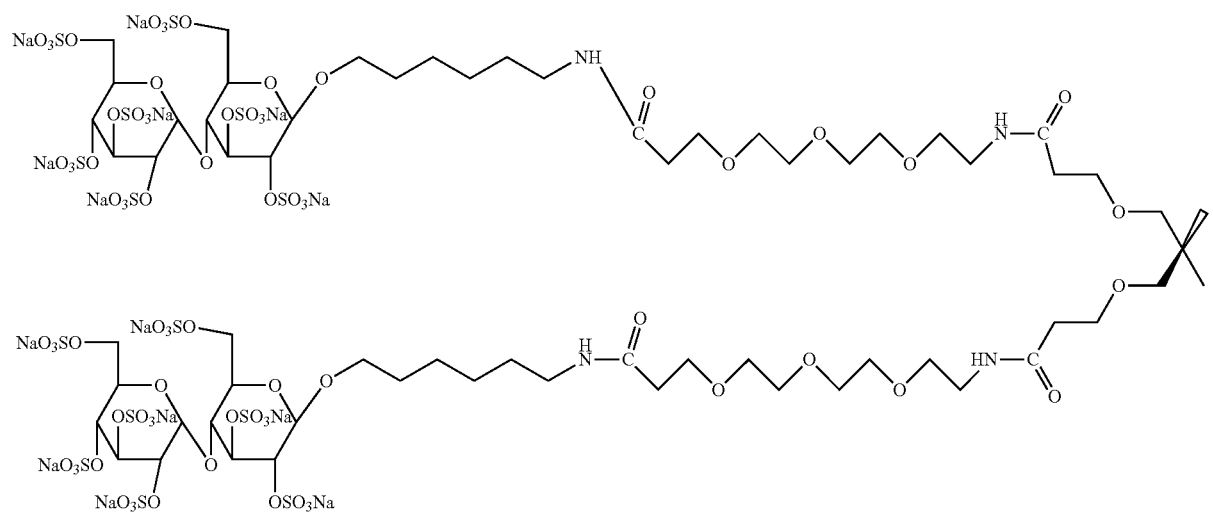
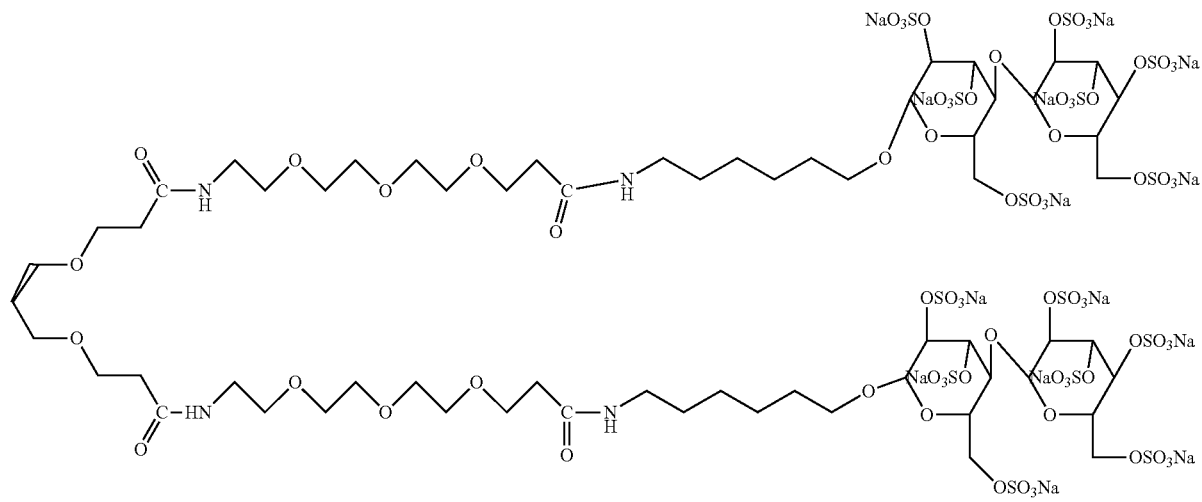

121
-continued
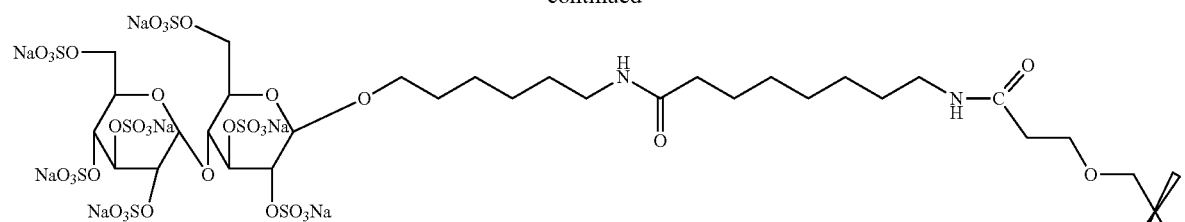
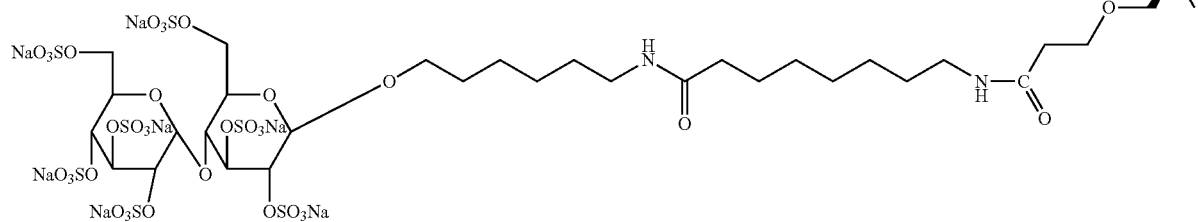
122
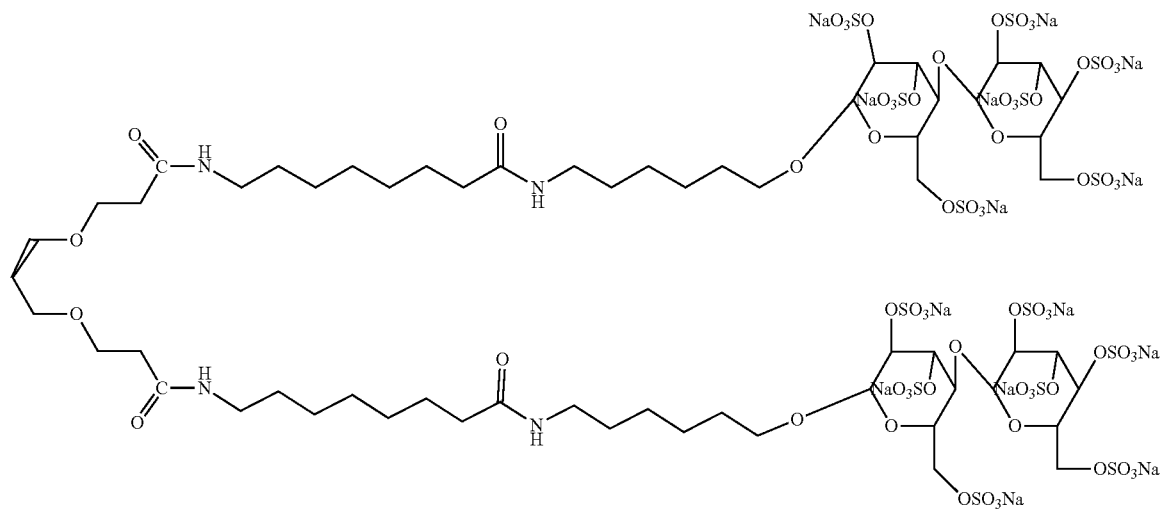
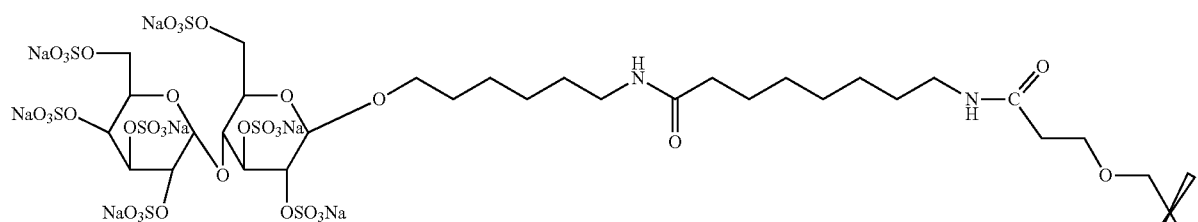
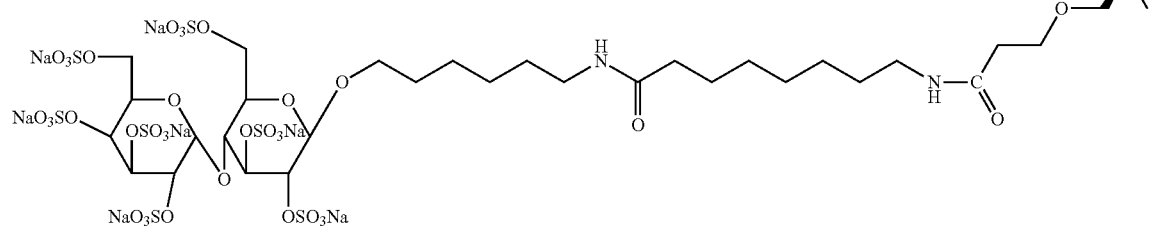

123 124
-continued
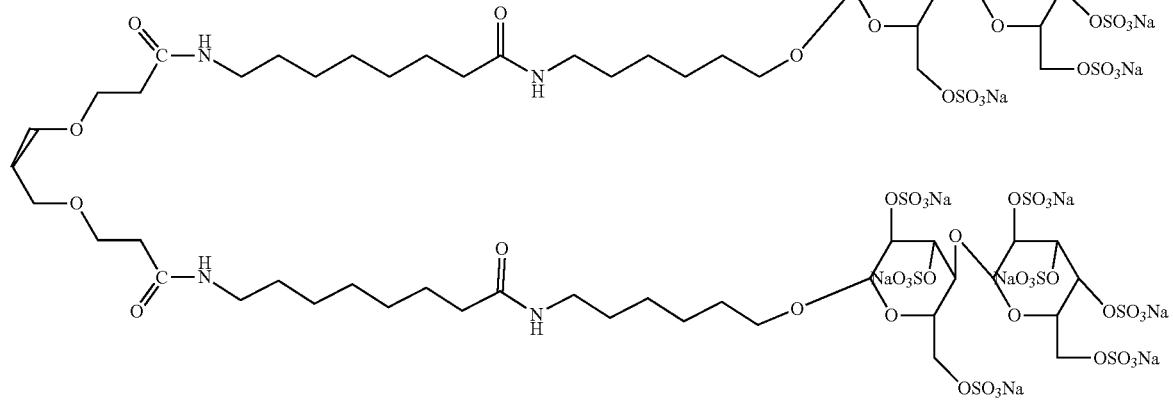
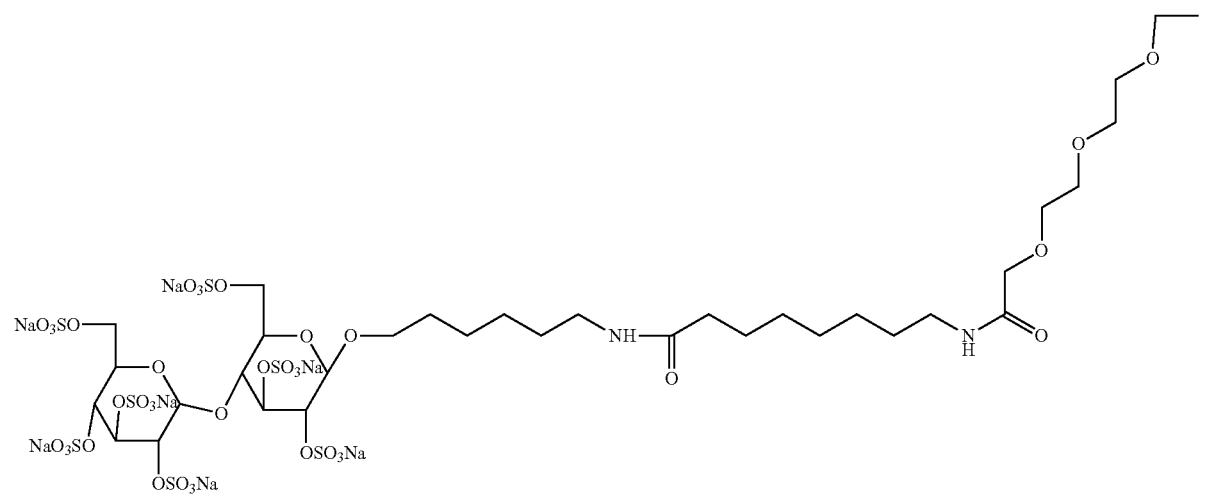
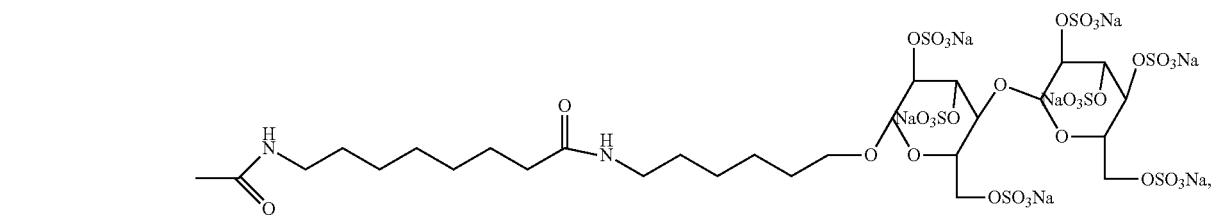
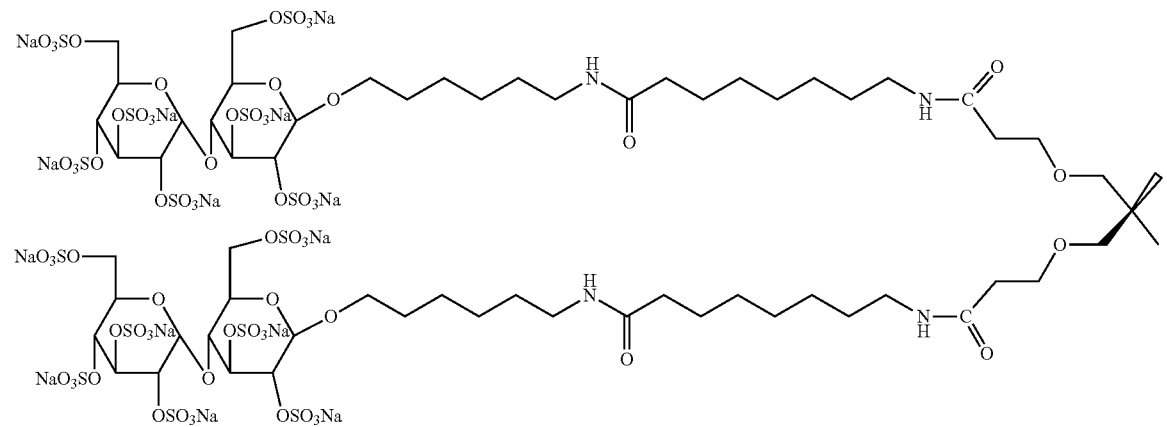

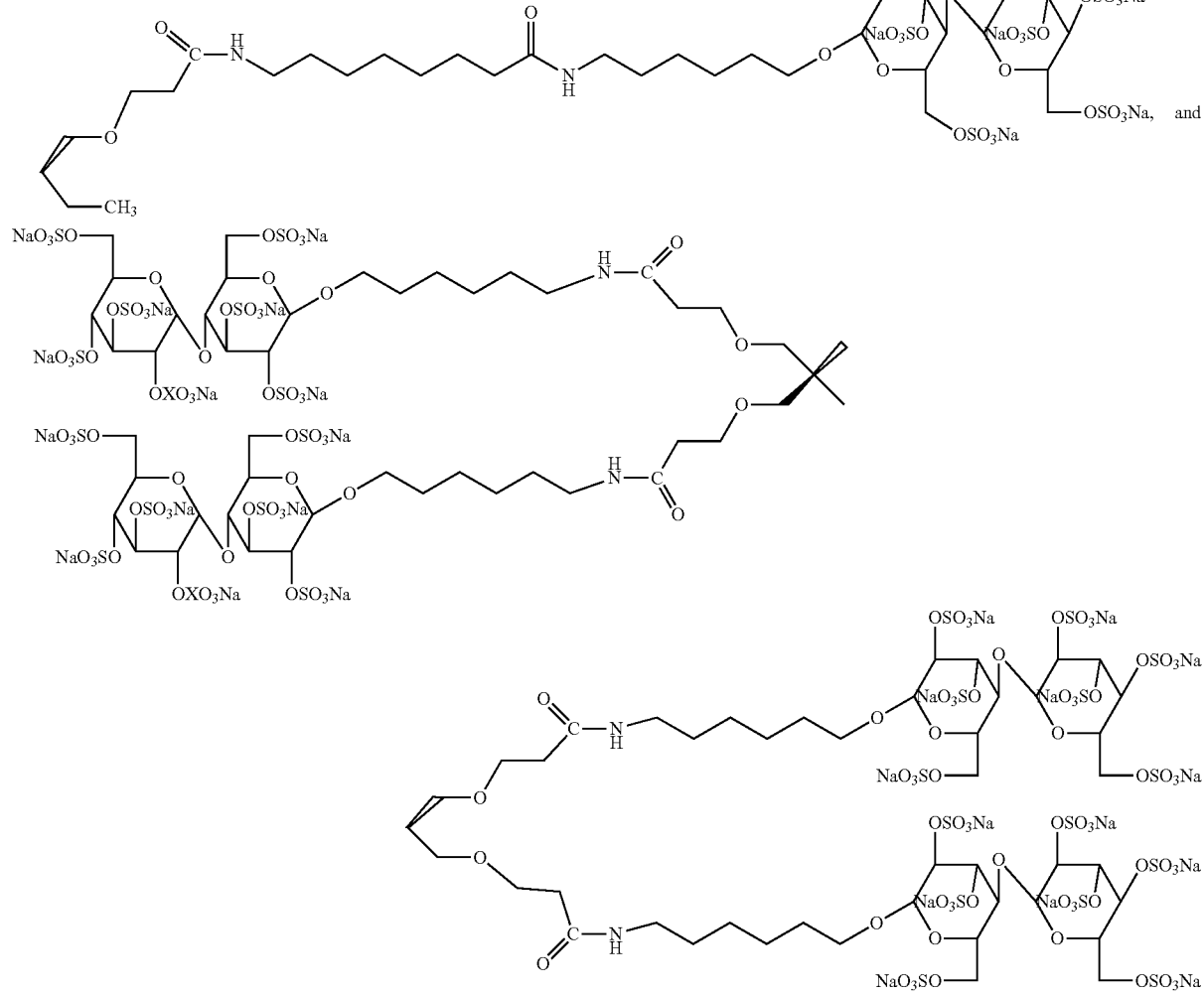
or a pharmaceutically acceptable salt thereof.
18. A pharmaceutical composition or cosmeceutical composition comprising an effective amount of a compound of claim 1 and a suitable carrier, diluent or excipient.
19. A method of rejuvenating skin or preventing skin-aging comprising administering an effective amount of a compound of claim 1 to human skin.
* * * * *